(12) United States Patent
Karlsson et al.

(10) Patent No.: US 6,265,397 B1
(45) Date of Patent: Jul. 24, 2001

(54) AMIDINO DERIVATIVES AND THEIR USE AS THROMBIN INHIBITORS

(75) Inventors: Olle Karlsson; Marcel Linschoten; Jan-Erik Nyström, all of Mölndal (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/091,994

(22) PCT Filed: Jun. 9, 1998

(86) PCT No.: PCT/SE98/01103

§ 371 Date: Jun. 26, 1998

§ 102(e) Date: Jun. 26, 1998

(87) PCT Pub. No.: WO98/57932

PCT Pub. Date: Dec. 23, 1998

(30) Foreign Application Priority Data

Jun. 19, 1997 (SE) .................................................. 9702378
Mar. 30, 1998 (SE) .................................................. 9801099

(51) Int. Cl.[7] .......................... C07D 205/04; A61K 31/37
(52) U.S. Cl. ........................... 514/210.17; 514/210.18; 548/950; 548/953
(58) Field of Search ........................... 548/953, 950; 514/210.17, 210.18

(56) References Cited

U.S. PATENT DOCUMENTS

| | | | |
|---|---|---|---|
| 4,346,078 | 8/1982 | Bajusz et al. | 424/177 |
| 4,703,036 | 10/1987 | Bajusz et al. | 514/18 |
| 5,187,157 | 2/1993 | Kettner et al. | 514/18 |
| 5,260,307 | 11/1993 | Ackermann et al. | 514/323 |
| 5,405,854 | 4/1995 | Ackermann et al. | 514/315 |
| 5,510,369 | 4/1996 | Lumma et al. | 514/422 |
| 5,559,232 | 9/1996 | Ackermann et al. | 544/121 |
| 5,561,146 | 10/1996 | Kim et al. | 514/326 |
| 5,583,146 | 12/1996 | Kimball et al. | 514/326 |
| 5,602,253 | 2/1997 | Antonsson et al. | 544/330 |
| 5,614,499 | 3/1997 | Bylund et al. | 514/19 |
| 5,629,324 | 5/1997 | Vacca et al. | 514/316 |
| 5,705,487 | 1/1998 | Schacht et al. | 514/19 |
| 5,707,966 | 1/1998 | Schacht et al. | 514/19 |
| 5,710,130 | 1/1998 | Schacht et al. | 514/19 |
| 5,723,444 | 3/1998 | Antonsson et al. | 514/19 |
| 5,726,159 | 3/1998 | Schacht et al. | 514/19 |
| 5,736,521 | 4/1998 | Bylund et al. | 514/19 |
| 5,741,792 | 4/1998 | Kimball et al. | 514/237.2 |
| 5,741,799 | 4/1998 | Kimball et al. | 514/316 |
| 5,744,487 | 4/1998 | Ohshima et al. | 514/326 |
| 5,747,460 | 5/1998 | Bylund et al. | 514/19 |
| 5,780,631 | 7/1998 | Antonsson et al. | 546/1 |
| 5,783,563 | 7/1998 | Antonsson et al. | 514/19 |
| 5,852,051 | 12/1998 | Bohm et al. | 549/423 |
| 5,856,307 | 1/1999 | Antonsson et al. | 514/18 |
| 5,914,319 | 6/1999 | Schacht et al. | 514/19 |
| 5,932,637 | 8/1999 | Ito et al. | 523/451 |
| 5,939,392 | 8/1999 | Antonsson et al. | 514/18 |
| 5,955,433 | 9/1999 | Bylund et al. | 514/19 |
| 5,965,692 | 10/1999 | Gustafsson et al. | 530/300 |
| 6,030,972 | 2/2000 | Bohm et al. | 514/257 |

FOREIGN PATENT DOCUMENTS

| | | |
|---|---|---|
| 185 390 | 6/1986 | (EP) . |
| 195 212 | 9/1986 | (EP) . |
| 293 881 | 12/1988 | (EP) . |
| 362 002 | 4/1990 | (EP) . |
| 364 344 | 4/1990 | (EP) . |
| 468 231 A2 | 1/1992 | (EP) . |
| 526 877 | 2/1993 | (EP) . |
| 530 167 | 3/1993 | (EP) . |
| 542 525 | 5/1993 | (EP) . |
| 559 046 | 9/1993 | (EP) . |
| 601 459 | 6/1994 | (EP) . |
| 623 596 | 11/1994 | (EP) . |
| 641 779 | 3/1995 | (EP) . |
| 648 780 | 4/1995 | (EP) . |
| 669 317 | 8/1995 | (EP) . |
| 672658 * | 9/1995 | (EP) . |
| 672 658 | 9/1995 | (EP) . |
| 686 642 | 12/1995 | (EP) . |
| 93/11152 | 6/1993 | (WO) . |
| 93/18060 | 9/1993 | (WO) . |
| 94/29336 | 12/1994 | (WO) . |
| 95/23609 | 8/1995 | (WO) . |
| 95/35309 | 12/1995 | (WO) . |
| 96/03374 | 2/1996 | (WO) . |
| 96/17860 | 6/1996 | (WO) . |
| 96/24609 | 8/1996 | (WO) . |
| 96/25426 | 8/1996 | (WO) . |
| 96/31504 | 10/1996 | (WO) . |
| 96/32110 | 10/1996 | (WO) . |
| 97/02284 | 1/1997 | (WO) . |
| 97/23499 | 7/1997 | (WO) . |
| 97/33576 | 9/1997 | (WO) . |
| 97/46577 | 12/1997 | (WO) . |
| 98/01422 | 1/1998 | (WO) . |
| 98/06740 | 2/1998 | (WO) . |
| 98/06741 | 2/1998 | (WO) . |

* cited by examiner

Primary Examiner—Richard L. Raymond
Assistant Examiner—Deepak R. Rao
(74) Attorney, Agent, or Firm—Nixon & Vanderhye

(57) ABSTRACT

There is provided compounds of formula I,

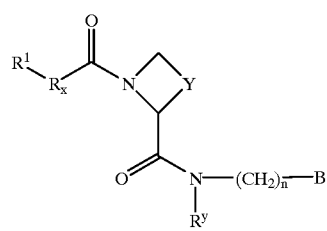

I wherein $R^1$, $R_x$, Y, $R^y$, n and B have meanings given in the description which are useful as competitive inhibitors of trypsin-like proteases, such as thrombin, and in particular in the treatment of conditions where inhibition of thrombin is required (e.g. thrombosis) or as anticoagulants.

18 Claims, No Drawings

AMIDINO DERIVATIVES AND THEIR USE AS THROMBIN INHIBITORS

This application is a 371 of PCT/SE98/01103 filed Jun. 9, 1998.

FIELD OF THE INVENTION

This invention relates to novel pharmaceutically useful compounds, in particular competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position; European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609 and WO 96/25426.

However, there remains a need for effective inhibitors of trypsin-like serine proteases, such as thrombin. There is a particular need for compounds which are both orally bioavailable and selective in inhibiting thrombin over other serine proteases. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

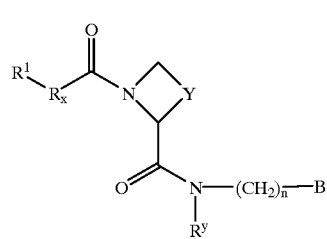

wherein
R$^1$ represents H, C$_{1-4}$ alkyl (optionally substituted by one or more substituents selected from cyano, halo, OH, C(O)OR$^{1a}$ or C(O)N(R$^{1b}$)R$^{1c}$) or OR$^{1d}$;
R$^{1d}$ represents H, C(O)R$^{11}$, SiR$^{12}$R$^{13}$R$^{14}$ or C$_{1-6}$ alkyl, which latter group is optionally substituted or terminated by one or more substituent selected from OR$^{15}$ or (CH$_2$)$_q$R$^{16}$;
R$^{12}$, R$^{13}$ and R$^{14}$ independently represent H, phenyl or C$_{1-6}$ alkyl;
R$^{16}$ represents C$_{1-4}$ alkyl, phenyl, OH, C(O)OR$^{17}$ or C(O)N(H)R$^{18}$;
R$^{18}$ represents H, C$_{1-4}$ alkyl or CH$_2$C(O)OR$^{19}$;
R$^{15}$ and R$^{17}$ independently represent H, C$_{1-6}$ alkyl or C$_{1-3}$ alkylphenyl;
R$^{1a}$, R$^{1b}$, R$^{1c}$, R$^{11}$ and R$^{19}$ independently represent H or C$_{1-4}$ alkyl; and q represents 0, 1 or 2;

$R_x$ represents a structural fragment of formula IIa, IIb or IIc,

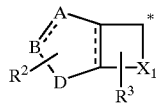

IIa

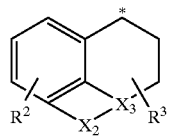

IIb

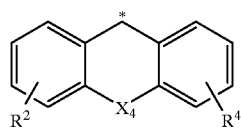

IIc wherein the dotted lines independently represent optional bonds;

A and B independently represent O or S, CH or $CH_2$ (as appropriate), or N or $N(R^{21})$ (as appropriate);

D represents —$CH_2$—, O, S, $N(R^{22})$, —$(CH_2)_2$—, —CH=CH—, —$CH_2N(R^{22})$—, —$N(R^{22})CH_2$—, —CH=N—, —N=CH—, —$CH_2O$—, —$OCH_2$—, —$CH_2S$— or —$SCH_2$—;

$X_1$ represents $C_{2-4}$ alkylene; $C_{2-3}$ alkylene interrupted by Z; —C(O)—Z—$A^1$; —Z—C(O)—$A^1$; —$CH_2$—C(O)—$A^1$; —Z—C(O)—Z—$A^2$—; —$CH_2$—Z—C(O)—$A^2$—; —Z—$CH_2$—C(O)—$A^2$—; —Z—$CH_2$—S(O)$_m$—$A^2$—; —$CH_2$—Z—S(O)$_m$—$A^2$—; —C(O)—$A^3$; —Z—$A^3$; or —$A^3$—Z—;

$X_2$ represents $C_{2-3}$ alkylene, —C(O)—$A^4$— or —$A^4$—C(O)—;

$X_3$ represents CH or N;

$X_4$ represents a single bond, O, S, C(O), $N(R^{23})$, —CH($R^{23}$)—, —CH($R^{23}$)—CH($R^{24}$)— or —C($R^{23}$)=C($R^{24}$)—;

$A^1$ represents a single bond or $C_{1-2}$ alkylene;

$A^2$ represents a single bond or —$CH_2$—;

$A^3$ represents $C_{1-3}$ alkylene;

$A^4$ represents C(O) or $C_{1-2}$ alkylene;

Z represents, at each occurrence, O, S(O)$_m$ or $N(R^{25})$;

m represents, at each occurrence, 0, 1 or 2;

$R^2$ and $R^4$ independently represent one or more optional substituents selected from $C_{1-4}$ alkyl (which latter group is optionally substituted by one or more halo substituent), $C_{1-4}$ alkoxy, methylenedioxy, halo, hydroxy, cyano, nitro, $SO_2NH_2$, C(O)O$R^{26}$ or $N(R^{27})R^{28}$);

$R^3$ represents an optional substituent selected from OH or $C_{1-4}$ alkoxy;

$R^{21}$, $R^{22}$, $R^{23}$, $R^{24}$, $R^{25}$, $R^{26}$, $R^{27}$ and $R^{28}$ independently represent H or $C_{1-4}$ alkyl;

Y represents $CH_2$, $(CH_2)_2$, CH=CH, $(CH_2)_3$, $CH_2CH$=CH or CH=$CHCH_2$, which latter three groups are optionally substituted by $C_{1-4}$ alkyl, methylene, oxo or hydroxy;

$R^y$ represents H or $C_{1-4}$ alkyl;

n represents 0, 1, 2, 3 or 4; and

B represents a structural fragment of formula IIIa, IIIb or IIIc

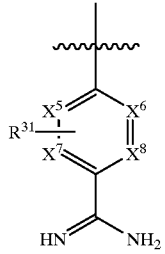

IIIa

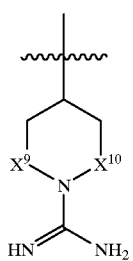

IIIb

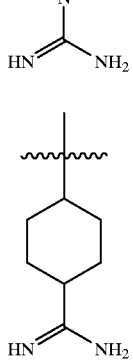

IIIc wherein $X^5$, $X^6$, $X^7$ and $X^8$ independently represent CH, N or N—O;

$X^9$ and $X^{10}$ independently represent a single bond or $CH_2$; and $R^{31}$ represents an optional substituent selected from halo and $C_{1-4}$ alkyl;

or a pharmaceutically acceptable salt thereof;

provided that:

(a) A and B do not both represent O or S;

(b) B and D do not both represent O or S;

(c) when $R^1$ represents $OR^{1d}$ and $X_1$ represents —C(O)—Z—$A^1$, —Z—$CH_2$—S(O)$_m$—$A^2$—, —$CH_2$—Z—S(O)$_m$—$A^2$— or —Z—C(O)—Z—$A^2$, then $A^1$ or $A^2$ (as appropriate) do not represent a single bond; and (d) when $X_4$ represents —CH($R^{23}$)—, $R^1$ does not represent OH.

The compounds of formula I may exhibit tautomerism. All tautomeric forms and mixtures thereof are included within the scope of the invention. Further it will be appreciated by those skilled in the art that, in the structural fragment of formula IIa, the optional double bonds, may, in conjunction with certain identities of substituent D, render the ring bearing A, B and D aromatic in character.

The compounds of formula I may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Alkyl groups which $R^1$, $R^{1a}$, $R^{1b}$, $R^{1c}$, $R^{1d}$, $R^2$, $R^4$, $R^{11}$, $R^{12}$, $R^{13}$, $R^{14}$, $R^{15}$, $R^{16}$, $R^{17}$, $R^{18}$, $R^{19}$, $R^{21}$, $R^{22}$, $R^{23}$, $R^{24}$, $R^{25}$, $R^{26}$, $R^{27}$, $R^{28}$, $R^{31}$ and $R^y$ may represent, and with which Y may be substituted; the alkyl part of alkylphenyl groups which $R^{15}$ and $R^{17}$ may represent; and alkoxy groups which $R^2$, $R^3$ and $R^4$ may represent, may, when there is a sufficient number of carbon atoms, be linear or branched, saturated or unsaturated, cyclic or acyclic. Alkylene groups which $X_1$, $X_2$, $A^1$, $A^3$ and $A^4$ may represent may, when there is a sufficient number of carbon atoms, be linear or branched, saturated or unsaturated.

Halo groups, which $R^{31}$ may represent, and with which $R^1$, $R^2$ and $R^4$ may be substituted, include fluoro, chloro, bromo and iodo.

In the structural fragments of formulae IIa, IIb and IIc, the dots indicate the carbon atom which is bonded to the —C(O)— group and to $R^1$ in a compound of formula I (for the avoidance of doubt, there is no further H atom bonded to the carbon atom so indicated).

The wavy lines on the bond in the fragments of formulae IIIa, IIIb and IIIc signify the bond position of the fragment.

According to a further aspect of the invention there is provided a compound of formula I as hereinbefore defined with the additional provisos that:
  $R^y$ represents H;
  $R^{28}$ represents H;
  $X_4$ does not represent —CH($R^{23}$)—.

According to a further aspect of the invention there is provided a compound of formula I as hereinbefore defined with the additional provisos that:
  $R^y$ represents $C_{1-4}$ alkyl;
  $R^{28}$ represents $C_{1-4}$ alkyl;
  $X_4$ represents —CH($R^{23}$)—.

Abbreviations are listed at the end of this specification.

When n represents 2 and B represents a structural fragment of formula IIIb, preferred compounds of formula I include those wherein $X^9$ and $X^{10}$ do not both represent $CH_2$.

Preferred compounds of formula I include those wherein:
  $R^1$ represents OH or $C_{1-4}$ alkyl (which latter group is optionally substituted by cyano or OH);
  $R_x$ represents a structural fragment of formula IIa;
  when $R_x$ represents a structural fragment of formula IIa, the dotted lines represent bonds, A and B both represent CH and D represents —CH=CH—;
  when $R_x$ represents a structural fragment of formula IIa, $X_1$ represents $C_2$— or $C_3$-alkylene, —OCH$_2$— or —O(CH$_2$)$_2$—;
  Y represents $CH_2$, $(CH_2)_2$ or $(CH_2)_3$;
  B represents a structural fragment of formula IIIa in which $X^5$, $X^6$, $X^7$ and $X^8$ all represents CH.

More preferred compounds of the invention include those wherein, when $R_x$ represents a structural fragment of formula IIa, $X_1$ represents $C_3$-alkylene or —O(CH$_2$)$_2$—.

When $R_x$ represents a structural fragment of formula IIa, and $R^2$ represents at least one substituent, a preferred point of substitution is at the carbon atom which is at position B.

When $R_x$ represents a structural fragment of formula IIa, the dotted lines represent bonds, A and B both represent CH and D represents —CH=CH— (i.e. the ring bearing $R^2$ is a benzo group), and $R^2$ represents at least one substituent, the ring is preferably substituted either at the carbon atom in the —CH=CH— group (position D) which is adjacent to the ring junction, or, more preferably, at the carbon atom which is at position B, or at both of these sites. For example, when the fragment IIa represents a tetralin-1-yl group (i.e. the dotted lines represent bonds, A and B both represent CH, D represents —CH=CH— and $X_1$ represents saturated $C_3$-alkylene), preferred substitution positions are at the 5- or, especially, at the 7-position, or at both of these positions. Correspondingly, when the fragment IIa represents a chroman-4-yl group (i.e. the dotted lines represent bonds, A and B both represent CH, D represents —CH=CH— and $X_1$ represents —O(CH$_2$)$_2$—), preferred substitution positions are at the 8- or, especially, at the 6-position, or at both of these positions.

Compounds of formula I in which the fragment

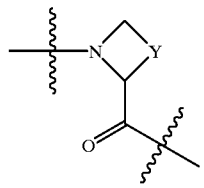

is in the S-configuration are preferred. The wavy lines on the bonds in the above fragment signify the bond position of the fragment.

Preferred compounds of formula I include the compounds of the Examples described hereinafter.

PREPARATION

According to the invention there is also provided a process for the preparation of compounds of formula I which comprises:

(i) the coupling of a compound of formula IV,

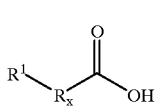

IV wherein $R^1$ and $R_x$ are as hereinbefore defined with a compound of formula V,

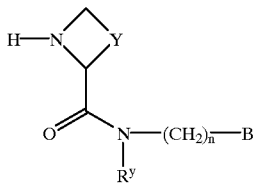

V wherein $R^y$, Y, n and B are as hereinbefore defined; or (ii) the coupling of a compound of formula VI,

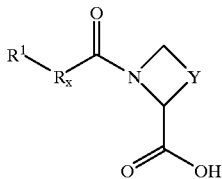

VI wherein $R^1$, $R_x$ and Y are as hereinbefore defined with a compound of formula VII,

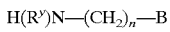

H(R$^y$)N—(CH$_2$)$_n$—B    VII wherein $R^y$, n and B are as hereinbefore defined,
for example in the presence of a coupling agent (e.g. oxalyl chloride in DMF, EDC, DCC, HBTU, HATU or TBTU), an appropriate base (e.g. pyridine, 2,4,6,-trimethylpyridine, DMAP, TEA or DIPEA) and a suitable organic solvent (e.g. dichloromethane, acetonitrile or DMF).

Compounds of formula IV are commercially available, are well known in the literature, or are available using known and/or standard techniques.

For example, compounds of formula IV in which $R^1$ represents OH may be prepared by reaction of a compound of formula VIII, $R_x$=O    VIII wherein $R_x$ is as hereinbefore defined, with:

(a) KCN, for example at 20° C. in the presence of sodium bisulphite in water, followed by hydrolysis in the presence of aqueous acid (e.g. HCl), for example at 20° C. in the presence of a suitable solvent (e.g. alcohol and/or water);

(b) CHCl$_3$, in the presence of aqueous base (e.g. NaOH);

(c) TMSCN, for example at 20° C. in the presence of a suitable organic solvent (e.g. CH$_2$Cl$_2$), followed by hydrolysis in the presence of acid (e.g. HCl or H$_2$SO$_4$), for example at 20° C. (e.g. according, or analogously, to the method described by Bigge et al in J. Med. Chem. (1993) 36, 1977), followed by alkaline hydrolysis to give the free acid.

Compounds of formula IV in which $R^1$ represents H may be prepared from corresponding compounds of formula IV in which $R^1$ represents OH (or a lower alkyl ester of the acid), for example by elimination of water, followed by hydrogenation of the resultant alkene using techniques which are well known to those skilled in the art, followed by, if necessary, hydrolysis to give the free acid.

Compounds of formula IV in which $R^1$ represents $C_{1-4}$ alkyl may be prepared from corresponding compounds of formula IV in which $R^1$ represents H (or a lower alkyl ester of the acid), for example by reaction with an appropriate alkyl halide using techniques which are well known to those skilled in the art, followed by, if necessary, hydrolysis to give the free acid.

Compounds of formula IV in which $R^1$ represents $OR^{1d}$ and $R^{1d}$ represents $C(O)R^{11}$, $SiR^{12}R^{13}R^{14}$ or $C_{1-6}$ alkyl may be prepared by acylation, silylation or alkylation (as appropriate) of a corresponding compound of formula IV in which $R^1$ represents OH (or a lower alkyl ester of the acid) under conditions which are well known to those skilled in the art, followed by, if necessary, hydrolysis to give the free acid.

Compounds of formula V may be prepared by reaction of a compound of formula IX

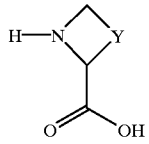

IX wherein Y is as hereinbefore defined with a compound of formula VII as hereinbefore defined, for example under conditions such as those described hereinbefore for synthesis of compounds of formula I.

Compounds of formulae V and VII in which $R^y$ represents $C_{1-4}$ alkyl may be prepared by reaction of a corresponding compound of formula V or formula VII, as appropriate, in which $R^y$ represents H with a compound of formula IXa, R$^y$Hal    IXa wherein Hal represents halo (e.g. Cl, Br or I) and $R^y$ is as hereinbefore defined, for example under conditions which are well known to those skilled in the art.

Compounds of formula VI are readily available using known techniques. For example, compounds of formula VI may be prepared by reaction of a compound of formula IV as hereinbefore defined with a compound of formula IX as hereinbefore defined, for example under conditions such as those described hereinbefore for synthesis of compounds of formula I.

Compounds of formula VIII are commercially available, are well known in the literature, or may be prepared in accordance with known techniques. For example compounds of formula VIII may be prepared as follows:

(a) Compounds of formula VIII in which $R_x$ represents a structural fragment of formula IIa, in which the dotted lines represent bonds, A and B both represent CH and D represents —CH=CH—; $X_1$ represents $C_{2-4}$ alkylene, —Z—A$^3$— or —C(O)—A$^3$—, in which A$^3$ is as hereinbefore defined; and $R^3$ is absent, may be prepared by cyclisation of a compound of formula X,

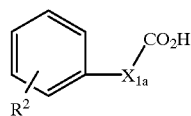

X wherein $X_{1a}$ represents $C_{2-4}$ alkylene, —Z—A$^3$— or —C(O)—A$^3$—, and Z, A$^3$ and $R^2$ are as hereinbefore defined, using an appropriate acylating agent. for example at 100° C. in the presence of polyphosphoric acid or using PCl$_5$ at reflux followed by AlCl$_3$. Compounds of formula X in which $X_{1a}$ represents $C_3$-alkylene or —C(O)—A$^3$—, in which A$^3$ represents $C_2$-alkylene, may be prepared in accordance with known techniques, for example by reaction of succinic anhydride with the corresponding phenyl lithium and, for compounds of formula X in which $X_{1a}$ represents $C_3$-alkylene, selective reduction of the resultant ketone, under conditions which are well known to those skilled in the art. Compounds of formula X in which $X_{1a}$ represents —Z—A$^3$— and A$^3$ represents $C_{2-3}$ alkylene may be prepared as described hereinafter.

(b) Compounds of formula VIII in which $R_x$ represents a structural fragment of formula IIa, in which the dotted lines represent bonds, A and B both represent CH and D represents —CH=CH—; $X_1$ represents $C_{2-4}$ alkylene or —C(O)—$A^3$—, in which $A^3$ is as hereinbefore defined; and $R^3$ is absent, may alternatively be prepared by cyclisation of a compound of formula XI,

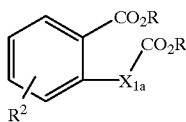

XI wherein R represents $C_{1-6}$ alkyl and $X_{1a}$ and $R^2$ are as hereinbefore defined, for example at 20° C. in the presence of a suitable base (e.g. an alkali metal alkoxide) and an appropriate organic solvent (e.g. lower alkyl alcohol) followed by hydrolysis and decarboxylation. Compounds of formula XI may be prepared in accordance with known techniques. For example, compounds of formula XI in which $X_{1a}$ represents $C_3$-alkylene or —C(O)—$A^3$— in which $A^3$ represents $C_2$-alkylene may be prepared by reaction of succinic anhydride with a compound of formula XII,

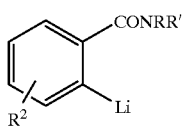

XII wherein R' represents $C_{1-6}$ alkyl and R and $R^2$ are as hereinbefore defined and, for compounds of formula XI in which $X_{1a}$ represents $C_3$-alkylene, selective reduction of the resultant ketone, followed by functional group transformations of the amide and the acid to ester groups, under conditions which are well known to those skilled in the art.

(c) Compounds of formula VIII in which $R_x$ represents a structural fragment of formula IIa, in which the dotted lines represent bonds, A and B both represent CH and D represents —CH=CH—; $X_1$ represents —Z—$A^3$— in which $A^3$ represents $C_2$ alkylene and Z represents O or S; and $R^3$ is absent, may be prepared by cyclisation of a compound of formula XIII,

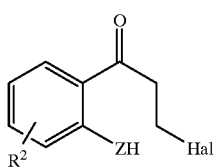

XIII wherein Hal and $R^2$ are as hereinbefore defined, for example at 20° C. in the presence of aqueous-ethanolic NaOH. For corresponding compounds of formula VIII in which $X_1$ represents —Z—$A^3$— and Z represents $S(O)_m$ in which m is 1 or 2, this abovementioned cyclisation should be followed by carrying out an oxidation reaction on the cyclised product comprising an S atom, for example using m-chloroperbenzoic acid.

(d) Compounds of formula VIII in which $R_x$ represents a structural fragment of formula IIa, in which the dotted lines represent bonds, A and B both represent CH and D represents —CH=CH—; $X_1$ represents —Z—$A^3$— in which $A^3$ represents $C_2$-alkylene or —Z—C(O)—$A^1$ in which $A^1$ represents $C_1$-alkylene; and $R^3$ is absent, may be prepared by reaction of a compound of formula XIV,

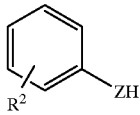

XIV wherein $R^2$ and Z are as hereinbefore defined, with either:

(1) for compounds of formula VIII in which $X_1$ represents —Z—$A^3$— in which $A^3$ represents $C_2$-alkylene, a compound of formula XV,

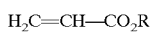

$H_2C=CH—CO_2R$  XV wherein R is as hereinbefore defined, for example at 20° C. in the presence of a suitable base (e.g. triethylamine or sodium ethoxide) and an appropriate organic solvent (e.g. ethanol or DMF); or (2) a compound of formula XVI,

$L^1$—G—$CH_2$—$CO_2R$  XVI wherein $L^1$ represents a suitable leaving group (such as Cl, Br, I, mesylate or tosylate), G represents $CH_2$ or C(O) and R is as hereinbefore defined, for example at 20° C. in the presence of a suitable base (e.g. triethylamine) and an appropriate organic solvent (e.g. THF); followed by cyclisation under appropriate conditions (e.g. those described hereinbefore).

(e) Compounds of formula VIII in which $R_x$ represents a structural fragment of formula IIa, in which the ring bearing A, B and D is a carbocyclic aromatic, or heterocyclic aromatic, ring as defined hereinbefore in respect of compounds of formula I; $X_1$ represents —$CH_2$—Z—$C_{1-2}$ alkylene-, in which Z is as hereinbefore defined; and $R^3$ is absent, may be prepared by reaction of a compound of formula XVII,

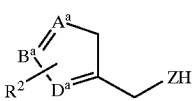

XVII wherein the ring bearing $A^a$, $B^a$ and $D^a$ is a carbocyclic aromatic, or heterocyclic aromatic, ring as defined hereinbefore in respect of compounds of formula I, and Z and $R^2$ are as hereinbefore defined, with a compound of formula XVIII,

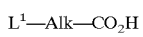

$L^1$—Alk—$CO_2H$  XVIII wherein Alk represents $C_{1-2}$ alkylene and $L^1$ is as hereinbefore defined, for example at 20° C. in the presence of a suitable base (e.g. sodium methoxide) and an appropriate organic solvent (e.g. THF).

(f) Compounds of formula VIII in which $R_x$ represents a structural fragment of formulae IIb, IIc or IIa, in which latter case the ring bearing A, B and D is a carbocyclic aromatic, or heterocyclic aromatic, ring as defined hereinbefore in respect of compounds of formula I; and, in the cases when $R_x$ represents a structural fragment of formulae IIa or IIb, $R^3$ is absent, may be prepared by cyclisation of a compound of formula XX,

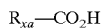   XX wherein $R_{xa}$ represents a structural fragment of formula XXa, XXb or XXc

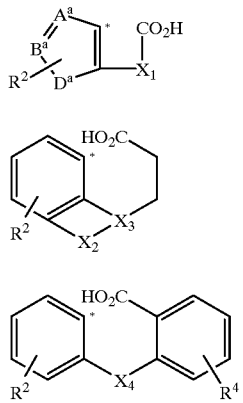

wherein, in XXa, the ring bearing $A^1$, $B^a$ and $D^a$ is a carbocyclic aromatic, or heterocyclic aromatic, ring as defined hereinbefore in respect of compounds of formula I, and $R^2$, $R^4$, $X_1$, $X_2$, $X_3$ and $X_4$ are as hereinbefore defined, in the presence of polyphosphoric acid, for example at 100° C. The dots adjacent to the carbon atoms in fragments of formula XXa, XXb and XXc signify the point of attachment of the fragments to the $CO_2H$ group of the compound of formula XX. Compounds of formula XX may be prepared by hydrolysis of a corresponding compound of formula XXI,

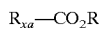   XXI wherein $R_{xa}$ and R are as hereinbefore defined (and in which the $CO_2H$ in the fragments of formulae XXa, XXb and XXc in $R_{xa}$ may also be replaced by $CO_2R$), for example under reaction conditions which are well known to those skilled in the art.

(g) Compounds of formula VIII in which $R_x$ represents a structural fragment of formula IIa in which the ring bearing A, B and D is a carbocyclic aromatic, or heterocyclic aromatic, ring as defined hereinbefore in respect of compounds of formula I; $X_1$ represents —O—$CH_2$—; and $R^3$ is absent, may be prepared by reaction of a compound of formula XXII,

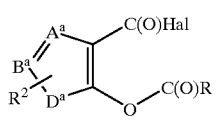   XXII wherein the ring bearing $A^a$, $B^a$ and $D^a$ is a carbocyclic aromatic, or heterocyclic aromatic, ring as defined hereinbefore in respect of compounds of formula I, and $R^2$, Hal and R are as hereinbefore defined, with diazomethane, for example at 20° C. in the presence of a suitable organic solvent (e.g. diethyl ether).

(h) Compounds of formula VIII in which $R_x$ represents a structural fragment of formula IIa, in which the dotted lines represent bonds, A and B both represent CH and D represents —CH=CH—; $X_1$ represents —C(O)—O—$CH_2$—; and $R^3$ is absent, may be prepared by cyclisation of a compound of formula XXIII,

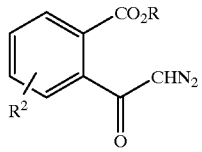   XXIII wherein $R^2$ and R are as hereinbefore defined, for example at −20° C. in the presence of sulphuric acid and an appropriate organic solvent (e.g. methanol). Compounds of formula XXIII may be prepared by reacting a corresponding acid halide with diazomethane, for example at 20° C. in the presence of a suitable organic solvent (e.g. diethyl ether).

(i) Compounds of formula VIII in which $R_x$ represents a structural fragment of formula IIa or IIc in which $X_1$ includes $N(R^{25})$, or $X_4$ represent $N(R^{23})$, (as appropriate), and $R^{23}$ and $R^{25}$ (as appropriate) represent $C_{1-4}$ alkyl may be prepared by reaction of a corresponding compound of formula VIII in which $X_1$ includes, or $X_4$ represents, (as appropriate) NH with a compound of formula XXV

   XXV wherein $R^a$ represents $C_{1-4}$ alkyl and Hal is as hereinbefore defined, for example under conditions which are well known to those skilled in the art.

(j) Compounds of formula VIII in which $R_x$ represents a structural fragment of formula IIa, in which the dotted lines represent bonds, A and B both represent CH and D represents —CH=CH—; $X_1$ represents —C(O)—N(H)—$CH_2$—; and $R^3$ is absent, may be prepared by catalytic hydrogenation of an hydroxamic acid of formula XXVI,

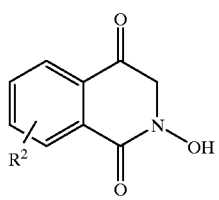   XXVI wherein $R^2$ is as hereinbefore defined, using an appropriate catalyst system (e.g. Pd/C) in the presence of a suitable organic solvent (e.g. methanol). Compounds of formula XXVI may be prepared by cyclisation of a corresponding compound of formula XXVII,

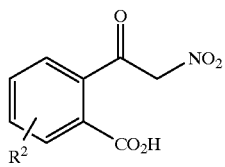   XXVII wherein $R^2$ is as hereinbefore defined, for example at 20° C. in the presence of fuming HCl and tin dichloride.

(k) Selective oxidation of a compound of formula XXX,

    XXX wherein $R_x$ is as hereinbefore defined, for example in the presence of a suitable oxidising agent (e.g. $CrO_3$ or $KMnO_4$) and an appropriate solvent (e.g. water).

(l) Selective oxidation of a compound of formula XXXI,

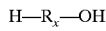    XXXI wherein $R_x$ is as hereinbefore defined, for example in the presence of a suitable oxidising agent (e.g. $MnO_2$) in an appropriate organic solvent (e.g. $CH_2Cl_2$).

(m) Hydrolysis of an oxime formula XXXII,

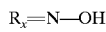    XXXII wherein $R_x$ is as hereinbefore defined, for example by heating in the presence of acid (e.g. HCl) and an appropriate organic solvent. Compounds of formula XXXII may be prepared by reaction of a corresponding compound of formula XXX, as hereinbefore defined, with propyl nitrite, for example in the presence of HCl in ethanol.

(n) Compounds of formula VIII in which $R_x$ represents a structural fragment of formula IIa and $X_1$ represents —$CH_2$—CH=CH—, may be prepared by elimination of a compound of formula XXXIII,

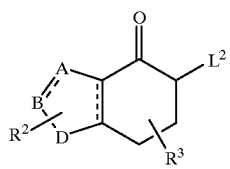    XXXIII wherein $L^2$ represents a suitable leaving group (e.g. Br or SePh) and the dotted lines, A, B, D, $R^2$ and $R^3$ are as hereinbefore defined, under appropriate reaction conditions, for example in the presence of aqueous ethanolic NaOH or hydrogen peroxide, and an appropriate organic solvent (e.g. THF).

(o) Compounds of formula VIII in which $R_x$ represents a structural fragment of formula IIb, $X_2$ represents —C(O)—$A^4$— and $A^4$ is as hereinbefore defined, may be prepared by cyclisation of a compound of formula XXXIV,

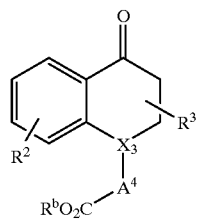    XXXIV wherein $R^b$ represents H, $C_{1-6}$ alkyl or Hal and $R^2$, $R^3$, $A^4$, $X_3$ and Hal are as hereinbefore defined, for example in the presence of polyphosphoric acid, as described hereinbefore or, in the case where $R^b$ represents Hal, in the presence of $AlCl_3$ in nitromethane at, for example, 20° C.

(p) Compounds of formula VIII in which $R_x$ represents a structural fragment of formula IIb and $X_2$ represents —$A^4$—C(O)— and $A^4$ represents $C_{1-2}$ alkylene may be prepared by cyclisation of a compound of formula XXXV,

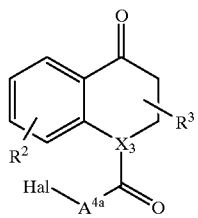    XXXV wherein $A^{4a}$ represents $C_{1-2}$ alkylene and Hal, $R^2$, $R^3$ and $X_3$ are as hereinbefore defined.

Compounds of formulae VII, IX, IXa, XII, XIII, XIV, XV, XVI, XVII, XVIII, XXI, XXII, XXV, XXVII, XXX, XXXI, XXXIII, XXIV and XXV are either commercially available, are well known in the literature, or are available using known techniques, including techniques which are the same as, or analogous to, those described herein.

Substituents on the aromatic and/or non-aromatic, carbocyclic and/or heterocyclic ring(s) in compounds of formulae I, IV, V, VI, VII, VIII, X, XI, XII, XIII, XIV, XVII, XX, XXI, XXII, XXIII, XXVI, XXVII, XXX, XXXI, XXXII, XXXIII, XXXIV and XXV may be interconverted using techniques well known to those skilled in the art. For example, nitro may be reduced to amino, hydroxy may be alkylated to give alkoxy, alkoxy may be hydrolysed to hydroxy, alkenes may be hydrogenated to alkanes, halo may be hydrogenated to H, etc.

The compounds of formula I may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino, amidino and guanidino include t-butyloxycarbonyl, benzyloxycarbonyl or 2-trimethylsilylethoxycarbonyl (Teoc). Amidino and guanidino nitrogens may also be protected by hydroxy or alkoxy groups, and may be either mono- or diprotected.

The protection and deprotection of functional groups may take place before or after coupling, or before or after any other reaction in the abovementioned schemes.

In particular, the compounds of formula I may be prepared by processes comprising the coupling of an N-acylated amino acid or a N-protected amino acid. When a N-protected amino acid is used, the acyl group may be introduced after coupling. Deprotection of the nitrogen atom may then be effected using standard methods.

Protecting groups may be removed in accordance with techniques which are well known to those skilled in the art and as described hereinafter.

Certain protected derivatives (which may also be referred to as "intermediates") of compounds of formula I, which may be made prior to a final deprotection stage to form compounds of formula I, are novel.

According to a further aspect of the invention there is provided a compound of formula Ia, Ia

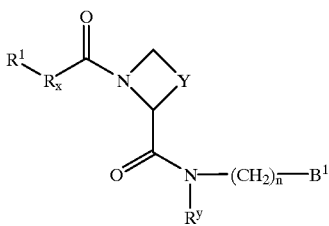

wherein B¹ represents a structural fragment of formula IIId, IIIe or IIIf

IIId

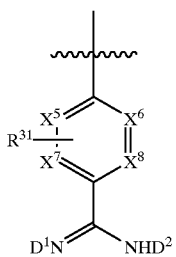

IIIe

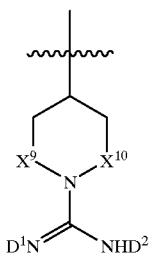

IIIf

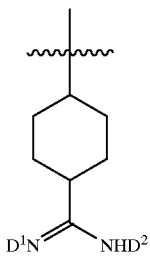

wherein $D^1$ and $D^2$ independently represent H, OH, $OR^a$, $OC(O)R^b$, $OC(O)OR^c$, $C(O)OR^d$, $C(O)R^e$; in which $R^a$ represents phenyl, benzyl, $C_{1-7}$ alkyl (which latter group is optionally interrupted by oxygen or is optionally substituted by halo) or —$C(R^f)(R^g)$—$OC(O)R^h$;

$R^b$ represents $C_{1-17}$ alkyl (which latter group is optionally substituted by $C_{1-6}$ alkoxy, $C_{1-6}$ acyloxy, amino or halo); $C_{1-6}$ alkoxy, $C_{3-7}$ cycloalkyl, phenyl, naphthyl or $C_{1-3}$ alkylphenyl (which latter five groups are optionally substituted by $C_{1-6}$ alkyl or halo); or —$[C(R^i)(R^j)]_m OC(O)R^k$;

$R^c$ represents $C_{1-17}$ alkyl, phenyl, 2-naphthyl (which latter three groups are optionally substituted by $C_{1-6}$ alkyl, $Si(R^{aa})(R^{ab})(R^{ac})$ or halo), —$[C(R^m)(R^n)]_n OC(O)R^p$, or —$CH_2$—$Ar^1$;

$R^d$ represents 2-naphthyl, phenyl, $C_{1-3}$ alkylphenyl (which latter three groups are optionally substituted by $C_{1-6}$ alkyl, $C_{1-6}$ alkoxy, nitro, $Si(R^{ba})(R^{bb})(R^{bc})$ or halo), $C_{1-2}$ alkyl (which latter group is optionally substituted by $C_{1-6}$ alkoxy, $C_{1-6}$ acyloxy or halo), —$[C(R^q)(R^r)]_p OC(O)R^s$ or —$CH_2$—$Ar^2$;

$R^e$ represents phenyl, benzyl, $C_{1-6}$ alkyl (which latter group is optionally interrupted by oxygen) or —$[C(R^t)(R^u)]_r OC(O)R^v$;

$R^{aa}$, $R^{ab}$, $R^{ac}$, $R^{ba}$, $R^{bb}$ and $R^{bc}$ independently represent $C_{1-6}$ alkyl or phenyl;

$R^f$, $R^g$, $R^i$, $R^j$, $R^m$, $R^n$, $R^q$, $R^r$, $R^t$ and $R^u$ independently represent H or $C_{1-6}$ alkyl;

$R^h$, $R^k$, $R^p$, $R^s$ and $R^v$ independently represent $C_{1-17}$ alkyl (which latter group is optionally substituted by $C_{1-6}$ alkoxy, $C_{1-6}$ acyloxy or halo); $C_{1-6}$ alkoxy, $C_{3-7}$ cycloalkyl, phenyl, naphthyl or $C_{1-3}$ alkylphenyl (which latter five groups are optionally substituted by $C_{1-6}$ alkyl or halo);

$Ar^1$ and $Ar^2$ independently represent the structural fragment

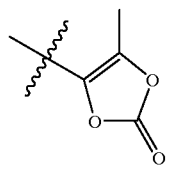

m and r independently represent 3 or 4;
n and p independently represent 1, 2 or 3; and
$R^1$, $R_x$, Y, $R^y$, n, $X^5$, $X^6$, $X^7$, $X^8$, $X^9$, $X^{10}$ and $R^{31}$ are as hereinbefore defined;
or a pharmaceutically acceptable salt thereof;
provided that $D^1$ and $D^2$ do not both represent H.

Alkyl groups which $R^a$, $R^{aa}$, $R^{ab}$, $R^{ac}$, $R^b$, $R^{ba}$, $R^{bb}$, $R^{bc}$, $R^c$, $R^d$, $R^e$, $R^f$, $R^g$, $R^h$, $R^i$, $R^j$, $R^k$, $R^m$, $R^n$, $R^p$, $R^q$, $R^r$, $R^s$, $R^t$, $R^u$ and $R^v$ may represent and with which $R^b$, $R^c$, $R^d$, $R^h$, $R^k$, $R^p$, $R^s$ and $R^v$ may be substituted; cycloalkyl groups which $R^b$, $R^h$, $R^k$, $R^p$, $R^s$, and $R^v$ may represent; the $C_{1-3}$ alkyl part of alkylphenyl groups which $R^b$, $R^d$, $R^h$, $R^k$, $R^p$, $R^s$ and $R^v$ may represent; alkoxy groups which $R^b$, $R^h$, $R^k$, $R^p$, $R^s$ and $R^v$ may represent; and alkoxy and acyloxy groups with which $R^b$, $R^d$, $R^h$, $R^k$, $R^p$, $R^s$ and $R^v$ may be substituted, may, when there is a sufficient number of carbon atoms, be linear or branched, and may be saturated o r unsaturated.

Halo groups with which $R^a$, $R^b$, $R^c$, $R^d$, $R^h$, $R^k$, $R^p$, $R^s$ and $R^v$ may be substituted include fluoro, chloro, bromo and iodo.

The wavy lines on the bond in the fragments of formulae IIId, IIIe or IIIf signify the bond position of the fragment.

Preferred compounds of formula Ia include those wherein $D^1$ represents H and $D^2$ represents OH, $OCH_3$, $OC(O)R^b$ or $C(O)OR^d$, wherein $R^b$ and $R^d$ are as hereinbefore defined.

Compounds of formula Ia may also be prepared directly from compounds of formula I in accordance with techniques well known to those skilled in the art.

For example, compounds of formula Ia in which $D^1$ or $D^2$ represents $C(O)OR^d$ may be prepared by reaction of a corresponding compound of formula I with a compound of formula XXXVa, $L^3$—$C(O)OR^d$            XXXVa wherein $L^3$ represents a leaving group such as Hal or p-nitrophenoxy, and Hal and $R^d$ are as hereinbefore defined for example at 0° C. in the presence of a suitable base (e.g. NaOH) and an appropriate organic solvent (e.g. THF).

Compounds of formula Ia may also be prepared directly from other compounds of formula Ia in accordance with techniques well known to those skilled in the art.

Compounds of formula Ia in which $D^1$ or $D^2$ represents OH may be prepared by reaction of a corresponding compound of formula Ia in which $D^1$ or $D^2$ (as appropriate) represents $COOR^d$ and $R^d$ is as hereinbefore defined with hydroxylamine (or a hydrohalide salt thereof), for example at 40° C. in the presence of a suitable base (e.g. TEA) and an appropriate organic solvent (e.g. THF).

Compounds of formula Ia in which $D^1$ or $D^2$ represents $OC(O)OR^c$, and $R^c$ is as hereinbefore defined, may be prepared by reaction of a corresponding compound of formula Ia in which $D^1$ or $D^2$ (as appropriate) represents OH with a compound of formula XXXVI, $$L^3C(O)OR^c \qquad \text{XXXVI}$$

wherein $L^3$ and $R^c$ are as hereinbefore defined, for example at room temperature in the presence of a suitable base (e.g. TEA, pyridine or DMAP) and an appropriate organic solvent.

Compounds of formula Ia in which $D^1$ or $D^2$ represents $OC(O)R^b$, and $R^b$ is as hereinbefore defined, may be prepared by reaction of a corresponding compound of formula Ia in which $D^1$ or $D^2$ (as appropriate) represents OH with a compound of formula XXXVIa, $$R^bC(O)L^4 \qquad \text{XXXVIa}$$

wherein $L^4$ represents a suitable leaving group such as OH, Hal or $R^bC(O)O$, and Hal and $R^b$ are as hereinbefore defined, for example at or below room temperature in the presence of a suitable base (e.g. TEA, pyridine or DMAP) and an appropriate organic solvent (e.g. $Ch_2Cl_2$).

Compounds of formula Ia in which $B^1$ represents a structural fragment of formula IIId (in which $X^5$, $X^6$, $X^7$ and $X^8$ all represent CH) or IIIf, in which, in both cases, $D^1$ represents H and $D^2$ represents OH or $OR^a$ wherein $R^a$ is as hereinbefore defined may alternatively be prepared by reaction of a compound of formula XXXVII,

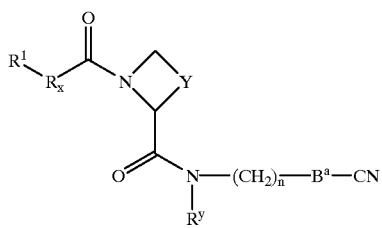

XXXVII wherein $B^a$ represents phenyl-1,4-ene or cyclohexyl-1,4-ene and $R^1$, $R_x$, Y, $R^y$ and n are as hereinbefore defined with a compound of formula XXXVIII, $$H_2NOR^{a1} \qquad \text{XXXVIII}$$

wherein $R^{a1}$ represents H or $R^a$ and $R^a$ is as hereinbefore defined, for example at between 40 and 60° C., in the presence of a suitable base (e.g. TEA) and an appropriate organic solvent (e.g. THF, $CH_3CN$, DMF or DMSO). Compounds of formula Ia in which $D^1$ or $D^2$ represents OH or $OR^a$ may alternatively be prepared in an analogous fashion by reaction of a corresponding compound of formula Ia, wherein $D^1$ or $D^2$ (as appropriate) represent $OC(O)R^b$, and $R^b$ is as hereinbefore defined, with a compound of formula XXXVIII, as defined above.

Compounds of formula XXXVII may be prepared in accordance with peptide coupling techniques, for example in analogous fashion to the methods described hereinbefore for compounds of formula I. Compounds of formulae XXXVa, XXXVI, XXXVIa and XXXVIII are commercially available, are well known in the literature, or are available using known techniques.

According to a further aspect of the invention there is provided a compound of formula Ia as defined above except that:

$R^b$ and $R^c$ independently represent $C_{1-17}$ alkyl, phenyl or 2-naphthyl (all of which are optionally substituted by $C_{1-6}$ alkyl or halo);

$R^d$ represents 2-naphthyl, phenyl, $C_{1-3}$ alkylphenyl (which latter three groups are optionally substituted by $C_{1-6}$ alkyl, $C_{1-6}$ alkoxy, nitro or halogen), $CH(R^f)(CH(R^g)_pOC(O)R^h$ (in which $R^f$ and $R^1$ independently represent H or $C_{1-6}$ alkyl, $R^h$ represents 2-naphthyl, phenyl, $C_{1-6}$ alkoxy or $C_{1-8}$ alkyl (which latter group is optionally substituted by halo, $C_{1-6}$ alkoxy or $C_{1-6}$ acyloxy), and p represents 0 or 1) or $C_{1-12}$ alkyl (which latter group is optionally substituted by $C_{1-6}$ alkoxy, $C_{1-6}$ acyloxy or halogen);

$R^a$ and $R^e$ independently represent phenyl, benzyl, $(CH_2)_2OC(O)CH_3$ or $C_{1-6}$ alkyl which latter group is optionally interrupted by oxygen;

or a pharmaceutically acceptable salt thereof.

Persons skilled in the art will appreciate that, in order to obtain compounds of formula I, or formula Ia, in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups. Accordingly, the order and type of chemistry involved will dictate the need, and type, of protecting groups as well as the sequence for accomplishing the synthesis.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

The protected derivatives of compounds of formula I (e.g. compounds of formula Ia) may be converted chemically to compounds of formula I using standard deprotection techniques (e.g. hydrogenation), for example as described hereinafter.

It will also be appreciated by those skilled in the art that, although such protected derivatives of compounds of formula I (e.g. compounds of formula Ia) may not possess pharmacological activity as such, they may be administered parenterally or orally and thereafter metabolised in the body to form compounds of formula I which are pharmacologically active. Such derivatives may therefore be described as "prodrugs". All prodrugs of compounds of formula I are included within the scope of the invention.

Protected derivatives of compounds of formula I which are particularly useful as prodrugs include compounds of formula Ia.

Compounds of formula I, pharmaceutically-acceptable salts, tautomers and stereoisomers thereof, as well as prodrugs thereof (including compounds of formula Ia which are prodrugs of compounds of formula I), are hereinafter referred to together as "the compounds of the invention".

MEDICAL AND PHARMACEUTICAL USE

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent inhibitors of thrombin either as such or, in the case of prodrugs, after administration, for example as demonstrated in the tests described below.

The compounds of the invention are thus expected to be useful in those conditions where inhibition of thrombin is required.

The compounds of the invention are thus indicated in the treatment and/or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (eg in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

BIOLOGICAL TESTS

Test A
Determination of Thrombin Clotting Time (TT)

The inhibitor solution (25 μL) was incubated with plasma (25 μL) for three minutes. Human thrombin (T 6769; Sigma Chem Co) in buffer solution, pH 7.4 (25 μL) was then added and the clotting time measured in an automatic device (KC 10; Amelung).

The clotting time in seconds was plotted against the inhibitor concentration, and the $IC_{50}TT$ was determined by interpolation. $IC_{50}TT$ is the concentration of inhibitor in the test that doubles the thrombin clotting time for human plasma.

Test B
Determinaton of Thrombin Inhibition with a Chromogenic, Robotic Assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 $\mu$L), 1 mmol/L, were diluted serially 1:3 (24+48 $\mu$L) with DMSO to obtain ten different concentrations, which were analysed as samples in the assay. 2 $\mu$L of test sample was diluted with 124 $\mu$L assay buffer, 12 $\mu$L of chromogenic substrate solution (S-2366, Chromogenix, Mölndal, Sweden) in assay buffer and finally 12 $\mu$L of $\alpha$-thrombin solution, (Human $\alpha$-thrombin, Sigma Chemical Co.) both in assay buffer, were added, and the samples mixed. The final assay concentrations were: test substance 0.00068–13.3 $\mu$mol/L, S-2366 0.30 mmol/L, $\alpha$-thrombin 0.020 NIHU/mL. The linear absorbance increment during 40 minutes incubation at 37° C. was used for calculation of percentage inhibition for the test samples, as compared to blanks without inhibitor. The $IC_{50}$-robotic value, corresponding to the inhibitor concentration which caused 50% inhibition of the thrombin activity, was calculated from a log dose vs. % inhibition curve.

Test C
Determinaton of the Inhibition Constant $K_i$ for Human Thrombin $K_i$-determinations were made using a chromogenic substrate method, performed at 37° C. on a Cobas Bio centrifugal analyser (Roche, Basel, Switzerland). Residual enzyme activity after incubation of human $\alpha$-thrombin with various concentrations of test compound was determined at three different substrate concentrations, and was measured as the change in optical absorbance at 405 nm.

Test compound solutions (100 $\mu$L; normally in buffer or saline containing BSA 10 g/L) were mixed with 200 $\mu$L of human $\alpha$-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 $\mu$L sample, together with 20 $\mu$L of water, was added to 320 $\mu$L of the substrate S-2238 (Chromogenix AB, Mölndal, Sweden) in assay buffer, and the absorbance change ($\Delta$A/min) was monitored. The final concentrations of S-2238 were 16, 24 and 50 $\mu$mol/L and of thrombin 0.125 NIH U/ml.

The steady state reaction rate was used to construct Dixon plots, i.e. diagrams of inhibitor concentration vs. 1/($\Delta$A/min). For reversible, competitive inhibitors, the data points for the different substrate concentrations typically form straight lines which intercept at $x=-K_i$.

Test D
Determination of Activated Partial Thromboplastin Time (APTT)

APTT was determined in pooled normal human citrated plasma with the reagent PTT Automated 5 manufactured by Stago. The inhibitors were added to the plasma (10 $\mu$L inhibitor solution to 90 $\mu$l plasma) and incubated with the APTT reagent for 3 minutes followed by the addition of 100 $\mu$L of calcium chloride solution (0.025M) and APTT was determined in the mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in human plasma that doubled the Activated Partial Thromboplastin Time.

Test E
Determination of Thrombin Time ex Vivo

The inhibition of thrombin after oral or parenteral administration of the compounds of formula I and Ia, dissolved in ethanol:Solutol™:water (5:5:90), were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L.) and 9 parts of blood. The tubes were centrifuged to obtain platelet poor plasma. The plasma was used for determination of thrombin time as described below.

The citrated rat plasma, 100 $\mu$l, was diluted with a saline solution, 0.9%, 100 $\mu$l, and plasma coagulation was started by the addition of human thrombin (T 6769, Sigma Chem Co, USA) in a buffer solution, pH 7.4, 100 $\mu$l. The clotting time was measured in an automatic device (KC 10, Amelumg, Germany).

Where a compound of formula Ia was administered, concentrations of the appropriate active thrombin inhibitor of formula I in the rat plasma were estimated by the use of standard curves relating the thrombin time in the pooled citrated rat plasma to known concentrations of the corresponding "active" thrombin inhibitor dissolved in saline.

Based on the estimated plasma concentrations of the active thrombin inhibitor of formula I (which assumes that thrombin time prolongation is caused by the aforementioned compound) in the rat, the area under the curve after oral and/or parenteral administration of the corresponding prodrug of formula Ia was calculated (AUCpd) using the trapezoidal rule and extrapolation of data to infinity.

The bioavailability of the active thrombin inhibitor of formula I after oral or parenteral administration of the prodrug of formula Ia was calculated as below:

[(AUCpd/dose)/(AUCactive,parenteral/dose)×100 where AUCactive,parenteral represents the AUC obtained after parenteral administration of the corresponding active thrombin inhibitor of formula I to conscious rats as described above.

Test F
Determination of Thrombin Time in Urine ex Vivo

The amount of the active thrombin inhibitor of formula I that was excreted in urine after oral or parenteral administration of the compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 $\mu$L) was incubated with the concentrated rat urine, or saline dilutions thereof, for one minute. Plasma coagulation was then initiated by the administration of human thrombin (T 6769, Sigma Chem Company) in buffer solution (pH 7.4; 100 $\mu$L). The clotting time was measured in an automatic device (KC 10; Amelung).

The concentrations of the active thrombin inhibitor of formula I in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor of formula I after oral or parenteral administration of the prodrug was calculated as below:

[(AMOUNTpd/dose)/(AMOUNTactive,parenteral/dose]×100 where AMOUNTactive,parenteral represents the amount excreted in the urine after parenteral administration of the corresponding active thrombin inhibitor of formula I to conscious rats as described above.

The invention is illustrated by way of the following examples. The amino acids Pro and Aze are defined as the S-isomers if not otherwise specified. The examples were obtained as diastereoisomers if not otherwise specified.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS). $^1$H NMR and $^{13}$C NMR measurements were performed on BRUKER ACP 300 and Varian UNITY plus 400, 500 and 600 spectrometers, operating at $^1$H frequencies of 300.13, 399.96, 499.82 and 599.94 MHz respectively, and at $^{13}$C frequencies of 75.46, 100.58, 125.69 and 150.88 MHz respectively. Flash chromatography was carried out on silica gel (230–400 mesh). Preparative RPLC was performed on reverse phase columns (250 mm, 20 or 50 mm; 5 to 7 μM phase Chromasil C8) with flow rates of 10 to 50 mL/min using a UV detector (270 to 280 nm).

Example 1

(S)- or (R)-1-Hydroxy-7-methoxytetralin-1-yl-C(O)-Pro-Pab i) 1-Hydroxy-7-methoxytetralin-1-yl-carboxylic acid, methyl ester The sub-title compound was prepared according to the method described by is C. F. Bigge et al (J. Med. Chem (1993) 36, 1977) using 7-methoxytetralone (1.0 g; 5.67 mmol) and methanol instead of ethanol. Yield: 1.22 g (90%).

$^1$H-NMR (300 MHz; CDCl$_3$): δ7.05 (d, 1H), 6.80 (d, 1H), 6.65 (s, 1H), 3.80 (s, 3H), 3.75 (s, 3H), 2.85–2.65 (m, 2H), 2.25–1.90 (m, 4H)

(ii) 1-Hydroxy-7-methoxytetralin-1-yl-carboxylic acid

1-Hydroxy-7-methoxytetralin-1-yl-carboxylic acid, methyl ester (1.16 g; 4.9 mmol; from step (i) above) was dissolved in THF (10 mL) and lithium hydroxide (0.41 g; 9.8 mmol) was added to the resultant solution, followed by water (4 mL). The reaction mixture was stirred at room temperature for 3 h, the THF was evaporated, and the aqueous phase was washed with methylene chloride. The reaction mixture was acidified with HCl (2M) and then saturated with NaCl(s). After extraction with CH$_2$Cl$_2$, the organic phase was dried and concentrate d. Yield: 765 mg (70%).

LC-MS (m/z) 221 (M−1)$^-$ $^1$H-NMR (400 MHz; CDCl$_3$): δ7.07 (d, 1H), 6.82 (dd, 1H), 6.77 (d, 1H), 3.76 (s, 3H), 2.83–2.71 (m, 2H), 2.32–2.21 (m, 1H), 2.12–1.88 (m, 3H)

(iii) (R)- and (S)-1-Hydroxy-7-methoxytetralin-1-yl-C(O)-Pro-Pab(Z)

A solution of 1-hydroxy-7-methoxytetralin-1-yl-carboxylic acid (222 mg; 1.0 mmol; from step (ii) above), H-Pro-Pab(Z) (499 mg; 1.1 mmol; prepared according to the method described in International Patent Application WO 97/02284) and TBTU (353 mg; 1.1 mmol) in DMF (10 ml) was cooled to 0° C., and DIPEA (517 mg, 4.0 mmol) was added. The reaction mixture was stirred at room temperature for 4 days and then the same amounts of H-Pro-Pab(Z), TBTU and DIPEA were added at 0° C. After 3 days the reaction mixture was concentrated and dissolved in water: EtOAc (1:1). The aqueous phase was extracted with EtOAc and the combined organic phase was dried (Na$_2$SO$_4$) and concentrated. The product was purified using flash chromatography (EtOAc:EtOH; 100:0 to 95:5). Further purification using preparative RPLC (CH$_3$CN:0.1M ammonium acetate; 40:60) separated the diastereomers: Compound 1A (faster moving diastereomer; 10 mg; 1.7%) and Compound 1B (slower moving diastereomer; 10 mg; 1.7%). Yield: 20 mg (3.4%).

Compound 1A $^1$H-NMR (400 MHz; CDCl$_3$): δ7.82 (d, 2H), 7.44 (d, 2H), 7.38–7.29 (m, 4H), 7.05 (d, 2H), 6.80 (dd, 1H), 6.54 (d, 1H), 5.21 (s, 2H) 4.68–4.63 (dd, 1H), 4.45 (m, 2H), 3.71 (s, 3H), 3.12 (m, 1H), 2.83 (m, 1H), 2.68–2.53 (m, 2H), 2.22–2.13 (m, 2H), 2.05–1.84 (m, 7H), 1.59–1.50 (m, 1H)

Compound 1B $^1$H-NMR (400 MHz; CDCl$_3$): δ7.82 (d, 2H), 7.43 (d, 2H), 7.37–7.28 (m, 4H), 7.02 (d, 2H), 6.77 (dd, 1H), 6.57 (d, 1H), 5.20 (s, 2H) 4.58–4.51 (m, 2H), 4.42 (m, 1H), 3.62 (s, 3H), 3.12–3.04 (m, 1H), 2,83 (bd, 1H), 2.68–2.58 (m, 1H), 2.55–2.47 (m, 1H), 2.13–1.79 (m, 7H), 1.76–1.65 (m, 1H)

(iv) (S)- or (R)-1-Hydroxy-7-methoxytetralin-1-yl-C(O)-Pro-Pab

Pd/C (5%; 10 mg) was added to a solution of (R)- or (S)-1-hydroxy-7-methoxytetralin-1-yl-C(O)-Pro-Pab(Z) (10 mg; 0.017 mmol; Compound 1A from step (iii) above) in EtOH (5 mL) and HOAc (1 μL, 0.017 mmol), and the mixture was hydrogenated for 3 hours at room temperature and atmospheric pressure. The resultant mixture was filtered through Celite, the solution was concentrated, water was added and the solution was freeze dried, yielding 10 mg (98%; purity 92.2%) of the title compound as a white powder.

LC-MS (m/z) 451 (M+1)$^+$ $^1$H-NMR (400 MHz; CD$_3$OD): δ7.75 (d, 2H), 7.57 (d, 2H), 7.08 (d, 1H), 6.83 (dd, 1H), 6.60 (d, 1H), 4.63–4.40 (m, 3H), 3.69 (s, 3H), 3.43–3.35 (m, 1H), 2.88–2,67 (m, 3H), 2.23–2.11 (m, 2H), 2.20–1.77 (m, 8H), 1.63–1.51 (m, 1H)

Example 2

(R)- or (S)-1-Hydroxy-7-methoxytetralin-1-yl-C(O)-Pro-Pab

The title compound was prepared according to the method described in Example 1(iv) above from (R)- or (S)-1-hydroxy-7-methoxytetralin-1-yl-C(O)-Pro-Pab(Z) (10 mg; 0.017 mmol; Compound 1B from Example 1(iii) above). Yield: 10 mg (98%; purity 80.4%).

LC-MS (m/z) 451 (M+1)$^+$ $^1$H-NMR (400 MHz; CD$_3$OD) δ7.78 (d, 2H), 7.63 (d, 2H), 7.04 (d, 1H), 6.78 (dd, 1H), 6.75 (d, 1H), 4.67–4.48 (m, 3H), 3.68 (s, 3H), 3.30–3.23 (m, 1H), 2.86–2.61 (m, 3H), 2.23–1.71 (m, 11H)

Example 3

(S)- or (R)-1-Hydroxy-7-methoxytetralin-1-yl-C(O)-Aze-Pab×HOAc (i) (S)- and (R)-1-Hydroxy-7-methoxytetralin-1-yl-C(O)-Aze-Pab(Z)

TBTU (0.584 g; 1.7 mmol), followed by DIPEA (0.200 g; 1.55 mmol) were added to an ice-cold solution of 1-hydroxy-7-methoxytetralin-1-yl-carboxylic acid (0.345 g; 1.55 mmol; see Example 1(ii) above) in DMF (10 mL). After stirring at 0° C. for 15 minutes, H-Aze-Pab(Z)×2HCl (0.750 g; 1.7 mmol; prepared according to the method described in International Patent Application WO 97/02284) and DIPEA (0.603 g; 4.65 mmol) were added and the mixture was stirred at RT for 4 days. The DMF was evaporated, and the resultant material was partitioned between water and EtOAc. The organic layer was separated, the water phase was extracted 3 times with EtOAc, and the combined organic layer was dried ($Na_2SO_4$) and concentrated. The product, a white powder, was further purified using preparative RPLC ($CH_3CN$:0.1M ammonium acetate; 46:54) yielding 122 mg (28%) of a faster moving fraction (Compound 3A) and 63 mg (14%) of a slower moving fraction (Compound 3B).

Compound 3A:
LC-MS (m/z) 571 (M+1)$^+$
$^1$H-NMR (400 MHz; $CDCl_3$): (complex due to rotamers) δ8.22 (t, 0.5H, rotamer); 7.94 (t, 0.5H, rotamer); 7.83 (t, 1H); 7.45–7.3 (m, 9H); 7.4 (t, 1H); 6.80 (m, 1H); 4.93 (m, 1H); 4.55 (m, 5H); 3.76 (s, 3H); 3.0 (m, 2H); 2.8 (m, 2H); 2.6 (m, 2H); 2.5 (m, 1H); 2.38 (m, 1H); 2.25 (m, 1H); 2.0–1.8 (m, 9H)

(ii) (S)- or (R)-1-Hydroxy-7-methoxytetralin-1-yl-C(O)-Aze-Pab×HOAc

Prepared according to the method described in Example 1(iv) from (S)- or (R)-1-hydroxy-7-methoxytetralin-1-yl-C(O)-Aze-Pab(Z) (0.058 g;0.1 mmol; Compound 3A from step (i) above), HOAc (5.8 μL; 0.1 mmol), and Pd/C (5%; 50 mg) in EtOH (5 ml). Yield 15 mg (59%).

LC-MS (m/z) 437 (M+1)$^+$
$^1$H-NMR (400 MHz; $D_2O$): δ7.65 (d, 2H); 7.47 (d, 2H); 7.16 (d, 1H); 6.90 (d, 1H); 6.71 (d, 1H); 4.91 (dd, 1H); 4.40 (m, 1H); 4.15 (m, 1H); 3.94 (m, 1H); 3.60 (s, 3H); 2.75 (m, 3H); 2.53 (m, 1H); 2.1 (m, 2H); 2.0–1.75 (m, 7H)
$^{13}$C-NMR (100 MHz; $CDCl_3$) δ182.5; 178.3; 174.0

Example 4

(R)- or (S)-1-Hydroxy-7-methoxytetralin-1-yl-C(O)-Aze-Pab (i) 4-(Amino, methoxyiminomethyl)benzyl amine (H-Pab(OMe))

Platinum oxide (200 mg) was added to a solution of 4-(amino, methoxyiminomethyl)benzyl azide (10 g; 0.049 mol; prepared according to the method described in WO 94/29336) in 200 mL of ethanol. The mixture was hydrogenated at atmospheric pressure for 8 h, filtered through Hyflo and concentrated. The crude product was used directly in the following step.

$^1$H-NMR (400 MHz; $CD_3OD$): δ7.60 (d, 2H); 7.37 (d, 2H); 3.81 (s, 3H); 3.80 (s, 2H).

(ii) Boc-Aze-Pab(OMe)

DIPEA (17.5 mL; 105 mmol) was added to an ice-cold solution of Boc-Aze-OH (9.7 g; 48 mmol) and H-Pab(OMe) (9.4 g; 52 mmol; from step (i) above) and TBTU (18.5 g; 58 mmol) in DMF (100 mL), and the mixture was stirred overnight at RT. The resultant mixture was poured onto water (50 mL), the pH was adjusted to ca 9, and the mixture was extracted three times with EtOAc. The combined organic layer was washed with $NaHCO_3$/aq, water and brine, dried ($Na_2SO_4$), and concentrated. The crude product was purified using flash chromatography (Si-gel, EtOAc). Yield: 11.9 g (69%).

$^1$H-NMR (400 MHz; $CDCl_3$): δ7.60 (d, 2H); 7.31 (d, 2H); 4.78 (b, 2H); 4.69 (m, 1H); 4.50 (b, 2H); 3.92 (s+m, 4H); 3.79 (m, 1H); 2.46 (b, 2H); 1.42 (s, 9H)

iii) H-Aze-Pab(OMe)×2HCl

A solution of Boc-Aze-Pab(OMe) (9.4 g; 26 mmol; from step (ii) above) in EtOAc (250 mL) was saturated with HCl(g). EtOH (abs; 125 mL) was added to the resultant emulsion and the mixture was sonicated for 10 min. EtOAc was added until the solution became turbid, whereafter the sub-title product soon crystallized. Yield: 6.7 g (77%).

LC-MS (m/z) 263 (M+1)$^+$
$^1$H-NMR (400 MHz; $CD_3OD$): δ7.74 (d, 2H); 7.58 (d, 2H); 5.13 (t, 1H); 4.57 (m, 2H); 4.15 (m, 2H); 3.97 (s+m, 4H); 2.87 (m, 1H); 2.57 (m, 1H)
$^{13}$C-NMR (75 MHz; $CDCl_3$): (carbonyl and/or amidine carbons) δ168.9; 168.8; 161.9

(iv) 1-Hydroxy-7-methoxytetralin-1-yl-C(O)-Aze-Pab (OMe)

H-Aze-Pab(OMe) (0.587 g; 1.85 mmol; from step (iii) above), TBTU (0.594 g; 1.85 mmol) and DIPEA (0.87 g; 6.73 mmol) were added, in that order, to an ice-cold solution of 1-hydroxy-7-methoxytetralin-1-yl-carboxylic acid (0.374 g; 1.68 mmol; see Example 1(ii) above) in $CH_3CN$. The resultant mixture was stirred at RT for 6 days. The solution was concentrated and the crude material was purified using preparative HPLC ($CH_3CN$:0.1M ammonium acetate; 25:75), which procedure separated diastereomers, yielding 122 mg (31.2%) of a faster moving diastereomer (Compound 4A) and 120 mg (30.7%) of a slower moving diastereomer (Compound 4B).

Compound 4B
LC-MS (m/z) 466 (M+1)$^+$
$^1$H-NMR (500 MHz; $CDCl_3$): δ8.08 (t, 1H); 7.63 (d, 2H); 7.35 (d, 2H); 7.02 (d, 1H); 6.80 (dd, 1H); 6.57 (d, 1H); 4.90 (dd, 1H); 4.79 (b, 2H); 4.53 (m, 2H); 3.91 (s, 3H); 3.65 (s+m, 4H); 2.97 (q, 1H); 2.81 (bd, 1H); 2.59 (m, 1H); 2.49 (m, 1H); 2.38 (m, 1H); 2.03–1.85 (m, 4H)

(v) (R)- or (S)-1-Hydroxy-7-methoxytetralin-1-yl-C(O)-Aze-Pab

The title compound was prepared according to the method described in Example 1(iv) above from 1-hydroxy-7-methoxytetralin-1-yl-C(O)-Aze-Pab(OMe) (20 mg; 0.043 mmol; Compound 4B from step (iv) above), AcOH (3 mg; 0.05 mmol) and Pd/C (10%; 20 mg) in EtOH (5 mL). Yield 19 mg (89%).

LC-MS (m/z) 436 (M+1)$^+$
$^1$H-NMR (400 MHz; $D_2O$): δ7.79 (d, 2H); 7.55 (m, 2H); 7.20 (d, 1H); 6.95 (m, 1H); 6.79 (d, 1H); 4.92 (dd, 1H); 4.58 (m, 2H); 4.18 (m, 2H); 3.77 (s, 3H); 3.63 (m, 2H); 2.8 (m, 3H); 2.6 (m, 2H); 2.1 (m, 4H); 1.9 (m, 2H) $^{13}$C-NMR (75 MHz; $CDCl_3$): (carbonyl and/or amidine carbons) δ177.9; 173.8; 167.6

Example 5

1-Hydroxy-5-methoxytetralin-1-yl-C(O)-Aze-Pab×HOAc (i) 1-Hydroxy-5-methoxytetralin-1-yl-carboxylic acid methyl ester The sub-title compound was prepared according to a method described by Bigge et al (J. Med. Chem. (1993) 36, 1977) from 5-methoxytetralone (1.0 g; 5.67 mmol), $Me_3SiCN$ (0.619 g; 6.24 mmol), and $ZnI_2$ (8 mg; cat.). Yield 1.11 g (83%).

¹H-NMR (500 MHz; CDCl₃): δ7.16 (m, 1H); 6.91 (d, 1H); 6.76 (t, 1H); 6.45 (br, 1H); 5.97 (br, 1H); 3.815 (s, 2H); 3.81 (s, 3H); 2.88 (m, 1H); 2.56 (m, 2H); 2.14 (m, 2H); 1.95 (m, 2H)

(ii) 1-Hydroxy-5-methoxytetralin-1-yl-carboxylic acid

Prepared according to the method described in Example 1(ii) above from 1-hydroxy-5-methoxytetralin-1-yl-carboxylic acid, methyl ester (1.11 g; 4.7 mmol; from step (i) above) and LiOH.H₂O (0.395 g; 9.4 mmol). Yield 460 mg (36%).

¹H-NMR (400 MHz; CDCl₃): δ7.18 (m, 1H); 6.86 (d, 1H); 6.79 (d, 1H); 3.82 (s, 3H); 2.86 (dt, 1H); 2.58 (m, 1H); 2.20 (m, 1H); 2.10–1.85 (m, 4H)

(iii) 1-Hydroxy-5-methoxytetralin-1-yl-C(O)-Aze-Pab(Z)

TBTU (0.528 g; 1.64 mmol) was added to an ice-cold solution of 1-hydroxy-5-methoxytetralin-1-yl-carboxylic acid (0.332 g; 1.49 mmol; from step (ii) above) in CH₃CN (15 mL). The mixture was stirred at 0° C. for 2 h, and H-Aze-Pab(Z)×2HCl (0.656 g; 1.49 mmol) and DIPEA (0.599 g; 3.1 mmol) were added. The resultant mixture was stirred at RT overnight, and the solution was concentrated. The crude product was purified using preparative RPLC (CH₃CN:0.1M ammonium acetate; 40:60). Yield 140 mg (16%).

LC-MS (m/z) 571 (M+1)⁺

¹H-NMR (400 MHz; CDCl₃): δ7.82 (dd, 2H); 7.43 (d, 2H); 7.33 (t, 2H); 7.27 (m, 3H); 6.73 (m, 2H); 5.20 (s, 2H); 4.89 (m, 1H); 4.60–4.40 (m, 2H); 3.80 (s, 3H); 3.62 (m, 1H); 2.94 (m, 2H); 2.34 (m, 2H); 1.95–1.8 (m, 4H)

¹³C-NMR (100 MHz; CDCl₃): (carbonyl and/or amidine carbons) δ184.2; 179.0; 178.6; 172.3; 171.6; 168.9

(iv) 1-Hydroxy-5-methoxytetralin-1-yl-C(O)-Aze-Pab× HOAc

Prepared according to the method described in Example 1(iv) from 1-hydroxy-5-methoxytetralin-1-yl-C(O)-Aze-Pab(Z) (47 mg; 0.082 mmol; from step (iii) above), AcOH (5 mg; 0.082 mmol) and Pd/C (5%; 20 mg) in EtOH (5 mL). Yield 37 mg (100%).

LC-MS (m/z) 437 (M+1)⁺

¹H-NMR (400 MHz; D₂O): δ7.76 (dd, 2H); 7.54 (dd, 2H); 7.27 (m, 1H); 7.01 (t, 1H); 6.90 (dd, 1H); 4.91 (dd, 1H); 4.5 (m, 1H); 4.20 (m, 1H); 3.87 (s, 3H); 3.63 (m, 1H); 2.90 (m, 1H); 2.7–2.4 (m, 2H); 2.24 (m, 1H)

¹³C-NMR (100 MHz; CDCl₃): (carbonyl and/or amidine carbons) δ181.5; 177.5; 177.2; 173.1; 173.0; 166.7

Example 6

1-Hydroxy-5,7-dimethyltetralin-1-yl-C(O)-Aze-Pab×HOAc (i) 1-Hydroxy-5,7-dimethyltetralin-1-yl-carboxylic acid, methyl ester The sub-title compound was prepared according to a method described by Bigge et al (J. Med. Chem. (1993) 36, 1977) from 5,7-dimethyltetralone (1.0 g; 5.74 mmol), Me₃SiCN (0.626 g; 6.31 mg), and ZnI₂ (8 mg; cat.). Yield 1.24 g (92%).

¹H-NMR (400 MHz; CDCl₃): δ6.94 (s, 1H); 6.81 (s, 1H); 3.77 (s, 3H); 2.82 (t, 1H); 2.73 (m, 1H); 2.60 (m, 3H); 2.25 (s, 3H); 2.21 (s, 3H); 2.00 (m, 3H)

(ii) 1-Hydroxy-5,7-dimethyltetralin-1-yl-carboxylic acid

Prepared according to the method described in Example 1(ii) from 1-hydroxy-5,7-dimethyltetralin-1-yl-carboxylic acid, methyl ester (1.24 g; 5.27 mmol; from step (i) above) and LiOH.H₂O (0.443 mg; 10.6 mmol). Yield 0.629 g (50%).

LC-MS (m/z) 437 (M−1)⁻

¹H-NMR (400 MHz; CDCl₃): δ6.97 (s, 1H); 6.92 (s, 1H); 2.72 (m, 1H); 2.60 (m, 1H); 2.27 (s, 3H); 2.22 (s, 3H); 2.06 (m, 2H); 1.95 (m, 2H)

(iii) 1-Hydroxy-5,7-dimethyltetralin-1-yl-C(O)-Aze-Pab (OMea)

Prepared according to the method described in Example 4(iv) above from 1-hydroxy-5,7-dimethyltetralin-1-yl-carboxylic acid (0.20 g; 0.91 mmol; from step (ii) above), H-Aze-Pab(OMe)×1.5HCl (0.317 g; 1.0 mmol; see Example 4(iii) above), TBTU (0.321 g; 1.0 mmol) and DIPEA (0.469 g; 3.63 mmol). The solution was concentrated and the remainder was purified using preparative RPLC (CH₃CN:0.1M ammonium acetate; 30:70). The fractions of interest were concentrated and were then extracted (×3) with EtOAc. The combined organic layer was dried (Na₂SO₄) and concentrated. The dry product was dissolved in a small amount of water/CH₃CN and freeze dried. Yield 40 mg (9.5%).

LC-MS (m/z) 463 (M+1)⁺

¹H-NMR (400 MHz; CDCl₃): (complex due to diastereomers/rotamers) δ8.19 (bt, 0.5H, rotamer); 7.91 (bt, 0.5H, rotamer); 7.61 (dd, 2H); 7.35 (d, 1H); 7.28 (d, 1H); 6.93 (s, 0.5H, rotamer); 6.91 (s, 0.5H, rotamer); 6.80 (s, 0.5H, rotamer); 6.70 (s, 0.5H, rotamer); 4.91 (m, 2H); 4.79 (b, 2H); 4.50 (m, 3H); 3.91 (d, 3H); 3.74 (m, 0.5H, rotamer); 3.61 (m, 0.5H, rotamer); 2.78 (bd, 1H); 2.57 (m, 1H); 2.38 (m, 2H); 2.26 (m, 2H); 2.19 (d, 6H); 1.95 (m, 3H)

¹³C-NMR (100 MHz; CDCl₃): (carbonyl and/or amidine carbons) δ179.2; 178.9; 171.6; 171.4

(iv) 1-Hydroxy-5,7-dimethyltetralin-1-yl-C(O)-Aze-Pab× HOAc

Prepared according to the method described in Example 1(iv) above from 1-hydroxy-5,7-dimethyltetralin-1-yl-C (O)-Aze-Pab(OMe) (20 mg; 0.043 mmol; from step (iii) above), HOAc (2.6 mg; 0.043 mmol) and Pd/C (10%; 10 mg). Yield 20 mg (94%).

LC-MS (m/z) 435 (M+1)⁺

¹H-NMR (400 MHz; D₂O): δ7.79 (dd, 1H); 7.70 (d, 1H); 7.53 (m, 2H); 7.07 (d, 1H); 6.92 (s, 1H); 4.91 (m, 1H); 4.17 (m, 1H); 3.76 (m, 0.5H, rotamer); 3.60 (m, 0.5H, rotamer); 2.80 (d, 1H); 2.55 (m, 2H); 2.23 (s, 3H); 2.07 (m, 2H); 1.95 (s, 6H)

¹³C-NMR (100 MHz; D₂O): (carbonyl and/or amidine carbons) δ177.9; 173.3

Example 7

1-Hydroxy-7-aminotetralin-1-yl-C(O)-Aze-Pab× HOAc (i) 1-Hydroxy-7-nitrotetralin-1-yl-carboxylic acid, methyl ester The sub-title compound was prepared according to a method described by Bigge et al (J. Med. Chem. (1993) 36, 1977) from 7-nitrotetralone (2.0 g; 10.5 mmol), Me₃SiCN (1.14 g; 11.5 mg) and ZnI₂ (8 mg; cat.). Yield 2.87 g (100%) (over 3 steps).

¹H-NMR (400 MHz; CDCl₃): δ8.16 (dd, 1H); 8.04 (m, 1H); 7.36 (dd, 1H); 3.73 (s, 3H); 2.92 (m, 2H); 2.30 (m, 1H); 2.00 (m, 3H)

(ii) 1-Hydroxy-7-nitrotetralin-1-yl-carboxylic acid

The sub-title compound was prepared according to the method described in Example 1(ii) above from 1-hydroxy-7-nitrotetralin-1-yl-carboxylic acid, methyl ester (2.0 g; 8.3 mmol; from step (i) above) and LiOH.H₂O (0.7 g; 16.6 mmol). Yield 1.72 g (88%).

LC-MS (m/z) 236 (M+1)⁺

¹H-NMR (400 MHz; CDCl₃): δ8.10 (dd, 1H); 8.05 (m, 1H); 7.30 (d, 1H); 2.92 (m, 2H); 2.30 (m, 1H); 2.15–1.85 (m, 3H)

(iii) 1-Hydroxy-7-nitrotetralin-1-yl-C(O)-Aze-Pab(Z)

HATU (0.352 g; 0.93 mmol) and DIPEA (0.200 g; 1.55 mmol) were added to an ice-cold solution of 1-hydroxy-7- nitrotetralin-1-yl-carboxylic acid (0.200 g; 0.84 mmol; from step (ii) above) in DMF (5 mL). After stirring is at 0° C. for 15 minutes a solution of H-Aze-Pab(Z)×2HCl (0.408 g; 0.93 mmol) and 2,4,6-trimethylpyridine (0.409 g; 3.37 mmol) in 5 mL of DMF was added at 0° C., and the mixture was stirred at RT overnight. The DMF was evaporated, and the crude product was purified using preparative RPLC ($CH_3CN$:0.1 M ammonium acetate; 40:60). The product was further purified using HPLC ($CH_3CN$:0.1M ammonium acetate; 46:54), yielding 214 mg (44%) of the sub-title compound.

LC-MS (m/z) 586 $(M+1)^+$ $^1$H-NMR (400 MHz; $CDCl_3$): δ8.1 (m, 2H); 7.77 (d, 1H); 7.71 (d, 1H); 7.40 (d, 2H); 7.32 (t, 2H); 7.27 (m, 2H); 7.18 (d, 1H); 4.88 (m, 1H); 4.54 (m, 0.5H, rotamer); 4.45 (dd, 0.5H, rotamer); 4.34 (m, 1H); 3.94 (m, 0.5H, rotamer); 3.82 (m, 0.5H, rotamer); 3.17 (m, 1H); 2.90 (t, 1H); 2.73 (m, 1H); 2.45–2.20 (m, 2H); 2.05–1.85 (m, 5H)

(iv) 1-Hydroxy-7-aminotetralin-1-yl-C(O)-Aze-Pab×HOAc

The title compound was prepared according to the method described in Example 1(iv) above from 1-hydroxy-7-nitrotetralin-1-yl-C(O)-Aze-Pab(Z) (0.064 g; 0.11 mmol; from step (iii) above), HOAc (6.3 μL; 0.11 mmol), and Pd/C (32 mg). The solid crude product was dissolved in water, and the water solution was freeze dried to yield 40 mg (76%).

LC-MS (m/z) 422 $(M+1)^+$ $^1$H-NMR (400 MHz; $D_2O$): δ7.75 (m, 2H); 7.53 (dd, 2H); 7.07 (d, 1H); 6.82 (bt, 1H); 6.67 (b, 1H); 4.93 (m, 1H); 4.6–4.4 (m, 2H); 4.29 (m, 0.5H, rotamer); 4.18 (m, 1H); 3.7 (m, 1H); 2.8–2.5 (, 3H)

$^{13}$C-NMR (100 MHz; $CDCl_3$) (carbonyl and/or amidine carbons) δ178.4; 178.1; 173.9; 173.8; 167.5

Example 8

1-Hydroxytetralin-1-yl-C(O)-Aze-Pab×HOAc (i) 1-Hydroxytetralin-1-yl-carboxylic acid, methyl ester The sub-title compound was prepared according to a method described by Bigge et al (J. Med. Chem. (1993) 36, 1977) from tetralone (2.0 g; 13.7 mmol), $Me_3SiCN$ (1.49 g; 15 mmol) and $ZnI_2$ (8 mg; cat.). Yield 2.5 g (88%).

(ii) 1-Hydroxytetralin-1-yl-carboxylic acid

The sub-title compound was prepared according to the method described in Example 1(ii) above from 1-hydroxytetralin-1-yl-carboxylic acid, methyl ester (2.5 g; 12.1 mmol; from step (i) above) and $LiOH.H_2O$ (1.02 g; 24.2 mmol). Yield 400 mg (17%).

$^1$H-NMR (400 MHz; $CDCl_3$): δ7.18 (m, 4H); 2.92 (t, 0.5H, rotamer); 2.78 (m, 2H): 2.61 (t, 0.5H, rotamer); 2.22 (m, 1H); 2.1–1.8 (m, 4H)

(iii) 1-Hydroxytetralin-1-yl-C(O)-Aze-Pab(Z)

The sub-title compound was prepared according to the method described in Example 5(iii) above from 1-hydroxytetralin-1-yl-carboxylic acid (0.284 g; 1.50 mmol; from step (ii) above), TBTU (0.531 g; 1.65 mmol), H-Aze-Pab(Z)×2HCl (0.660 g; 1.50 mmol) and DIPEA (0.602 g; 3.1 mmol). The crude product was purified using preparative RPLC ($CH_3CN$:0.1M ammonium acetate; 40:60). Yield 70 mg (8.6%).

LC-MS (m/z) 542 $(M+1)^+$ $^1$H-NMR (400 MHz; $D_2O$): (complex due to diastereomers/rotamers) δ8.15 (t, 0.5H, rotamer); 7.97 (t, 0.5H, rotamer); 7.81 (dd, 2H); 7.43 (dd, 2H); 7.30 (m, 5H); 7.19 (m, 2H); 7.12 (m, 2H); 4.88 (m, 1H); 4.47 (m, 2H); 3.79 (m, 0.5H, rotamer); 2.89 (m, 2H); 2.66 (m, 1H); 2.50 (m, 0.5H, rotamer); 2.35 (m, 1H); 2.19 (m, 0.5H, rotamer); 1.95 (m, 5H)

$^{13}$C-NMR (100 MHz; $CDCl_3$): (carbonyl and/or amidine carbons, complex due to diastereomers/rotamers) δ177.7; 177.4; 171.1; 170.5; 170.3; 167.7; 164.4

(iv) 1-Hydroxytetralin-1-yl-C(O)-Aze-Pab×HOAc

The title compound was prepared according to the method described in Example 1(iv) above from 1-hydroxytetralin-1-yl-C(O)-Aze-Pab(Z) (70 mg; 0.13 mmol; from step (iii) above), AcOH (5 mg; 0.13 mmol) and Pd/C (5%; 35 mg) in EtOH (5 mL). Yield 61 mg (100%).

LC-MS (m/z) 407 $(M+1)^+$ $^1$H-NMR (400 MHz; $CD_3OD$): δ7.74 (dd, 2H); 7.55 (dd, 2H); 7.29 (d, 1H); 7.15 m, 3H); 4.59 (m, 1H); 4.46 (m, 1H); 4.25 (m, 1H); 4.08 (m, 1H); 3.69 (m, 1H); 2.80 (m, 2H); 2.46 (m, 1H); 2.3–2.15 (m, 2H)

$^{13}$C-NMR (100 MHz; $CD_3OD$): (carbonyl and/or amidine carbons) δ180.1; 178.0; 177.8; 173.2; 168.2

Example 9

7-Methoxytetralin-1-yl-C(O)-Aze-Pab×HOAc (i) 7-Methoxy-3,4-dihydronaphthalen-1-yl-carboxylic acid, methyl ester A solution of 1-hydroxy-7-methoxytetralin-1-yl-carboxylic acid, methyl ester (0.5 g; 2.1 mmol; see Example 1(i) above) in toluene (5 mL) was added to a refluxing solution of p-TsOH (0.6 g; 3.2 mmol) in toluene (10 mL), and the resultant mixture was refluxed for 45 minutes. After cooling, the reaction mixture was diluted with ether, washed with water and $NaHCO_3$/aq, dried with $Na_2SO_4$ and concentrated. Yield 392 mg (85%).

$^1$H-NMR (500 MHz; $CDCl_3$): δ7.46 (d, 1H); 7.19 (t, 1H); 7.06 (d, 1H); 6.75 (dd, 1H); 3.84 (s, 3H); 3.83 (s, 3H); 2.69 (t, 2H); 2.38 (m, 2H)

(ii) 7-Methoxy-3,4-dihydronaphthalen-1-yl-carboxylic acid

The sub-title compound was prepared according to the method described in Example 1(ii) above from 7-methoxy-3,4-dihydronaphthalen-1-yl-carboxylic acid, methyl ester (0.39 g; 1.79 mmol; from step (i) above) and $LiOH.H_2O$ (0.15 g; 3.57 mmol). Yield 148 mg (40%).

LC-MS (m/z) 203 $(M+1)^+$ $^1$H-NMR (500 MHz; $CDCl_3$): δ7.56 (d, 1H); 7.44 (t, 1H); 7.09 (d, 1H); 6.77 (dd, 1H); 3.82 (s, 3H); 2.72 (t, 2H); 2.44 (m, 2H)

(iii) 7-Methoxy-3,4-dihydronaphthalen-1-yl-C(O)-Aze-Pab (Z)

The sub-title compound was prepared according to the method described in Example 3(i) above from 7-methoxy-3,4-dihydronaphthalen-1-yl-carboxylic acid (0.145 g; 0.71 mmol; from step (ii) above), H-Aze-Pab(Z)×2HCl (0.343 g; 0.78 mmol), TBTU (0.251 g; 0.78 mmol) and DIPEA (0.364 g, 2.84 mmol). The crude product was purified using preparative RPLC ($CH_3CN$:0.1M ammonium acetate; 54:46). The resultant solution was concentrated and the aqueous layer was extracted with EtOAc three times. The combined organic layer was dried ($Na_2SO_4$) and concentrated, yielding 121 mg (31%).

LC-MS (m/z) 553 $(M+1)^+$ $^1$H-NMR (500 MHz; $CDCl_3$): δ8.25 (t, 1H); 7.82 (d, 2H); 7.43 (d, 2H); 7.37–7.27 (m, 5H); 7.06 (d, 1H); 6.81 (d, 1H); 6.72 (dd, 1H); 6.35 (t, 1H); 5.20 (s, 2H); 5.03 (dd, 1H); 4.52 (m, 2H); 3.93 (m, 2H); 2.71 (t, 2H); 2.35 (m, 2H)

(iv) 7-Methoxytetralin-1-yl-C(O)-Aze-Pab×HOAc

The title compound was prepared according to the method described in Example 1(iv) above from 7-methoxy-3,4-dihydronaphthalen-1-yl-C(O)-Aze-Pab(Z) (88 mg; 0.16 mmol), AcOH (9 mg; 0.16 mmol) and Pd/C (10%; 44 mg). Yield 56 mg (73%), 60:40 diastereomeric mixture.

LC-MS (m/z) 421 $(M+1)^+$ $^1$H-NMR (500 MHz; $D_2O$): δ7.78 (t, 1H); 7.65 (d, 1H); 7.55 (dd, 1H); 7.49 (d, 1H); 7.42 (d, 2H); 7.36 (d, 2H); 7.16 (m, 1H); 7.05 (d, 1H); 6.84 (dd, 1H); 6.73 (dd, 1H); 6.06 (d,

1H); 5.18 (dd, 1H); 4.96 (m, 1H); 4.12 (m, 2H); 3.92 (m, 2H); 3.82 (d, 1H); 3.62 (m, 3H); 2.7 (m, 6H); 2.4 (m, 2H); 2.05 (m, 2H); 1.9 (m, 1H); 1.2 (m, 2H); 1.5 (m, 1H)

$^{13}$C-NMR (100 MHz; D$_2$O): (carbonyl and/or amidine carbons) δ182.3; 179.3; 179.1; 178.8; 173.7; 173.4; 173.0; 166.3

Example 10

(R)- and (S)-7-Methoxy-1-methyltetralin-1-yl-C(O)-Aze-Pab (i) 7-Methoxytetralin-1-yl-carboxylic acid, methyl ester The sub-title compound was prepared according to the method described in Example 1(iv) above from 7-methoxy-3,4-dihydronaphthalen-1-yl-carboxylic acid, methyl ester (3.3 g; 15 mmol; see Example 9(i) above) and Pd/C (10%; 0.5 g). The resultant mixture was filtered through Hyflo and concentrated. The crude product was purified using flash chromatography (Si-gel; heptane:EtOAc; 4:1). Yield 2.4 g (72%).

$^1$H-NMR (400 MHz; CDCl$_3$): δ7.04 (d, 1H); 6.77 (dd, 1H); 6.72 (d, 1H); 3.82 (t, 1H); 3.78 (s, 3H); 3.73 (s, 3H); 2.75 (m, 3H); 2.14 (m, 1H); 1.99 (m, 2H); 1.77 (m, 1H)

(ii) 7-Methoxy-1-methyltetralin-1-yl-carboxylic acid, methyl ester

7-Methoxytetralin-1-yl-carboxylic acid, methyl ester (0.4 g; 1.8 mmol; from step (i) above) and MeI (0.13 mL, 2.0 mmol) were added to a slurry of NaH (55% in oil; 87 mg; 2.0 mmol) in DMF (5 mL) and the mixture was stirred at RT overnight. The resultant mixture was poured onto water, and the water mixture was extracted with EtOAc:toluene 3 times. The combined organic layer was washed with water, dried (Na$_2$SO$_4$), and concentrated. Flash chromatography (Si-gel; heptane:EtOAc; 4:1) yielded 0.18 g (42%) of the sub-title compound.

$^1$H-NMR (500 MHz; CDCl$_3$): δ7.04 (d, 1H); 6.76 (m, 2H); 3.79 (s, 3H); 3.69 (s, 3H); 2.76 (m, 2H); 2.32 (m, 1H); 1.91 (m, 1H); 1.83 (m, 2H); 1.75 (m, 1H); 1.58 (s, 3H)

(iii) 7-Methoxy-1-methyltetralin-1-yl-carboxylic acid

A mixture of 7-methoxy-1-methyltetralin-1-yl-carboxylic acid, methyl ester (0.67 g; 2.9 mmol; from step (ii) above) and KOH (4 g) in EtOH:H$_2$O (1:1; 50 mL) was stirred overnight. The resultant mixture was diluted with water and extracted with ether. The aqueous layer was acidified (HCl) and extracted 3 times with ether. The combined organic layer was washed with water, dried (Na$_2$SO$_4$), and concentrated. Yield 0.58 g (81%).

$^1$H-NMR (300 MHz; CDCl$_3$): δ7.02 (d, 1H); 6.85 (d, 1H); 6.75 (dd, 1H); 3.77 (s, 3H); 2.75 (m, 2H); 2.32 (m, 1H); 1.91 (m, 1H); 1.82 (m, 1H); 1.75 (m, 2H); 1.55 (s, 3H)

(iv) 7-Methoxy-1-methyltetralin-1-yl-C(O)-Aze-Pab(Z)

The sub-title compound was prepared according to the method described in Example 3(i) above from 7-methoxy-1-methyltetralin-1-yl-carboxylic acid (0.14 g; 0.64 mmol; from step (iii) above), TBTU (0.31 g; 0.97 mmol), H-Aze-Pab(Z) (0.42 g; 0.97 mmol) and DIPEA (0.50 g; 0.67 mmol). The crude product was purified using flash chromatography (Si-gel, EtOAc). Yield 0.26 mg (72%).

$^1$H-NMR (400 MHz; CDCl$_3$): δ8.40 (b, 0.5H, rotamer); 8.27 (b, 0.5H, rotamer); 7.90 (d, 2H); 4.84 (d, 2H); 7.45 (m, 2H); 7.4–7.25 (m, 5H); 7.00 (t, 1 h); 6.75 (dd, 0.5H, rotamer); 6.71 (dd, 0.5H, rotamer); 6.62 (d, 0.5H, rotamer); 6.50 (d, 0.5H, rotamer); 5.22(s, 2H); 4.87 (dd, 1H); 4.65–4.40 (m, 2H); 3.78 (s, 3H); 3.69 (s, 3H); 3.60 (m, 1H); 2.78 (m, 2H); 2.65 (m, 1H); 2.45 (m, 1H); 2.20 (m, 1H); 1.90 (m, 3H); 1.75 (m, 3H); 1.50 (s, 3H)

(v) (R)- and (S)-7-Methoxy-1-methyltetralin-1-yl-C(O)-Aze-Pab

The title compounds were prepared according to the method described in Example 1(iv) above from 7-methoxy-1-methyltetralin-1-yl-C(O)-Aze-Pab(Z) (0.10 g; 0.18 mmol; from step (iv) above) and Pd/C (10%) in EtOH (10 mL). The crude product was purified using preparative RPLC (CH$_3$CN:0.1M ammonium acetate; 30:70 to 32.5:67.5) yielding two diastereomers. The individual solutions containing the diastereomers were concentrated. Freeze-drying of the solutions yielded the compound obtained from the fastest fraction (Compound 10A; 30 mg; 69%) and the slowest fraction (Compound 10B; 28 mg; 64%).

Compound 10A (Referred to Hereinafter as (R) or (S))

LC-MS (m/z) 435 (M+1)$^+$ $^1$H-NMR (400 MHz; D$_2$O): δ7.74 (d, 2H); 7.49 (d, 2H); 7.10 (d, 1H); 6.85 (dd, 1H); 6.66 (d, 1H); 4.53 (q, 1H); 3.85 (m, 1H); 3.77 (s, 3H); 2.98 (m, 1H); 2.70 (m, 2H); 2.28 (m, 1H); 2.03 (m, 2H); 1.95 (s, 3H); 1.88 (m, 1H); 1.72 (m, 1H); 1.44 (s, 3H)

$^{13}$C-NMR (100 MHz; CDCl$_3$): (carbonyl and/or amidine carbons) δ180.8; 174.1; 167.6; 158.5

Compound 10B (Referred to Hereinafter as (S) or (R))

LC-MS (m/z) 435 (M+1)$^+$ $^1$H-NMR (400 MHz; D$_2$O): δ7.75 (d, 2H); 7.50 (d, 2H); 7.06 (d, 1H); 6.80 (bd, 1H); 6.68 (b, 1H); 4.52 (q, 2H); 3.75 (m, 4H); 2.88 (m, 1H); 2.68 (m, 2H); 2.37 (m, 1H); 1.90 (s, 3H); 2.0–1.6 (m, 4H); 1.41 (s, 3H)

$^{13}$C-NMR (100 MHz; CDCl$_3$): (carbonyl and/or amidine carbons) δ180.9; 174.0; 167.5; 158.4

Example 11

4-Hydroxy-6-methoxychroman-4-yl-C(O)-Aze-Pab× OAc (i) 4-Hydroxy-6-methoxychroman-4-yl-carboxylic acid methyl ester The sub-title compound was prepared according to the method described by Bigge et al (J. Med. Chem. (1993) 36, 1977) from 6-methoxychroman-4-one (1.29 g; 7.23 mmol), Me$_3$SiCN (0.79 g; 8.0 mmol) and ZnI$_2$ (20 mg; cat.). Yield 1.11 g (64%).

$^1$H-NMR (500 MHz; CD$_3$OD): δ6.80 (dd, 1H); 6.73 (d, 1H); 6.72 (s, 1H); 4.28 (m, 1H); 4.14 (dt, 2H); 3.74 (s,3H); 3.70 (s, 3H); 2.47 (m, 1H); 2.02 (m, 1H)

(ii) 4-Hydroxy-6-methoxychroman-4-yl-carboxylic acid

The sub-title compound was prepared according to the method described in Example 1(ii) above from 4-hydroxy-6-methoxychroman-4-yl-carboxylic acid, methyl ester (1.09 g; 4.58 mmol; from step (i) above) and LiOH.H$_2$O (0.39 g; 9.2 mmol). Yield 0.71 g (69%).

LC-MS (m/z) 223 (M+1)$^+$ $^1$H-NMR (300 MHz; CD$_3$OD): δ6.81 (m, 1H); 6.77 (m, 1H); 6.74 (m, 1H); 4.31 (m, 1H); 4.14 (m, 1H); 3.71 (s, 3H); 2.50 (m, 1H); 2.03 (m, 1H)

(iii) 4-Hydroxy-6-methoxychroman-4-yl-C(O)-Aze-Pab(Z)

The sub-title compound was prepared according to the method described in Example 3(i) above from 4-hydroxy-6-methoxychroman-4-yl-carboxylic acid (0.104 g; 0.464 mmol; from step (ii) above), TBTU (0.29 g; 0.90 mmol), DMF (8 mL), DIPEA (80 μL+320 μL; 0.46 mmol+1.84 mmol) and H-Aze-Pab(Z) (0.4 g; 0.91 mmol). The crude product, 0.27 g of a yellow viscous oil, was purified using preparative RPLC (CH$_3$CN:0.1M ammonium acetate 40:60), the fractions of interest were concentrated and extracted with EtOAc. Yield 0.089 g (33%).

LC-MS (m/z) 573 (M+1)$^+$ (iv) 4-Hydroxy-6-methoxychroman-4-yl-C(O)-Aze-Pab×HOAc The title compound was prepared according to the method described in Example 1(iv) above from 4-hydroxy-6-methoxychroman-4-yl-C(O)-Aze-Pab(Z) (0.089 g; 0.155 mmol; from step (iii) above), AcOH (0.25 μL, 0.44 mmol) and Pd/C (5%; 0.089 g). Yield 55.5 mg (72%).

LC-MS (m/z) 439 (M+1)$^+$ $^1$H-NMR (300 MHz; CD$_3$OD): (complex due to diastereomerism/rotamerism) δ7.7–7.5 (m, 2H); 7.5–7.3 (m, 2H); 6.75–6.55 (m, 3H); 4.8 (m, 1H, partly hidden by HDO); 4.5–3.5 (m, 9H, thereof 3.74(s) and 3.69 (s); 2.7–1.7 (m, 7H; thereof 1.95, s, 3H)

$^{13}$C-NMR (75 MHz; CDCl$_3$): (carbonyl and/or amidine carbons) δ176.4; 173.1; 168.1

Example 12

(S)- and (R)-1-Hydroxy-4-methoxyindan-1-yl-C(O)-Aze-Pab (i) 4-Methoxy-1-indanone Cs$_2$CO$_3$ (7 g; 21.5 mmol) followed by CH$_3$I (10 g; 70 mmol) was added to a solution of 4-hydroxy-1-indanone (5.0 g; 34 mmol) in THF (30 mL) and the mixture was stirred at RT for 60 h. The reaction mixture was filtered and concentrated, and the crude product was purified using flash chromatography (SiO$_2$; methylene chloride) to yield 3.1 g (56%) of the sub-title substance.

(ii) 1-Hydroxy-4-methoxyindan-1-yl-carboxylic acid ethyl ester

The sub-title compound was prepared according to a method described by Bigge et al (J. Med. Chem. (1993) 36, 1977) from 4-methoxy-1-indanone (2.2 g; 13.5 mmol; from step (i) above), Me$_3$SiCN (2.0 g; 20 mmol), and ZnI$_2$ (200 mg; 0.62 mmol; cat.). Yield 0.9 g (28%).

$^1$H-NMR (400 MHz; CDCl$_3$): δ7.21 (t, 1H); 6.85 (d, 1H); 6.79 (d, 1H); 4.20 (m, 2H); 3.85 (s, 3H); 3.07 (m,3H); 2.97 (m, 1H); 2.67 (m, 1H); 2.27 (m, 1H); 1.20 (t, 3H)

(iii) 1-Hydroxy-4-methoxyindan-1-yl-carboxylic acid

NaOH (19M; 1.0 mL) was added to a solution of 1-hydroxy-4-methoxyindan-1-yl-carboxylic acid ethyl ester (0.90 g; 3.8 mmol; from step (ii) above) in EtOH (20 mL) and the solution was stirred for 30 minutes. Brine (40 mL) was added and the mixture was washed with EtOAc, cautiously made acidic to pH 2 (HCl; 2M), and the aqueous solution was extracted with EtOAc. The organic layer was washed with brine, dried (Na$_2$SO$_4$) and concentrated, yielding 0.70 g (88%) of the sub-title substance.

$^1$H-NMR (400 MHz; CDCl$_3$): δ7.23 (t, 1H); 6.89 (d, 1H); 6.81 (d, 1H); 3.85 (s, 3H); 3.0 (m, 2H); 2.77 (m, 1H); 2.3 (m, 1H)

(iv) 1-Hydroxy-4-methoxyindan-1-yl-C(O)-Aze-Pab(Z)

The sub-title compound was prepared according to the method described in Example 4(iv) above from 1-hydroxy-4-methoxyindan-1-yl-carboxylic acid (350 mg; 1.68 mmol; from step (iii) above), methylene chloride (25 mL), H-Aze-Pab(Z) (750 mg; 1.7 mmol), TBTU (600 mg; 1.8 mmol) and DIPEA (770 mg; 1.8 mmol). The mixture was concentrated, and the remainder was purified using flash chromatography (Si-gel; acetone:EtOAc), yielding 350 mg (37.5%).

$^1$H-NMR (400 MHz; CDCl$_3$) (complex due to diastereomers/rotamers) δ8.05 (t, 0.5H, rotamer); 7.95 (t, 0.5H, rotamer); 7.82 (dd, 2H); 7.45 (d, 2H); 7.35 (m, 5H); 7.20 (m, 1H); 6.82 (m, 2H); 4.92 (m, 1H); 4.48 (m, 2H); 3.84 (s, 3H); 3.66 (m, 2H); 3.30 (m, 1H); 2.95 (m, 1H); 2.55 (m, 1H); 2.46 (m, 1H); 30 2.30 (m, 1H)

(v) (S)- and (R)-1-Hydroxy-4-methoxyindan-1-yl-C(O)-Aze-Pab

Ammonium formate (1.0 g; 16 mmol) and Pd/C (5%; 200 mg) were added to a solution of 1-hydroxy-4-methoxyindan-1-yl-C(O)-Aze-Pab(Z) (340 mg; 0.61 mmol; from step (iv) above) in MeOH (30 mL). Formic acid (200 mg; 4.4 mmol) was added and the mixture was stirred for 30 minutes. The reaction mixture was filtered through Hyflo and the solution was concentrated. The crude product was purified using preparative RPLC (CH$_3$CN:0.1M ammonium acetate; 15:85). The fractions of interest were collected and concentrated, and the water solution was freeze dried, yielding a faster moving fraction (Compound 12A; 50 mg; 34%) and a slower moving fraction (Compound 12B; 5 mg; 3.4%).

Compound 12A (Referred to Hereinafter as (R) or (S))

LC-MS (m/z) 423 (M+1)$^+$ $^1$H-NMR (400 MHz; CD$_3$OD): (complex due to rotamerism) δ7.74 (d, 2H, minor rotamer); 7.70 (d, 2H, major rotamer); 7.60 (d, 2H, minor rotamer); 7.48 (d, 1H, major rotamer); 7.20 (t, 1H); 6.95 (d, 1H, major rotamer); 6.87 (d, 1H, minor rotamer); 6.84 (d, 1H, major rotamer); 6.83 (d, 1H, minor rotamer); 4.82 (m, 1H); 4.5 (m, 1H); 4.6–4.4 (m, 2H); 4.11 (m,1H, major rotamer); 4.00 (m, 1H, minor rotamer); 3.82 (s, 3H); 3.0 (m, 1H); 2.9 (m, 1H); 2.65 (m, 1H), 2.5 (m, 1H); 2.3–2.0 (m, 2H)

$^{13}$C-NMR (100 MHz; CD$_3$OD): (carbonyl and/or amidine carbons) δ180.3; 176,4; 173.0; 167.9

Compound 12B (Referred to Hereinafter as (S) or (R))

LC-MS (m/z) 423 (M+1)$^+$ $^1$H-NMR (400 MHz; CD$_3$OD): (complex due to rotamerism) δ7.8–7.7 (m, 2H); 7.54 (d, 2H); 7.23 (m, 1H); 6.97 (m, 1H); 6.9–6.8 (m, 1H); 4.80 (m, 1H); 4.6–4.4 (m, 2H); 4.25 (m, 1H); 4.1–3.9 (m, 1H); 3.82 (s, 3H); 3.0–2.85 (m, 2H); 2.8–2.5 (m, 2H); 2.3–2.1 (m, 2H); 1.90 (s, 3H)

Example 13

1-Hydroxy-5-methoxytetralin-1-yl-C(O)-Aze-Pab(OH)

A solution of hydroxylamine×HCl (39 mg; 0.56 mmol) and TEA (0.26 mL; 1.86 mmol) in THF (10 mL) was sonicated at 40° C. for 1 h, whereafter 1-hydroxy-5-methoxytetralin-1-yl-C(O)-Aze-Pab(Z) (53 mg; 0.093 mmol; see Example 5(iii) above) dissolved in a small amount of THF was added, and the mixture was stirred at 40° C. for 3 days. The mixture was concentrated, and the product was purified using preparative RPLC (CH$_3$CN:0.1M ammonium acetate; 30:70). The fractions of interest were concentrated and the remainder was freeze dried. Yield 29 mg (70%).

LC-MS (m/z) 453 (M+1)$^+$ $^1$H-NMR (400 MHz; CD$_3$OD): (complex due to diastereomers/rotamers) δ7.58 (m, 2H); 7.33 (dd, 2H); 7.16 (m, 1H); 7.85 (m, 2H); 4.78 (dd, 2H); 4.44 (m, 2H); 4.2–4.0 (m, 2H); 3.80 (s, 3H); 3.58 (m, 0.5H, rotamer); 3.47 (m, 0.5H, rotamer); 2.91 (bd, 1H); 2.44 (m, 2H); 2.34 (m, 1H); 2.19 (m, 1H); 2.08 (m, 2H); 1.98 (b, 2H); 1.89 (b, 2H)

$^{13}$C-NMR (100 MHz; CDCl$_3$): (carbonyl and/or amidine carbons) δ178.0; 177.8; 172.9, 158.4; 158.2; 155.3

Example 14

(S)- or (R)-1-Hydroxy-7-methoxytetralin-1-yl-C(O)-Aze-Pab(OH)

The title compound was prepared according to the method described in Example 13 above from hydroxylamine×HCl (48 mg; 0.69 mmol), TEA (0.32 mL; 2.31 mmol) and (S)- or (R)-1-hydroxy-7-methoxytetralin-1-yl-C(O)-Aze-Pab(Z) (66 mg; 0.12 mmol; Compound 3A from Example 3(i) above). The mixture was concentrated, and the crude product was purified using preparative RPLC (CH$_3$CN:0.1M ammonium acetate; 28:72) yielding 17 mg (31%). Purity 94.5%, diastereomeric ratio 87:13.

LC-MS (m/z) 453 (M+1)$^+$ $^1$H-NMR (400 MHz; CD$_3$OD): δ5.75 (d, 2H); 7.37 (m, 3H); 7.04 (d, 1H); 6.81 (m, 1H); 4.82 (m, 1H); 4.44 (m, 2H); 4.28 (m, 1H); 4.08 (m, 1H); 3.72 (s, 3H); 3.64 (m, 1H); 2.72 (m, 3H); 2.40 (m, 1H); 2.22 (m, 1H); 2.12 (m, 2H); 1.95 (m, 2H); 1.88 (m, 3H)

$^{13}$C-NMR (100 MHz; CDCl$_3$): (carbonyl and/or amidine carbons) δ177.6; 172.6, 159.4

Example 15

4-Hydroxy-6-methoxychroman-4-yl-C(O)-Aze-Pab (OH)

The title compound was prepared according to the method described in Example 13 above from hydroxylamine×HCl (74 mg; 1.06 mmol), TEA (0.50 mL; 3.6 mmol) and 4-hydroxy-6-methoxychroman-4-yl-C(O)-Aze-Pab(Z) (92 mg; 0.16 mmol; see Example 11(iii) above). The crude product was purified using preparative RPLC (CH$_3$CN:0.1M ammonium acetate; 28:72) yielding 55 mg (75%). Diastereomeric ratio 53:47.

$^1$H-NMR (400 MHz; CDCl$_3$): (complex due to diastereomerism/rotamerism) δ7.65–7.5 (m, 2H); 7.4–7.3 (m, 2H); 6.85–6.65 (m, 3H); 4.81 (m, 1H, partly hidden by HDO); 4.5–3.9 (m, 5H); 3.9–3.6 (m, 4H); 2.8–1.9 (m, 4H)

$^{13}$C-NMR (100 MHz; CDCl$_3$): (carbonyl and/or amidine carbons) δ176.5; 176.2; 172.8; 155.2

Example 16

4-Hydroxy-6-methoxychroman-4-yl-C(O)-Aze-Pab (OMe)

The title compound was prepared according to the method described in Example 3(i) above from 4-hydroxy-6-methoxychroman-4-yl-carboxylic acid (95 mg; 0.42 mmol; see Example 11(ii) above), TBTU (0.26 g; 0.81 mmol), DMF (5 mL), H-Aze-Pab(OMe)×HCl (0.256 g; 0.81 mmol; see Example 4(iii) above) and DIPEA (75+300 μL; 0.42+ 1.68 mmol). The crude product was purified using preparative RPLC (CH$_3$CN:0.1M ammonium acetate; 30:70), yielding 67 mg (37%).

$^1$H-NMR (400 MHz; CDCl$_3$): (complex due to diastereomerism/rotamerism) δ7.65–7.5 (m, 2H); 7.4–7.3 (m, 2H); 6.85–6.7 (m, 3H); 4.80 (m, 1H, hidden by HDO); 4.5–4.0 (m, 5H); 3.81 (s, 3H); 3.75–3.65 (m, 4H); 2.8–1.9 (m, 4H)

$^{13}$C-NMR (100 MHz; CDCl$_3$): (carbonyl and/or amidine carbons; complex due to diastereomerism/rotamerism) δ177.8; 176.5; 176.1; 172.8; 172.6; 155.2; 155.0

Example 17

(S)- or (R)-1-Hydroxy-7-methoxytetralin-1-yl-C(O)-Aze-Pab(C(O)OCH$_2$CCl$_3$)

NaOH (aq; 2M; 0.78 mL), and then 2,2,2-trichloroethyl chloroformate (21 μL; 0.155 mmol), were added to an ice-cold solution of (S)- or (R)-1-hydroxy-7-methoxytetralin-1-yl-C(O)-Aze-Pab×HOAc (70 mg; 0.14 mmol; see Example 3 above) in THF (3 mL), and the mixture was stirred for 3 hours. The reaction mixture was diluted in water and the resultant mixture was extracted 4 times with methylene chloride. The collected organic phase was washed with brine, dried (Na$_2$SO$_4$) and evaporated. Yield 79.8 mg (92.5%).

LC-MS (m/z) 613 (M+1)$^+$ $^1$H-NMR (400 MHz; CDCl$_3$): δ9.42 (b, 1H); 7.98 (t, 1H); 7.83 (d, 2H); 7.30 (b, 1H); 7.29 (d, 2H); 7.06 (d, 1H); 6.84 (dd, 1H); 6.67 (d, 1H); 4.92 (dd, 1H); 4.86 (s, 2H); 4.48 (m, 2H); 4.12 (s, 1H); 3.86 (m, 1H); 3.75 (s, 3H); 3.08 (m, 1H); 2.81 (db, 1H); 2.58 (m, 2H); 2.27 (m, 1H); 1.95 (m, 3H)

$^{13}$C-NMR (100 MHz; CDCl$_3$): (carbonyl and/or amidine carbons) δ178.7; 171.5; 170.1; 164.0

Example 18

(S)- or (R)-1-Hydroxy-7-methoxytetralin-1-yl-C(O)-Aze-Pab(C(O)OCH$_2$CH$_3$)

The title compound was prepared according to the method described in Example 17 above from (S)- or (R)-1-hydroxy-7-methoxytetralin-1-yl-C(O)-Aze-Pab×HOAc (52 mg; 0.10 mmol; see Example 3 above), NaOH (aq; 2M; 0.58 mL), and ethyl chloroformate (9.4 μL; 0.089 mmol). The crude product was purified using preparative RPLC (CH$_3$CN:0.1M ammonium acetate 30:70). Yield 29 mg (69%).

LC-MS (m/z) 509 (M+1)$^+$ $^1$H-NMR (400 MHz; CDCl$_3$): δ9.55 (b, 1H); 7.96 (t, 1H); 7.85 (d, 2H); 7.34 (d, 2H); 7.06 (d, 1H); 6.83 (dd, 1H); 6.68 (d, 1H); 4.94 (dd, 1H); 452 (m, 3H); 4.24 (q, 2H); 3.84 (m, 1H); 3.77 (s, 3H); 3.04 (m, 1H); 2.82 (m, 1H); 2.62 (m, 2H); 2.27 (m, 1H); 2.0–1.85 (m, 5H); 1.37 (t, 3H)

$^{13}$C-NMR (100 MHz; CDCl$_3$): (carbonyl and/or amidine carbons) δ178.9; 171.4. 159.6

Example 19

7-Methoxy-1-allyltetralin-1-yl-C(O)-Aze-Pab× HOAc (i) 7-Methoxy-1-allyltetralin-1-yl-carboxylic acid The sub-title compound was prepared according to the method described in Example 10(ii) above from 7-methoxytetralin-1-yl-carboxylic acid, methyl ester (0.80 g; 3.6 mmol; see Example 10(i) above), NaH (55% in oil; 0.23 mg; 5.4 mmol), and allyl bromide (0.65 g, 5.4 mmol), whereafter the crude product was hydrolysed directly according to the method described in Example 10(iii) above with KOH (3 g) in EtOH:H$_2$O (40 mL; 1:1). Yield 0.39 g (44%).

$^1$H-NMR (400 MHz; CDCl$_3$): δ7.00 (d, 1H); 6.93 (d, 1H); 6.72 (dd, 1H); 5.64 (m, 1H); 5.05 (m, 2H); 3.75 (s, 3H); 2.85–2.60 (m, 4H); 2.20 (m, 2H); 1.95–1.70 (m, 3H)

(ii) Boc-Aze-Pab×HCOOH

The sub-title compound was prepared according to the method described in Example 12(v) above from ammonium formate (3.0 g; 50 mmol), Pd/C (5%; 1.0 g), Boc-Aze-Pab (Z) (4.7 g; 10 mmol; see international patent application WO 94/29336) and formic acid (1.0 g; 22 mmol) in 50 mL of MeOH. The crude product was suspended in CH$_2$C$_2$ (50 mL), filtered and washed with more Ch$_2$Cl$_2$. The solid material was dried and used in the following step without further purification.

(iii) Boc-Aze-Pab(Teoc)

Teoc-p-nitrophenyl carbonate (3.5 g; 12.3 mmol) was added to a solution of Boc-Aze-Pab×HCOOH (3.7 g; 10 mmol; from step (ii) above) in THF (100 mL) whereafter a solution of $K_2CO_3$ (1.8 g; 13 mmol) in water (20 mL) was added over 2 minutes. The resultant solution was stirred for 3 days, concentrated, and the remainder was taken up in EtOAc (150 mL) and NaOH (aq; 0.5M; 50 mL). The organic layer was washed with brine (2×50 mL), dried ($Na_2SO_4$) and concentrated. The crude product was purified using flash chromatography (Si-gel; methylene chloride:acetone; 4:1). Yield 4.6 g (96%).

$^1$H-NMR (500 MHz; $CDCl_3$): δ7.86 (d, 2H); 7.39 (d, 2H); 4.72 (bt, 1H); 4.53 (b, 2H); 3.93 (q, 1H); 3.81 (q, 1H); 2.48 (b, 2H); 1.43 (s, 9H)

(iv) H-Aze-Pab(Teoc)×HCl

A solution of Boc-Aze-Pab(Teoc) (4.6 g; 9.6 mmol; from step (ii) above) in methylene chloride (150 mL) was saturated with dry HCl. The solution was kept at RT in a stoppered flask for 10 minutes, whereafter it was concentrated. Yield 4.2 g (97%).

$^1$H-NMR (400 MHz; $CD_3OD$): δ7.80 (d, 2H); 7.60 (d, 2H); 5.10 (t, 1H); 4.60 (s, 2H); 4.15 (q, 1H); 3.97 (q, 1H); 2.86 (m, 1H); 2.57 (m, 1H)

(v) 7-Methoxy-1-allyltetralin-1-yl-C(O)-Aze-Pab(Teoc)

The sub-title compound was prepared according to the method described in Example 3(i) above from 7-methoxy-1-allyltetralin-1-yl-carboxylic acid(0.30 g; 1.2 mmol; from step (i) above), TBTU (0.43 g; 1.3 mmol), H-Aze-Pab(Teoc) (0.60 g; 1.3 mmol; from step (iv) above) and DIPEA (0.69 g; 5.4 mmol). The crude product was purified using flash chromatography (Si-gel; EtOAc). Yield 0.41 mg (56%).

$^1$H-NMR (500 MHz; $CDCl_3$): (complex due to diastereomerism/rotamerism) δ8.35 (b, 0.5H); 8.20 (bt, 0.5H); 7.90 (d, 1H); 7.85 (d, 1H); 7.90 (d, 1H); 7.35 (d, 1H); 7.01 (t, 1H); 6.75 (m, 1H); 6.65 (d, 0.5H); 6.53 (d, 0.5H); 5.80–5.65 (m, 1H); 5.02 (dd, 1H); 4.96 (m, 1H); 4.87 (dd, 1H); 4.61 (m, 1H); 4.43 (dt, 1H); 4.25 (m, 2H); 3.70 (m+s, 3H); 3.54 (m, 0.5H); 2.95–2.40 (m, 6H); 2.23 (m, 1H); 2.13 (m, 1H); 1.98 (m, 2H); 1.80 (m, 2H); 1.13 (m, 2H); 0.13 (d, 9H)

(vi) 7-Methoxy-1-allyltetralin-1-yl-C(O)-Aze-Pab×HOAc

A solution of $Bu_4NF$ (1M in THF; 0.66 mL) was added to a solution of 7-methoxy-1-allyltetralin-1-yl-C(O)-Aze-Pab (Teoc) (0.36 g; 0.60 mmol; from step (v) above) in THF (40 mL), and the solution was stirred at 60° C. for 24 h. The crude product was purified using preparative RPLC ($CH_3CN$:0.1M ammonium acetate (50:50)) and freeze dried. Yield 0.22 g (71%).

$^1$H-NMR (500 MHz; $CDCl_3$): δ7.77 (dd, 2H); 7.52 (t, 2H); 7.13 (t, 1H); 6.87 (dt, 1H); 6.77 (dd, 1H); 5.71 (m,1H); 5.02 (m, 2H); 4.53 (b, 1H); 3.85– 3.65 (m, 4H); 3.02 (m, 1H); 2.70 (b, 4H); 2.40–2.20 (m, 1H); 2.05–1.70 (b, 8H; thereof 1.92; s)

$^{13}$C-NMR (100 MHz; $D_2O$): (carbonyl and/or amidine carbons) δ179.1; 173.7; 167.3; 158.5

LC-MS (m/z) 459 (M-1)$^-$

Example 20

(S)- or (R)-1-Hydroxy-7-chlorotetralin-1-yl-C(O)-Pro-Pab (i) 7-Amino-1-tetralone Ammonium formate (2 g), Pd/C (5%; 1 g), and formic acid (0.5 g; cat.) were added in that order to a solution of 7-nitro-1-tetralone (1.95 g; 10 mmol) in methanol (50 mL), and the mixture was stirred for 30 minutes. The solution was filtered, and the filtrate was concentrated. The remainder was soaked with methylene chloride (50+25 mL), and the mixture was filtered and concentrated. Yield 1.4 g (88%).

$^1$H-NMR (500 MHz; $CDCl_3$): δ7.32 (d, 1H); 7.03 (d, 1H); 6.83 (dd, 1H); 3.70 (b, 2H); 2.85 (t, 2H); 2.61 (t, 2H); 2.10 (m, 2H)

(ii) 7-Chloro-1-tetralone $NaNO_2$ (0.7 g; 10 mmol) dissolved in water (10 mL) was added with stirring to an ice-cold solution of 7-amino-1-tetralone (1.4 g; 8.8 mmol; from step (i) above) in conc HCl (aq.) over a period of 5 minutes. The resultant cold solution was then added slowly to an ice-cold solution of CuCl (1.5 g, 15 mmol) in conc. HCl (aq.), whereafter the resultant solution was stirred at RT for 2 hours and at 60° C. for 30 minutes. The slurry was cooled with ice, and the resultant precipitate was suction filtered, washed with water, and air dried. Yield 1.50 g (94%).

$^1$H-NMR (500 MHz; $CDCl_3$): δ8.00 (d, 1H); 7.41 (dd, 1H); 7.20 (d, 1H); 2.95 (t, 2H); 2.66 (m, 2H); 2.14 (m, 2H)

(iii) 7-Chloro-1-hydroxytetraline-1-carboxylic acid, ethyl ester

Prepared according to the method described by C.F.Bigge et al in J. Med. Chem (1993) 36, 1977 using 7-chloro-1-tetralone (1.5 g; 8.3 mmol; from step (ii) above), $Me_3Si$-CN (1.0 g; 10 mmol), and $ZnI_2$ (0.3 g). Yield 0.8 g (36%).

$^1$H-NMR (600 MHz; $CDCl_3$): δ7.72 (s, 1H); 7.25 (d, 1H); 7.17 (d, 1H); 7.09 (dd, 1H); 4.35–4.20 (m, 2H); 2.80 (m, 2H); 2.35 (m, 1H); 2.12–1.92 (m, 3H), 1.25 (m, 3H)

(iv) 7-Chloro-1-hydroxytetraline-1-carboxylic acid

NaOH (10M, 1 mL) was added to a solution of 7-chloro-1-hydroxytetraline-1-carboxylic acid, ethyl ester (0.8 g; 3.1 mmol; from step (iii) above) in DMSO (20 mL), and the mixture was heated to 100° C. for 3 hours. The resultant mixture was diluted with crushed ice (40 g) and brine (40 mL), and the mixture was extracted with EtOAc. The aqueous layer was acidified to pH 2 with 2M HCl and extracted with EtOAc (2×40 mL). The combined organic layer was dried ($Na_2SO_4$) and concentrated. Yield 0.22 mg (30%).

$^1$H-NMR (500 MHz; $CDCl_3$): δ7.25 (d, 1H); 7.20 (d, 1H); 7.09 (d, 1H); 2.80 (m, 2H); 2.27 (m, 1H); 2.17–2.00 (m, 2H); 1.98 (m, 1H)

(v) 7-Chloro-1-hydroxytetralin-1-yl-C(O)-Aze-Pab(Z)

HATU (400 mg; 1.05 mmol) was added to a solution of 7-chloro-1-hydroxytetraline-1-carboxylic acid (220 mg; ca 1 mmol; from step (iv) above) in DMF (50 mL) and, after stirring for a short time, a solution of H-Aze-Pab(Z)×2HCl (450 mg; 1.02 mmol) and 2,4,6-trimethylpyridine (425 mg, 3.5 mmol) in DMF (10 mL) was added dropwise. After stirring overnight, the resultant mixture was diluted with an aqueous solution of NaCl (15%; 100 mL) and extracted with EtOAc (2×50 mL). The organic layer was washed with brine (20 mL), dried ($Na_2SO_4$), and concentrated. The remainder was purified using flash chromatography (Si-gel; EtOAc). Yield 300 mg (52%).

$^1$H-NMR (400 MHz; $CDCl_3$): (complex due to diastereomerism and/or rotamerism) δ7.89 (d, 1H); 7.82 (d, 1H); 7.42 (d, 2H); 7.40–7.30 (m, 6H); 7.18 (m, 1H); 7.06 (d, 1H); 5.20 (s, 2H); 4.93 (m, 1H); 4.60–4.40 (m, 3H); 3.83 (m, 0.5H); 3.72 (m, 0.5H); 3.07 (m, 1H); 2.7–2.5 (m, 3H); 2.40 (m, 1H); 2.03–1.80 (m, 5H)

(vi) 7-Chloro-1-hydroxytetralin-1-yl-C(O)-Aze-Pab×HOAc

Anisol (65 mg; 0.6 mmol) and trifluoromethanesulfonic acid (400 mg; 2.6 mmol) were added, in that order, to a solution of 7-chloro-1-hydroxytetralin-1-yl-C(O)-Aze-Pab (Z) (300 mg; 0.52 mmol; from step (v) above) in methylene chloride (20 mL) and the solution was stirred at RT for 10 minutes. Water (20 mL) was added and the organic phase was separated and removed, whereafter the aqueous phase was adjusted to pH 4–5 with saturated $NaHCO_3$ (aq). The solution was partially concentrated and the crude product was purified using preparative RPLC ($CH_3CN$:water; 10:90 to 90:10). The fractions of interest were partially concentrated, a few drops of HOAc (conc.) were added, and the solution was freeze dried. Yield 40 mg (15%).

$^1$H-NMR (500 MHz; CD$_3$OD): δ7.78 (dd, 2H); 7.59 (m, 2H); 7.30 (d, 1h); 7.22 (d, 1H); 7.15 (d, 1H); 4.65–4.35 (m, 3H); 4.20–3.90 (m, 1H); 2.85–2.70 (m, 1H); 2.55 (m, 1H); 2.35–1.95 (m, 9H)

$^{13}$C-NMR (100 MHz; CDCl$_3$): (carbonyl and/or amidine carbons) δ177.0; 172.8; 167.9

Example 21

1-n-Propyl-7-methoxytetralin-1-yl-C(O)-Aze-Pab× HOAc

A small amount of Pd/C (10%) was added to a solution of 1-allyl-7-methoxytetralin-1-yl-C(O)-Aze-Pab×HOAc (80 mg; 0.15 mmol; see Example 19 above) in EtOH (5 mL) and the mixture was hydrogenated at ambient temperature and pressure for 2 h. The mixture was filtered through Celite and the resultant solution was concentrated. Freeze drying from water yielded 68 mg (85%) of the title compound.

$^1$H-NMR (400 MHz; CDCl$_3$): δ7.77 (t, 2H); 7.52 (t, 2H); 7.12 (t, 1H); 6.87 (m, 1H); 6.75 (d, 1H); 4.75 (m, 1H; partially hidden); 4.54 (s, 2H); 3.77 (m, 4H); 3.66 (m, 1H); 3.10 (m, 1H); 2.70 (b, 2H); 2.30 (m, 1H); 2.1–1.6 (m, 10H; thereof 1.91, s, 3H); 1.25 (m, 1H); 1.10 (m, 1H); 0.83 (q, 3H)

LC-MS (m/z) 463 (M+1)$^+$

Example 22

6-Chloro-4-hydroxychroman-4-yl-C(O)-Aze-Pab× HOAc (i) 6-Chloro-4-hydroxychroman-4-yl-carboxylic acid, methyl ester The sub-title compound was prepared according to the method described by Bigge et al (J. Med. Chem (1993) 36, 1977ff) from 6-chlorochromanone (2.45 g; 13.4 mmol), Me$_3$SiCN (1.51 g; 15.2 mmol), and ZnI$_2$ (40 mg; cat.). Yield 0.58 g (18%).

$^1$H-NMR (300 MHz; CDCl$_3$): δ7.17 (d, 1H); 7.08 (d, 1H); 6.82 (d, 1H); 4.41 (m, 1H); 4.37 (m, 1H); 2.47 (m, 1H); 2.09 (m, 1H)

(ii) 6-Chloro-4-hydroxychroman-4-yl-carboxylic acid

LiOH.H$_2$O (0.19 g; 4.6 mmol) and water (4 mL) were added to a solution of 6-chloro-4-hydroxychroman-4-yl-carboxylic acid, methyl ester (0.56 g, 2.3 mmol; from step (i) above) in THF (6 mL). The reaction mixture was stirred at room temperature for 3 h, THF was evaporated and the water solution was washed with methylene chloride. The reaction mixture was acidified with HCl (2M) and extracted with ethyl acetate. The organic layer was dried (Na$_2$SO$_4$) and evaporated, yielding a slowly crystallizing oil. Yield: 490 mg (93%).

LC-MS (m/z) 228 (M−1)$^−$ (iii) 6-Chloro-4-hydroxychroman-4-yl-C(O)-Aze-Pab (Teoc)

A solution of 6-chloro-4-hydroxychroman-4-yl-carboxylic acid (222 mg; 1.00 mmol; from step (ii) above) and HATU (370 mg, 0.97 mmol) in DMF (5 mL) was stirred at 0° C. for 1.5 h, and a mixture of H-Aze-Pab(Teoc)×HCl (440 mg; 0.98 mmol; see Example 19(iv) above) and 2,4, 6-trimethylpyridine (0.48 g; 3.9 mmol) in DMF (5 mL) was added at 0° C. After stirring for 3 h at 0° C., the reaction mixture was concentrated, and the crude product was purified using preparative RPLC (CH$_3$CN:0.1M ammonium acetate (55:45)). The fractions of interest were partly concentrated and extracted with methylene chloride. The organic layer was dried (Na$_2$SO$_4$) and concentrated yielding 350 mg (67%) of a diastereomeric mixture.

$^1$H-NMR (400 MHz; CDCl$_3$): δ7.31 (m, 1H); 7.19 (dt, 1H); 7.09 (d, 0.5H); 7.00 (d, 0.5H); 6.88 (dd, 1H); 4.93 (m, 1H); 4.80 (br, 0.5H); 4.61 (dd, 1H); 4.53–4.43 (m, 2H); 4.36 (m, 1H); 4.15 (t, 1H); 3.89 (m, 0.5H); 3.74 (m, 0.5H); 3.09 n(m, 1H); 2.46–2.28 (m, 1H); 2.21 (m, 1H); 1.96 (m, 1H); 0.06 (s, 9H)

$^{13}$C-NMR (100 MHz; CDCl$_3$): (carbonyl and/or amidine carbons) δ176.9; 171.5; 171.3; 169.8; 155.4; 155.2

LC-MS (m/z) 588 (M+1)$^+$ (iv) 6-Chloro-4-hydroxychroman-4-yl-C(O)-Aze-Pab× HOAc Bu$_4$NF (1.0M in THF; 0.35 mL) was added to a solution of 6-chloro-4-hydroxychroman-4-yl-C(O)-Aze-Pab(Teoc) (190 mg; 0.32 mmol; from step (iii) above) in THF (20 mL) at 0° C. The solution was stirred for two days at 40° C. The solution was concentrated and the crude material was purified using preparative RPLC (CH$_3$CN:0.1M ammonium acetate (25:75)). Yield 115 mg (71%).

$^1$H-NMR (400 MHz; CD$_3$OD): δ7.73 (m, 2H); 7.55 (m, 2H); 7.28 (dd, 1H); 7.15 (m, 1H); 6.79 (m, 1H); 4.60 (m, 1H); 4.47 (m, 2H); 4.33 (m, 1H); 4.15 (m, 2H); 2.8–2.46 (m, 1H); 2.38 (m, 1H); 2.23 (m, 1H); 2.06 (m, 1H); 1.90 (s, 3H)

$^{13}$C-NMR (100 MHz; CDCl$_3$): (carbonyl and/or amidine carbons) δ175.9; 175.6; 174.4; 173.1; 173.0

LC-MS (m/z) 444 (M+1)$^+$

Example 23

4-Hydroxychroman-4-yl-C(O)-Aze-Pab×HOAc

Pd/C (5%; 25 mg) was added to a solution of 6-chloro-4-hydroxychroman-4-yl-C(O)-Aze-Pab×HOAc (14.7 mg; 0.029 mmol; see Example 22 above) in EtOH (5 mL), and the mixture was hydrogenated at ambient temperature and pressure for one day. The mixture was filtered through Celite, and the crude product was purified using preparative RPLC (CH$_3$CN:0.1M ammonium acetate (25:75)). The fractions of interest were concentrated. Freeze drying yielded 4 mg (30%) of the title compound.

$^1$H-NMR (400 MHz; CD$_3$OD): δ7.79 (m, 2H); 7.56 (m, 2H); 7.4–7.2 (m, 2H); 7.00 (m, 2H); 4.96 (dd, 1H); 4.5–4.3 (m, 2H); 4.20 (m, 2H); 3.88 (m, 1H); 2,8–2.4 (m, 2H); 2.27 (m, 1H); 2.17 (m, 1H); 2.07 (s, 3H)

$^{13}$C-NMR (100 MHz; CDCl$_3$): (carbonyl and/or amidine carbons) δ173.7; 167.7

LC-MS (m/z) 409 (M+1)$^+$

Example 24

6,8-Dichloro-4-hydroxychroman-4-yl-C(O)-Aze-Pab×HOAc (i) 6,8-Dichloro-4-hydroxychroman-4-yl-carboxylic acid, methyl ester The sub-title compound was prepared according to the method described by Bigge et al (J. Med. Chem. (1993) 36, 1977ff) from 6,8-dichlorochromanone (1.36 g; 6.27 mmol), Me$_3$SiCN (0.68 g; 6.9 mmol), and Znl$_2$ (20 mg; cat.). Yield 0.52 g (30%).

$^1$H-NMR (300 MHz; CDCl$_3$): δ7.30 (s, 1H); 7.00 (s, 1H); 4.53 (m, 1H); 4.33 (m, 1H); 3.83 (s, 3H); 2.47 (m, 1H); 2.12 (m, 1H)

(ii) 6,8-Dichloro-4-hydroxychroman-4-yl-carboxylic acid

LiOH.H$_2$O (0.15 g; 3.6 mmol) and water (2 mL) were added to a solution of 6,8-dichloro-4-hydroxychroman-4-yl-carboxylic acid, methyl ester (0.50 g; 1.8 mmol; from step (i) above) in THF (5 mL). The resultant mixture was stirred at room temperature for 30 min., THF was evaporated and the water phase was washed with methylene chloride. The reaction mixture was made acidic with HCl (2M) and extracted with methylene chloride. The organic layer was dried ($Na_2SO_4$) and evaporated, yielding the sub-title compound. Yield: 390 mg (83%).

LC-MS (m/z) 262 (M−1)

(iii) 6,8-Dichloro-4-hydroxychroman-4-yl-C(O)-Aze-Pab (Teoc)

The sub-title compound was prepared according to a method described in Example 22(iii) above from 6,8-dichloro-4-hydroxychroman-4-yl-carboxylic acid (100 mg; 0.38 mmol; from step (ii) above), HATU (160 mg; 0.42 mmol), H-Aze-Pab(Teoc)×HCl, (190 mg; 0.42 mmol; see Example 19(iv) above), and 2,4,6-trimethylpyridine (0.19 g; 1.6 mmol). The crude product was purified using preparative RPLC ($CH_3CN$:0.1M ammonium acetate (55:45)). The fractions of interest were partly concentrated and extracted with methylene chloride. The organic layer was dried ($Na_2SO_4$) and concentrated yielding 206 mg (87%) of a diastereomeric mixture.

LC-MS (m/z) 623 (M+1)$^+$ (iv) 6,8-Dichloro-4-hydroxychroman-4-yl-C(O)-Aze-Pab× HOAc The title compound was prepared according to the method described in Example 19(vi) above from 6,8-dichloro-4-hydroxychroman-4-yl-C(O)-Aze-Pab(Teoc) (150 mg; 0.24 mmol; from step (iii) above) and $Bu_4NF$ (0.10 g, 0.32 mmol). The crude material was purified using preparative RPLC ($CH_3CN$:0.1M ammonium acetate (30:70)). Yield 45 mg (35%).

$^1$H-NMR (400 MHz; $CD_3OD$): δ7.73 (m, 2H); 7.54 (m, 2H); 7.32 (m, 2H); 7.23 (d, 1H); 4.65–4.40 (m, 4H); 4.30 (m, 2H); 4.17–3.97 (m, 1H); 2.8–2.5 (m, 1H); 2.40 (m, 1H); 2.35–2.20 (m, 1H); 2.15 (m, 2H); 1.95 (s, 3H)

$^{13}$C-NMR (100 MHz; $CDCl_3$): (carbonyl and/or amidine carbons) δ175.4; 174.0; 174.3; 173.0; 168.1

LC-MS (m/z) 477 (M+1)$^+$

Example 25

6-Fluoro-4-hydroxychroman-4-yl-C(O)-Aze-Pab× HOAc (i) 6-Fluoro-4-hydroxychroman-4-yl-carboxylic acid, methyl ester The sub-title compound was prepared according to the method described by Bigge et al (J. Med. Chem. (1993), 36, 1977ff) from 6-fluorochromanone (2.53 g; 15.2 mmol), $Me_3SiCN$ (1.66 g; 16.7 mmol), and $ZnI_2$ (3 mg; cat.). Yield 2.51 g (73%).

$^1$H-NMR (400 MHz; $CDCl_3$): δ6.93 (m, 1H); 6.82 (m, 2H); 4.34 (m, 1H); 4.23 (dt, 1H); 3.81 (s, 3H); 2.47 (m, 1H); 2.10 (m, 1H)

(ii) 6-Fluoro-4-hydroxychroman-4-yl-carboxylic acid

A solution of $LiOH.H_2O$ (0.95 g; 22.6 mmol) in water (30 mL) was added to a solution of 6-fluoro-4-hydroxychroman-4-yl-carboxylic acid, methyl ester (2.47 g; 10.9 mmol; from step (i) above) in THF (10 mL). The reaction mixture was stirred at room temperature for 2 days, THF was evaporated and the water phase was acidified with HCl (2M) and extracted with ethyl acetate. The organic layer was dried ($Na_2SO_4$) and evaporated, yielding the sub-title compound. Yield: 1.41 g (61%).

LC-MS (m/z) 211 (M−1)

(iii) 6-Fluoro-4-hydroxychroman-4-yl-C(O)-Aze-Pab(Z)

The sub-title compound was prepared according to the method described in Example 22(iii) above from 6-fluoro-4-hydroxychroman-4-yl-carboxylic acid (250 mg; 1.18 mmol; from step (ii) above), HATU (500 mg; 1.32 mmol), H-Aze-Pab(Z)×HCl (570 mg; 1.3 mmol; prepared according to the method described in International Patent Application WO 97/02284) and 2,4,6-trimethylpyridine (0.70 g; 5.3 mmol). The crude product was purified using preparative RPLC ($CH_3CN$:0.1M ammonium acetate; 55:45). The fractions of interest were partly concentrated and extracted with methylene chloride. The organic layer was dried ($Na_2SO_4$) and concentrated yielding 290 mg (40%) of a diastereomeric mixture.

FAB-MS (m/z) 561 (M+1)$^+$ (iv) 6-Fluoro-4-hydroxychroman-4-yl-C(O)-Aze-Pab× HOAc HOAc (80 μL) and Pd/C (5%; 93 mg) were added to a solution of 6-fluoro-4-hydroxychroman-4-yl-C(O)-Aze-Pab(Z) (140 mg; 0.25 mmol; from step (iii) above) in EtOH (10 mL), and the mixture was hydrogenated at ambient temperature and pressure for 4 h. The mixture was filtered through Celite. The solution was concentrated and the crude material was purified using preparative RPLC ($CH_3CN$:0.1M ammonium acetate (20:80)). Yield 72 mg (59%).

$^1$H-NMR (400 MHz; $D_2O$): δ7.78 (dd, 1H); 7.73 (d, 1H); 7.55 (m, 2H); 7.18–6.96 (m, 3H); 4.96 (dd, 1H); 4.58 (s, 1H); 4.50–4.35 (m, 2H); 4.19 (m, 2H); 2.63 (m, 1H); 2.45 (m, 1H); 2.35–2.12 (m, 2H); 1.98 (s, 3H)

$^{13}$C-NMR (100 MHz; $D_2O$): (carbonyl and/or amidine carbons) δ176.1; 175.9; 174.7; 173.7; 167.6

Example 26

4-Hydroxy-6-methylchroman-4-yl-C(O)-Aze-Pab× HOAc (i) 4-Hydroxy-6-methylchroman-4-yl-carboxylic acid. methyl ester The sub-title compound was prepared according to a method described by Bigge et al (J. Med. Chem. (1993) 36, 1977ff) from 6-methylchromanone (3.11 g; 19.2 mmol), $Me_3SiCN$ (2.1 g; 21.2 mmol), and $ZnI_2$ (20 mg; cat.). Yield 2.80 g (62%).

$^1$H-NMR (300 MHz; $CDCl_3$): δ7.01 (dd, 1H); 6.89 (d, 1H); 6.77 (d, 1H); 4.37 (dt, 1H); 4.32–4.20 (m, 3H); 2.49 (m, 2H); 2.34 (s, 3H); 2.08 (m, 1H); 1.24 (t, 3H)

(ii) 4-Hydroxy-6-methylchroman-4-yl-carboxylic acid

A solution of $LiOH.H_2O$ (0.78 g; 18.6 mmol) in water (15 mL) was added to a solution of 4-hydroxy-6-methylchroman-4-yl-carboxylic acid, methyl ester (2.2 g; 9.3 mmol; from step (i) above) in THF (10 mL). The reaction mixture was stirred at room temperature overnight, THF was evaporated and the water phase was washed with ether. The resultant solution was acidified with HCl (2M) and extracted with ether. The organic layer was dried ($Na_2SO_4$) and evaporated, yielding the sub-title compound. Yield: 1.21 mg (62%).

$^1$H-NMR (300 MHz; $CD_3OD$): δ7.06 (d, 1H); 6.98 (d, 1H); 6.69 (d, 1H); 4.32 (m, 1H); 4.17 (m, 1H); 2.50 (m, 1H); 2.21 (s, 3H); 2.03 (m, 1H)

LC-MS (m/z) 207 (M−1)

(iii) 4-Hydroxy-6-methylchroman-4-yl-C(O)-Aze-Pab(Z)

The sub-title compound was prepared according to a method described in Example 22(iii) above from 4-hydroxy-6-methylchroman-4-yl-carboxylic acid (310 mg; 1.49 mmol; from step (ii) above), HATU (620 mg; 1.63 mmol), H-Aze-Pab(Z), (790 mg; 2.2 mmol; prepared according to the method described in International Patent Application WO 97/02284) and 2,4,6-trimethylpyridine (0.37 g; 3.0 mmol). The crude product was purified using preparative RPLC ($CH_3CN$:0.1M ammonium acetate (45:55)). The fractions of interest were partly concentrated and extracted with methylene chloride. The organic layer was dried ($Na_2SO_4$) and concentrated yielding 675 mg (81%) of a diastereomeric mixture.

LC-MS (m/z) 557 (M+1)$^+$ (iv) 4-Hydroxy-6-methylchroman-4-yl-C(O)-Aze-Pab×HOAc

HOAc (80 μL) and Pd/C (5%, 150 mg) were added to a solution of 4-hydroxy-6-methylchroman-4-yl-C(O)-Aze-Pab(Z) (240mg; 0.43mmol; from step (iii) above) dissolved in EtOH (10 mL), and the mixture was hydrogenated at ambient temperature and pressure overnight. The mixture was filtered through Celite. Freeze drying gave the title compound in a yield of 159 mg (76%).

$^1$H-NMR (500 MHz; CD$_3$OD): δ7.72 (dd, 2H); 7.53 (dd, 2H); 7.08 (d, 1H); 7.00 (d, 1H); 6.71 (d, 1H); 4.84 (m, partly hidden); 4.60 (m, 1H); 4.46 (m, 1H); 4.29 (m, 2H); 4.14 (t, 1H); 2.40 (m, 2H); 2.26–2.10 (m, 3H); 2.00 (m, 1H); 1.90 (s, 3H)

$^{13}$C-NMR (100 MHz; CD$_3$OD): (carbonyl and/or amidine carbons) δ176.6; 174.5; 173.1; 168.1

LC-MS (m/z) 423 (M+1)$^+$

Example 27

8-Chloro-4-hydroxy-6-methoxychroman-4-yl-C(O)-Aze-Pab×HOAc (i) Ethyl 3-(2-chloro-4-methoxyphenoxy)propionate Sodium (0.055 g; 2.4 mmol) and ethanol (1.5 mL) was added to a melt of 2-chloro-4-methoxyphenol (5.20 g; 32.8 mmol). When all the sodium was dissolved, ethyl acrylate (4.1 g; 41 mmol) was added and the mixture was heated at 105° C. for 7 days. The mixture was then cooled to RT and partitioned between ether and water. The mixture was made acidic with HCl (2M; aq.) and extracted with ether three times. The combined organic layer was washed with NaOH (2M; aq), dried (CaCl$_2$) and evaporated. The crude product (2.7 g) was purified using preparative RPLC (CH$_3$CN:0.1M ammonium acetate (60:40)). Yield 1.90 g (22%).

(ii) 3-(2-Chloro-4-methoxyphenoxy)propionic acid

A solution of LiOH.H$_2$O (0.67 g; 16 mmol) in water (20 mL) was added to a solution of ethyl 3-(2-chloro-4-methoxyphenoxy)propionate (1.90 g; 7.3 mmol; from step (i) above) in THF (10 mL). The reaction mixture was stirred at RT overnight, THF was evaporated and the water phase was washed with ether. The resultant solution was acidified with HCl (2M) and extracted with ether. The organic layer was dried (Na$_2$SO$_4$) and evaporated yielding 0.90 g (54%) of the sub-title compound.

LC-MS (m/z) 229 (M-1)[31]

(iii) 8-Chloro-6-methoxychroman-4-one

Phosphorous pentachloride (1.3 g; 6.2 mmol) was added to a suspension of 3-(2-chloro-4-methoxyphenoxy)propionic acid (0.85 g; 3.7 mmol; from step (ii) above) in benzene (10 mL). The resultant clear solution was heated quickly to boiling and then cooled on an ice bath. Aluminium chloride (1.5 g; 11 mmol) was added in portions and, after complete addition, ice water was added. Extraction with ether, washing of the organic layer with NaHCO$_3$/aq. and NaOH (2M; aq.), drying (Na$_2$SO$_4$) and concentration yielded 0.73 g (93%) of the sub-title compound.

$^1$H-NMR (300 MHz; CDCl$_3$): δ7.27 (d, 1H); 7.19 (d, 2H); 4.59 (t, 2H); 3.80 (s, 3H); 2.81 (t, 2H)

(iv) 8-Chloro-4-hydroxy-6-methoxychroman-4-yl-carboxylic amide

The sub-title compound was obtained during an attempt to prepare the corresponding methyl ester according to the method described by Bigge et al (J. Med. Chem. (1993) 36, 1977ff) from 8-chloro-6-methoxychromanone (0.73 g; 3.4 mmol; from step (iii) above), Me$_3$SiCN (0.94 g; 7.6 mmol), and ZnI$_2$ (50 mg; cat.). The crude product consisted of a minor amount of the corresponding methyl ester and a major amount of the amide. The amide was purified by preparative RPLC (CH$_3$CN:0.1M ammonium acetate; 30:70 to 70:30). Yield 0.39 g (44%).

LC-MS (m/z) 256 (M-1)[31]

(v) 8-Chloro-4-hydroxy-6-methoxychroman-4-yl-carboxylic acid

KOH (1.2 g; 21 mmol) and water (25 mL) were added to a solution of 4-hydroxy-8-chloro-6-methoxychroman-4-yl-carboxylic amide (0.39 g; 1.5 mmol; from step (iv) above) in i-PrOH (25 mL). The reaction mixture was refluxed overnight, i-PrOH was evaporated and the water solution was washed with ether. The reaction mixture was acidified with HCl (2M) and extracted with ethyl acetate. The organic layer was dried (Na$_2$SO$_4$) and evaporated. Yield: 0.38 mg (97%).

LC-MS (m/z) 257 (M-1)[31]

(vi) 8-Chloro-4-hydroxy-6-methoxychroman-4-yl-C(O)-Aze-Pab(Teoc)

The sub-title compound was prepared according to the method described in Example 22(iii) above from 4-hydroxy-8-chloro-6-methoxychroman-4-yl-carboxylic acid (260 mg; 1.00 mmol; from step (v) above), HATU (420 mg; 1.1 mmol), H-Aze-Pab(Teoc)×HCl (490 mg; 1.1 mmol; see Example 19(iv) above), and 2,4,6-trimethylpyridine (600 mg; 4.5 mmol). The crude product was purified using preparative RPLC (CH$_3$CN:0.1M ammonium acetate (55:45)). The fractions of interest were partly concentrated and extracted with methylene chloride. The organic layer was dried (Na$_2$SO$_4$) and concentrated, yielding 340 mg (55%) of a diastereomeric mixture.

LC-MS (m/z) 617 (M+1)$^+$ (vii) 8-Chloro-4-hydroxy-6-methoxychroman-4-yl-C(O)-Aze-Pab×HOAc The title compound was prepared according to the method described in Example 19(vi) above using 4-hydroxy-8-chloro-6-methoxychroman-4-yl-C(O)-Aze-Pab(Teoc) (150 mg; 0.24 mmol; from step (vi) above) and Bu$_4$NF (1.0M in THF; 0.32 mL). The crude material was purified using preparative RPLC (CH$_3$CN:0.1M ammonium acetate (20:80)). Yield 113 mg (87%).

$^1$H-NMR (400 MHz; CD$_3$OD): δ7.69 (d, 2H); 7.54 (d, 2H); 6.90 (d, 1H); 6.85 (d, 1H); 4.57 (m, 3H); 4.48–4.30 (m, 4H); 4.17 (m, 2H); 4.00 (m, 1H); 2.8–2.5 (m, 2H); 2.40 (m, 2H); 2.26 (m, 1H); 2.15 (m, 2H); 2.06 (d, 1H)

LC-MS (m/z) 473 (M-1)[31]

Example 28

6-Chloro-4-hydroxy-8-methylchroman-4-yl-C(O)-Aze-Pab×HOAc (i) Ethyl 3-(4-chloro-2-methylphenoxy)propionate The sub-title compound was prepared according to the method described in Example 27(i) above from 4-chloro-2-methylphenol (4.99 g; 35.0 mmol), sodium (0.055 g; 2.4 mmol), ethanol (1.5 mL) and ethyl acrylate (4.1 g; 41 mmol). The crude product (1.98 g; 23%) was used for the next step without further purification.

(ii) 3-(4-Chloro-2-methylphenoxy)propionic acid

A solution of LiOH.H$_2$O (0.50 g; 12 mmol) in water (10 mL) was added to a solution of ethyl 3-(4-chloro-2-methylphenoxy)propionate (1.98 g; 8.15 mmol; from step (i) above) in THF (20 mL). The reaction mixture was stirred at room temperature overnight, THF was evaporated and the water phase was washed with ether. The resultant solution was acidified with HCl (2M), whereafter a solid material precipitated. The product was filtered and air-dried yielding 0.62 g (35%) of the sub-title compound.

LC-MS (m/z) 213 (M-1)$^-$ (iii) 6-Chloro-8-methylchroman-4-one

Phosphorous pentachloride (0.95 g, 4.6 mmol) was added to a suspension of 3-(4-chloro-2-methylphenoxy)propionic acid (0.59 g; 2.7 mmol; from step (ii) above) in benzene (10 mL). The resultant clear solution was heated quickly to boiling and then cooled on an ice bath. Aluminium chloride (1.0 g; 7.5 mmol) was added in portions and, after complete addition, ice water was added. Extraction with ether, washing of the organic layer with NaHCO$_3$/aq. and NaOH (2M; aq.), drying (Na$_2$SO$_4$) and concentration yielded 0.27 g (50%) of the sub-title compound.

$^1$H-NMR (500 MHz; CDCl$_3$): δ7.70 (d, 1H); 7.29 (d, 2H); 4.56 (t, 2H); 2.79 (t, 2H); 2.22 (s, 3H)

(iv) 6-Chloro-4-hydroxy-8-methylchroman-4-yl-carboxylic amide

The sub-title compound was prepared as described in Example 27(iv) above, using the method described by Bigge et al (J. Med. Chem. (1993) 36, 1977ff) from 6-chloro-8-methylchromanone (0.27 g; 1.37 mmol; from step (iii) above), Me$_3$SiCN (0.29 g; 1.52 mmol), and ZnI$_2$ (46 mg; cat.). The crude product consisted of a minor amount of the corresponding methyl ester and a major amount of the amide. The amide was purified by preparative RPLC (CH$_3$CN:0.1M ammonium acetate; 30:70 to 70:30). Yield: 0.17 g (50%).

LC-MS (m/z) 240 (M−1)[31]

(v) 6-Chloro-4-hydroxy-8-methylchroman-4-yl-carboxylic acid KOH (1.25 g; 22.3 mmol) and water (20 mL) were added to a solution of 4-hydroxy-6-chloro-8-methylchroman-4-yl-carboxylic amide (0.17 g; 0.69 mmol; from step (iv) above) in i-PrOH (20 mL). The reaction mixture was refluxed overnight, i-PrOH was evaporated and the water solution was washed with ether. The reaction mixture was acidified with HCl (2M) and extracted with ethyl acetate. The organic layer was dried (Na$_2$SO$_4$) and evaporated. Yield: 0.13 g (78%).

(vi) 6-Chloro-4-hydroxy-8-methylchroman-4-yl-C(O)-Aze-Pab(Teoc)

A solution of 6-chloro-4-hydroxy-8-methylchroman-4-yl-carboxylic acid (130 mg; 0.54 mmol; from step (v) above) and HATU (220 mg; 0.59 mmol) in DMF (5 mL) was stirred at 0° C. for 1.5 h, and a mixture of H-Aze-Pab(Teoc)×HCl (270 mg; 0.59 mmol; see Example 19(iv) above) and 2,4,6-trimethylpyridine (320 mL; 2.4 mmol) in DMF (3 mL) was added at 0° C. After stirring for 3 h at 0° C. the reaction mixture was concentrated, and the crude product was purified using preparative RPLC (CH$_3$CN:0.1M ammonium acetate (55:45)). The fractions of interest were partly concentrated and extracted with methylene chloride. The organic layer was dried (Na$_2$SO$_4$) and concentrated, yielding 79 mg (24%) of a diastereomeric mixture.

LC-MS (m/z) 601 (M−1)[31]

(vii) 6-Chloro-4-hydroxy-8-methylchroman-4-yl-C(O)-Aze-Pab×HOAc Bu$_4$NF (1.0M in THF; 0.20 mL) was added to a solution of 6-chloro-4-hydroxy-8-methylchroman-4-yl-C(O)-Aze-Pab(Teoc) (79 mg; 0.13 mmol; from step (vi) above) in THF (5 mL) at 0° C. The solution was stirred at 60° C. overnight, and was subsequently concentrated. The crude material was purified using preparative RPLC (CH$_3$CN:0.1 M ammonium acetate (20:80)).

Yield 37 mg (54%).

$^1$H-NMR (400 MHz; CD$_3$OD): δ7.72 (m, 2H); 7.54 (m, 2H); 7.15–6.98 (m, 2H); 4.60 (m, 1H); 4.5–4.3 (m, 3H); 4.25–4.10 (m, 2H); 4.03 (m, 1H); 2.80–2.45 (m, 1H); 2.37 (m, 1H); 2.26 (m, 1H); 2.14 (s, 3H); 2.05 (d, 1H); 1.92 (s, 3H)

LC-MS (m/z) 473 (M−1)[31]

Example 29

(S)- or (R)-1-Hydroxy-7-methoxytetralin-1-yl-C(O)-Aze-Pab(O-C(O)-i-Pr)

2-Methylpropanoic anhyride (7.3 mg; 46 μmol) was added to an ice-cold solution of (S)- or(R)-1-hydroxy-7-methoxytetralin-1-yl-C(O)-Aze-Pab(OH) (20 mg; 44 μmol; see Example 14 above) and Et$_3$N (4.9 mg; 49 μmol) in methylene chloride (1 mL), and the mixture was stirred at RT overnight. The mixture was diluted with a further amount of methylene chloride, washed 3 times with water and once with brine, dried (Na$_2$SO$_4$) and concentrated. The crude product was purified using preparative RPLC (CH$_3$CN:0.1M ammonium acetate (40:60)), and the fractions of interest were concentrated. Freeze drying yielded 13 mg (56%) of the title compound.

$^1$H-NMR (300 MHz; CDCl$_3$): δ7.90 (m, 1H); 7.65 (d, 2H); 7.29 (d, 2H); 7.05 (d, 1H); 6.83 (dd, 1H); 6.67 (d, 1H); 5.13 (b, 2H); 4.93 (dd, 1H); 4.48 (m, 3H); 3.84 (m, 1H); 3.76 (s, 3H); 3.03 (m, 1H); 2.85–2.70 (m, 2H); 2.5–2.7 (m, 2H); 2.25 (m, 1H); 2.00–1.93 (m, 4H); 1.29 (d, 6H)

$^{13}$C-NMR (75 MHz; CDCl$_3$): (carbonyl and/or amidine carbons) δ177.7; 174.3; 170.3

LC-MS (m/z) 523 (M+1)$^+$

Example 30

(S)- or (R)-1-Hydroxy-7-methoxytetralin-1-yl-C(O)-Aze-Pab(O-C(O)-Et)

Propanoic anhydride (9.5 mg; 73 μmol) was added to an ice-cold solution of (S)- or (R)-1-hydroxy-7-methoxytetralin-1-yl-C(O)-Aze-Pab(OH) (30 mg; 66 μmol; see Example 14 above) and Et$_3$N (7.4 mg; 73 μmol) in methylene chloride (1 mL). The mixture was stirred at RT overnight. The crude product was purified using preparative RPLC (CH$_3$CN:0.1M ammonium acetate; 30:70 to 40:60) and the fractions of interest were concentrated. Freeze drying yielded 19 mg (56%) of the title compound.

$^1$H-NMR (400 MHz; CDCl$_3$): δ7.93 (t, 1H); 7.67 (d, 2H); 7.32 (d, 2H); 7.06 (d, 1H); 6.83 (dd, 1H); 6.68 (d, 1H); 5.12 (b, 2H); 4.93 (dd, 1H); 4.50 (m, 2H); 3.84 (m, 1H); 3.76 (s, 3H); 3.03 (m, 1H); 2.67–2.50 (m, 2H); 2.5–2.7 (m, 4H); 2.26 (m, 1H); 1.92 (m, 4H); 1.26 (t, 3H)

$^{13}$C-NMR (100 MHz; CDCl$_3$): (carbonyl and/or amidine carbons) δ178.8; 173.1; 171.4

LC-MS (m/z) 509 (M+1)$^+$

Example 31

(S)- or (R)-1-Hydroxy-7-methoxytetralin-1-yl-C(O)-Aze-Pab(O-C(O)-Ch)

Cyclohexanecarboxylic chloride (7.3 mg; 46 μmol) was added to an ice-cold solution of (S)- or (R)-1-hydroxy-7-methoxytetralin-1-yl-C(O)-Aze-Pab(OH) (30 mg; 66 μmol; see Example 14 above) and Et$_3$N (7 mg; 73 μmol) in methylene chloride (1 mL). The mixture was stirred at RT overnight. The mixture was diluted with a further amount of methylene chloride, and the mixture was washed 3 times with water and once with brine, dried (Na$_2$SO$_4$) and concentrated. The crude product was purified using preparative RPLC (CH$_3$CN:0.1M ammonium acetate (40:60)) and the fractions of interest were concentrated. Freeze drying yielded 18 mg (50%) of the title compound.

$^1$H-NMR (400 MHz; CDCl$_3$): δ7.91 (t, 1H); 7.67 (d, 2H); 7.30 (d, 2H); 7.06 (d, 1H); 6.83 (m, 1H); 6.67 (d, 1H); 5.09

(b, 2H); 4.93 (dd, 1H); 4.50 (m, 3H); 3.83 (m, 1H); 3.76 (s, 3H); 3.02 (q, 1H); 2.68–2.45 (m, 3H); 2.26 (m, 1H); 2.1–1.9 (m, 6H); 1.83 (m, 2H); 1.70 (m, 1H); 1.59 (m, 2H); 1.32 (m, 3H)

$^{13}$C-NMR (100 MHz; CDCl$_3$): (carbonyl and/or amidine carbons) δ178.7; 174.2; 171.4

LC-MS (m/z) 563 (M+1)$^+$

Example 32

(S)- or (R)-1-Hydroxy-7-methoxytetralin-1-yl-C(O)-Aze-Pab(O-allyl)

(i) (S)- or (R)-1-hydroxy-7-methoxytetralin-1-yl-C(O)-Aze-Pab(Teoc)

The sub-title compound was prepared according to the method described in Example 22(iii) above from 1-hydroxy-7-methoxytetralin-1-yl-carboxylic acid (0.44 g; 2.0 mmol; see Example 1(ii) above), HATU (0.80 g; 2.1 mmol), H-Aze-Pab(Teoc)×HCl, (1.17 g; 2.6 mmol; see Example 19(iv) above) and 2,4,6-trimethylpyridine (1.2 g; 10 mmol). The crude product (1.73 g) was purified using preparative RPLC (CH$_3$CN:0.1M ammonium acetate; 55:45 to 45:55). The fractions of interest were partly concentrated and extracted with methylene chloride. The organic layer was dried (Na$_2$SO$_4$) and concentrated yielding 0.32 g (28%) of a diastereomeric mixture. Preparative RPLC (CH$_3$CN:0.1M ammonium acetate (46:54)) yielded two diastereomers: Compound 32A (faster moving diastereomer; 0.16 g; 28%) and Compound 32B (slower moving diastereomer; 0.16 g; 28%).

Compound 32A
$^1$H-NMR (400 MHz; CDCl$_3$): δ7.96 (t, 1H); 7.86 (dd, 2H); 7.36 (dd, 2H); 7.07 (d, 1H); 6.87 (dd, 1H); 6.68 (d, 1H); 4.95 (dd, 1H); 4.54 (m, 3H); 4.26 (m, 2H); 3.84 (m, 1H); 3.78 (s, 3H); 3.04 (q, 1H); 2.83 (d, 1H); 2.63 (m, 2H); 2.28 (m, 1H); 2.02–1.85 (m, 4H); 1.15 (dt, 2H); 0.08 (s, 9H)

LC-MS (m/z) 581 (M+1)$^+$ (ii) (S)- or (R)-1-Hydroxy-7-methoxytetralin-1-yl-C(O)-Aze-Pab(Teoc)(O-allyl)

O-Allylhydroxylamine×HCl (57 mg; 0.52 mmol) was added to a solution of (S)- or (R)-1-hydroxy-7-methoxytetralin-1-yl-C(O)-Aze-Pab(Teoc) (50 mg; 86 μmol; Compound 32A from step (i) above) in THF (3 mL), and the mixture was stirred at 60° C. overnight. The solution was concentrated, and the crude product was purified using preparative RPLC (CH$_3$CN:0.1M ammonium acetate; 55:45 to 60:40). The fractions of interest were concentrated, and the remaining mixture was extracted with methylene chloride. The organic layer was washed with brine, dried (Na$_2$SO$_4$), and concentrated yielding 28 mg (51%) of the sub-title compound.

$^1$H-NMR (400 MHz; CDCl$_3$): δ7.81 (t, 1H); 7.59 (s, 1H); 7.48 (d, 2H); 7.30 (d, 2H); 7.06 (d, 1H); 6.83 (dd, 1H); 6.69 (d, 1H); 6.04 (m, 1H); 5.35 (m, 1H); 5.27 (d, 1H); 4.92 (dd, 1H); 4.66 (dd, 1H); 4.50 (m, 1H); 4.16 (m, 2H); 3.81 (m, 1H); 3.78 (s, 3H); 2.97 (q, 1H); 2.82 (d, 1H); 2.60 (m, 2H); 2.26 (m, 1H); 2.05–1.85 (m, 4H); 0.98 (m, 2H); 0.03 (s, 9H)

(iii) (S)- or (R)-1-Hydroxy-7-methoxytetralin-1-yl-C(O)-Aze-Pab(O-allyl)

The title compound was prepared according to the method described in Example 19(vi) from (S)- or (R)-1-hydroxy-7-methoxytetralin-1-yl-C(O)-Aze-Pab(Teoc)(O-allyl) (28 mg; 44 μmol; from step (ii) above) in CH$_3$CN (2 mL) and Bu$_4$NF (1M in THF; 0.1 mL; 0.1 mmol). The crude product (21.3 mg) was purified using flash chromatography (Si gel; ethyl acetate). yielding 10 mg (46%).

$^1$H-NMR (400 MHz; CDCl$_3$): δ7.88 (t, 1H); 7.62 (d, 2H); 7.30 (d, 2H); 7.06 (d, 1H); 6.83 (dd, 1H); 6.68 (d, 1H); 6.09 (m, 1H); 5.35 (m, 1H); 5.23 (m, 1H); 4.93 (dd, 1H); 4.84 (s, 3H); 4.68 (m, 1H); 4.50 (m, 2H); 3.82 (m, 1H); 3.77 (s, 3H); 3.01 (m, 1H); 2.82 (d, 1H); 2.62 (m, 2H); 2.26 (m, 1H); 2.0–1.8 (m, 4H)

$^{13}$C-NMR (100 MHz; CDCl$_3$): (carbonyl and/or amidine carbons) δ178.8; 171.2; 159.6

LC-MS: (m/z) 493 (M+1)$^+$

Example 33

(S)- or (R)-1-Hydroxy-7-methoxytetralin-1-yl-C(O)-Aze-Pab(O-Bzl)

(i) (S)- or (R)-1-Hydroxy-7-methoxytetralin-1-yl-C(O)-Aze-Pab(Teoc)(O-Bzl)

O-Benzylhydroxylamine×HCl (82 mg; 0.52 mmol) was added to a solution of (S)- or (R)-1-hydroxy-7-methoxytetralin-1-yl-C(O)-Aze-Pab(Teoc) (50 mg; 86 μmol; see Example 32(i) above) in THF (3 mL), and the mixture was stirred at 60° C. overnight. The solution was concentrated, and the crude product was purified using preparative RPLC (CH$_3$CN:0.1M ammonium acetate; 60:40 to 70:30). The fractions of interest were concentrated, and the remaining mixture was extracted with methylene chloride. The organic layer was washed with brine, dried (Na$_2$SO$_4$), and concentrated yielding 41 mg (70%) of the sub-title compound.

$^1$H-NMR (400 MHz; CDCl$_3$): δ7.81 (t, 1H); 7.60 (s, 1H); 7.47 (d, 2H); 7.40 (m, 5H); 7.30 (d, 2H); 7.06 (d, 1H); 6.83 (dd, 1H); 6.69 (d, 1H); 5.18 (s, 2H); 4.92 (dd, 1H); 4.51 (m, 2H); 4.15 (m, 2H); 3.81 (m, 1H); 3.77 (s, 3H); 2.81 (d, 1H); 2.60 (m, 2H); 2.25 (m, 1H); 2.1–1.8 (m, 4H); 0.96 (m, 2H); 0.02 (s, 9H)

LC-MS (m/z) 687 (M+1)$^+$ (ii) (S)- or (R)-1-Hydroxy-7-methoxytetralin-1-yl-C(O)-Aze-Pab(O-Bzl)

The title compound was prepared according to the method described in Example 19(vi) above from (S)- or (R)-1-hydroxy-7-methoxytetralin-1-yl-C(O)-Aze-Pab(Teoc)(OBzl) (28 mg; 44 μmol; from step (i) above) and Bu$_4$NF (1M in THF; 0.1 mL; 0.1 mmol). The crude product (21 mg) was purified using flash chromatography (Si gel; ethyl acetate). Yield: 10 mg (35%).

$^1$H-NMR (400 MHz; CDCl$_3$): δ7.88 (t, 1H); 7.61 (d, 2H); 7.45 (d, 2H); 7.40–7.35 (m, 5H); 7.06 (d, 1H); 6.83 (dd, 1H); 6.68 (d, 1H); 5.15 (s, 2H); 4.92 (dd, 1H); 4.85 (b, 2H); 4.50 (b+m, 3H); 3.83 (m, 1H); 3.77 (s, 3H); 3.02 (m, 1H); 2.82 (d, 1H); 2.62 (m, 2H); 2.26 (m, 1H); 2.0–1.8 (m, 4H)

$^{13}$C-NMR (100 MHz; CDCl$_3$): (carbonyl and/or amidine carbons) δ178.8; 171.3; 159.6

LC-MS (m/z) 543 (M+1)$^{30}$

Example 34

(S)- or (R)-1-Hydroxy-7-methoxytetralin-1-yl-C(O)-Aze-Pab (CO-O-methallyl)

(i) p-Nitrophenyl-methallyl carbonate

Pyridine (1.21 g; 15 mmol) was added to an ice-cold solution of methallyl alcohol (1.0 g; 14 mmol) and p-nitrophenyl chloroformate (3.07 g; 15 mmol) in methylene chloride (40 mL), and the resultant mixture was stirred at RT for 1 hour, whereafter the solution was washed with KHSO$_4$ (3×) and brine, dried (Na$_2$SO$_4$), and concentrated to yield 2.9 g (88%) of the sub-title compound.

$^1$H-NMR (400 MHz; CDCl$_3$): δ8.29 (d, 2H); 7.40 (d, 2H); 5.12 (s, 1H); 5.06 (s, 1H); 4.70 (s, 2H); 1.85 (s, 3H)

(ii) (S)- or (R)-1-Hydroxy-7-methoxytetralin-1-yl-C(O)-Aze-Pab (CO-O-methallyl)

NaOH (aq.; 2M; 0.35 mL; 0.7 mmol) was added to an ice-cold solution of (S)- or (R)-1-hydroxy-7- methoxytetralin-1-yl-C(O)-Aze-Pab×HOAc (32 mg; 64 µmol; see Example 3 above) in THF (3 mL), whereafter p-nitrophenyl-methallyl carbonate (17 mg; 71 µmol; from step (i) above) was added and the solution was stirred at RT for 1 hour. The crude product was purified using preparative RPLC (CH$_3$CN:0.1M ammonium acetate (40:60)). The fractions of interest were concentrated and the water solution was extracted with methylene chloride. The organic layer was washed with brine, dried (Na$_2$SO$_4$), and concentrated. The product was dissolved in CH$_3$CN/water and freeze dried to yield 23 mg (67%) of the title compound.

$^1$H-NMR (400 MHz; CDCl$_3$): δ7.97 (t, 1H); 7.83 (d, 2H); 7.33 (d, 2H); 7.06 (d, 1H); 6.83 (dd, 1H); 6.67 (d, 1H); 5.06 (s, 2H); 4.93 (m, 2H); 4.60 (s, 2H); 4.51 (m, 2H); 3.84 (m, 1H); 3.76 (s, 3H); 3.05 (m, 1H); 2.82 (d, 1H); 2.60 (m, 2H); 2.27 (m, 1H); 2.0–1.85 (m, 4H); 1.83 (s, 3H)

$^{13}$C-NMR (100 MHz; CDCl$_3$): (carbonyl and/or amidine carbons) δ178.8; 171.4; 159.6

LC-MS (m/z) 535 (M+1)$^+$

Example 35

1-Hydroxy-7-aminotetralin-1-yl-C(O)-Aze-Pab(OH)
(i) 1-Hydroxy-7-nitrotetralin-1-yl-C(O)-Aze-Pab(Teoc)

The sub-title compound was prepared according to the method described in Example 22(iii) above from 1-hydroxy-7-nitrotetralin-1-yl-carboxylic acid (200 mg; 0.84 mmol; see Example 7(ii) above), HATU (353 mg; 0.93 mmol), H-Aze-Pab(Teoc) (417 mg, 0.93 mmol; see Example 19(iv) above) and 2,4,6-trimethylpyridine (409 mg; 3.37 mmol). The crude product was purified using preparative RPLC (CH$_3$CN:0.1M ammonium acetate (50:50)). The fractions of interest were concentrated and freeze dried to yield 226 mg (45%) of the sub-title compound.

$^1$H-NMR (400 MHz; CDCl$_3$): δ8.04 (m, 2H); 7.84 (d, 2H); 7.77 (d, 1H); 7.29 (m, 2H); 4.93 (m, 1H); 4.65–4.50 (m, 1H); 4.40 (dd, 1H); 3.96 (m, 1H); 3.82 (m, 5H); 3.15 (m, 1H); 2.95 (m, 1H); 2.75 (m, 1H); 2.52 (m, 1H); 2.44–2.25 (m, 1H); 2.1–1.9 (m, 5H); 0.05 (s, 9H)

LC-MS (m/z) 596 (M+1)$^+$ (ii) 1-Hydroxy-7-aminotetralin-1-yl-C(O)-Aze-Pab(Teoc)

A mixture of 1-hydroxy-7-nitrotetralin-1-yl-C(O)-Aze-Pab(Teoc) (48 mg; 81 µmol; from step (i) above), acetic acid (5 mg; 81 µmol), and Pd/C (5%; 24 mg) was hydrogenated at ambient temperature and pressure for 3 h. The resultant mixture was filtered through Celite, and concentrated to yield 37 mg (85%) of the title compound.

$^1$H-NMR (400 MHz; CDCl$_3$): δ7.86 (dd, 2H); 7.42 (d, 1H); 7.33 (d, 1H); 6.89 (dd, 1H); 6.58 (dd, 1H); 6.47 (b, 0.5H); 6.23 (b, 0.5H); 4.91 (m, 1H); 4.68–4.52 (m, 1H); 4.5–4.4 (m, 1H); 4.23 (m, 2H); 3.85 (m, 1H); 3.69 (m, 1H); 3.2–3.0 (m, 1H); 2.74 (d, 1H); 2.65–2.45 (m, 2H); 2.4–2.2 (m, 1H); 2.0–1.8 (m, 5H); 0.05 (s, 9H)

LC-MS (m/z) 566 (M+1)$^+$ (iii) 1-Hydroxy-7-aminotetralin-1-yl-C(O)-Aze-Pab(OH)

A mixture of hydroxylamine×HCl (29 mg; 41 mmol) and TEA (140 mg; 1.38 mmol) in THF (10 mL) was sonicated at 40° C. for 1 h. A solution of 1-hydroxy-7-aminotetralin-1-yl-C(O)-Aze-Pab(Teoc) (140 mg; 1.38 mmol; from step (ii) above) in THF (5 mL) was added, and the mixture was stirred at 40° C. for 3 days. The resultant mixture was concentrated and the crude product was purified using preparative RPLC (CH$_3$CN:0.1M ammonium acetate (30:70)). Concentration and freeze drying of the solution yielded 20 mg (65%) of the title product.

$^1$H-NMR (400 MHz; CDCl$_3$): δ8.26 (b, 0.5H); 8.03 (b, 0.5H); 7.57 (dd, 2H); 7.39 (d, 1H); 7.30 (d, 1H); 6.91 (dd, 1H); 6.65–6.55 (m, 1H); 4.98 (m, 3H); 4.65–4.30 (m+b, 4H); 3.88 (m, 0.5H); 3.69 (m, 0.5H); 3.14 (m, 1H); 2.77 (d, 1H); 2.65–2.50 (m, 2H); 2.45–2.25 (m, 1H(; 2.10 (s, 2H); 2.00–1.85 (m, 4H)

$^{13}$C-NMR (100 MHz; CD$_3$OD): (carbonyl and/or amidine carbons) δ178.2; 172.9; 155.2

LC-MS (m/z) 438 (M+1)$^+$

Example 36

(S)- or (R)-1-Hydroxy-7-methoxytetralin-1-yl-C(O)-Aze-Pab(O-Val (i) (S)- or (R)-1-Hydroxy-7-methoxytetralin-1-yl-C(O)-Aze-Pab(O-Val(Boc))

EDC×HCl (16 mg; 83 µmol) was added to an ice-cold solution of (S)- or (R)-1-hydroxy-7-methoxytetralin-1-yl-C(O)-Aze-Pab(OH) (30 mg; 66 µmol; see Example 14 above), Boc-Val-OH (18 mg; 83 µmol) and DMAP (24 mg, 0.20 mmol) in DMF (3 mL), and the solution was stirred overnight. The resultant mixture was poured into water (200 mL), and the mixture was extracted 3 times with EtOAc. The combined organic phases were washed with dilute citric acid solution and brine, dried (Na$_2$SO$_4$), and concentrated. The crude product (41 mg) was purified using preparative RPLC (CH$_3$CN:0.1M ammonium acetate (40:60)). Yield 13 mg (30%).

$^1$H-NMR (500 MHz; CDCl$_3$): δ7.94 (bt, 1H); 7.68 (d, 2H); 7.33 (d, 2H); 7.08 (d, 1H); 6.85 (dd, 1H); 6.69 (d, 1H); 5.30 (b, 2H); 5.18 (bd, 1H); 4.95 (m, 1H); 4.60–4.55 (m, 3H); 4.48 (dd, 1H); 4.32 (m, 1H); 3.86 (m, 1H); 3.79 (s, 3H); 3.05 (m, 1H); 2.83 (m, 1H); 2.7–2.55 (m, 2H); 2.28 (m, 1H); 2.22 (m, 1H); 2.05–1.85 (m, 5H); 1.48 (s, 9H); 1.08 (d, 3H); 1.04 (d, 3H)

LC-MS (m/z) 652 (M+1)$^+$ (ii) (S)- or (R)-1-Hydroxy-7-methoxytetralin-1-yl-C(O)-Aze-Pab(O-Val)

An ice-cold solution of 1-hydroxy-7-methoxytetralin-1-yl-C(O)-Aze-Pab(O-Val(Boc)) (12 mg; 18 µmol; from step (i) above) in EtOAc saturated with HCl (5 mL) was stirred for 80 minutes, whereafter the solution was concentrated, dissolved in water and freeze-dried overnight to yield 11 mg (96%) of the title compound.

$^1$H-NMR (400 MHz; D$_2$O): δ7.66 (d, 1H, minor); 7.59 (d, 2H, major); 7.45–7.35 (m, 2H); 7.2–7.1 (m, 1H); 6.95–6.85 (m, 1H); 6.75–6.65 (m, 1H); 5.25 (m, 1H, minor); 4.89 (m, 1H, major); 4.6–4.3 (m, 3H); 4.21 (m, 1H); 4.14 (m, 1H, major); 3.87 (m, 1H, major); 3.81 (s, 3H, minor); 3.63 (s, 3H, major); 2.8–1.7 (m, 9H); 1.11 (d, 6H)

$^{13}$C-NMR (100 MHz; D$_2$O): (carbonyl and/or amidine carbons) δ178.3; 173.8; 169.1; 161.4

LC-MS (m/z) 552 (M+1)$^+$

Example 37

(S)- or (R)-1-Hydroxy-7-methoxytetralin-1-yl-C(O)-Aze-(Me)Pab (i) Methyl-4-cyanobenzylideneimine A solution of p-cyanobenzaldehyde (13.1 g; 0.1 mol), methylamine (3.1 g; 0.1 mol) and p-TsOH (50 mg; cat.) in toluene (150 mL) was stirred at RT overnight, whereafter it was washed with NaHCO$_3$/(aq. (2×) and brine, dried (Na$_2$SO$_4$) and concentrated. Yield 14.4 g (100%).

$^1$H-NMR (300 MHz; CDCl$_3$): δ8.2 (s, 1H); 7.78 (d, 2H); 7.68 (d, 2H); 3.54 (s, 3H)

(ii) Methyl-4-cyanobenzylamine

NaBH$_4$ (4.54 g; 0.42 mol) was added in portions to an ice-cold solution of methyl-4-cyanobenzylideneimine (14.4 g; 0.1 mol; from step (i) above) in EtOH. The solution was stirred at RT overnight and the resultant solution was quenched with HCl (2M; aq.), washed with ether (2×), made alkaline with NaOH (2M; aq.) to pH 10, and extracted with EtOAc (3×). The organic solution was washed with water and brine, dried (Na$_2$SO$_4$), and concentrated. Yield 11.4 g (78%).

$^1$H-NMR (300 MHz; CDCl$_3$): δ7.92 (d, 2H); 7.76 (d, 2H); 4.82 (s+b, 5H); 4.40 (s, 2H)

(iii) Boc-Aze-N(Me)-Bzl-4-CN

EDC×HCl (14.5 g; 76 mmol) was added in portions to an ice-cold solution of methyl-4-cyanobenzylamine (11.4 g; 78 mmol), Boc-Aze(OH) (15.4 g; 78 mmol) and DMAP (10.5 g; 82 mmol) in CH$_3$CN (500 mL), whereafter the mixture was stirred at RT overnight. The resultant mixture was partitioned between EtOAc and water, the aqueous phase was extracted with EtOAc (3×100 mL), and the combined organic layer was washed with NaHSO$_4$ (2×), water (2×) and brine (1×), dried (Na$_2$SO$_4$) and concentrated. The yield of the crude product was 23.2 g (90%). A small amount (6.17 g; 18.7 mmol) was purified using flash chromatography (Si gel; EtOAc). Yield 4.0 g (65%).

$^1$H-NMR (400 MHz; CDCl$_3$) (complex due to rotamers): δ7.66 (d, 2H, minor); 7.60 (d, 2H, major); 7.38 (d, 2H, major); 7.31 (d, 2H, minor); 5.01 (dd, 1H); 4.9–4.7 (b, 1H); 4.6–4.45 (b, 1H); 4.07 (m, 1H); 3.90 (m, 1H); 3.00 (s, 3H, minor); 2.96 (s, 3H, major); 2.46 (m, 1H); 1.43 (s, 3H)

(iv) Aze-N(Me)-Bzl-4-CN×HCl

A solution of Boc-Aze-N(Me)-Bzl-4-CN (4.0 g; 12 mmol; from step (iii) above) in EtOAc (saturated with HCl; 50 mL) was stirred for 15 min, whereafter the solution was concentrated. Yield 3.1 g (quant.)

$^1$H-NMR (400 MHz; D$_2$O): δ7.80 (m,2H); 7.45 (m, 2H); 5.6–5.45 (m, 1H); 4.72 (s, 2H); 4.3–4.1 (m, 1H); 4.08–3.95 (m, 1H); 2.94 (s, 3H); 2.8–2.55 (m, 1H)

(v) (S)- or (R)-1-Hydroxy-7-methoxytetralin-1-yl-Aze-N(Me)-Bzl-4-CN

A solution of Aze-N(Me)-Bzl-4-CN×HCl (0.56 g; 2.1 mmol; from step (iv) above) and 2,4,6-trimethylpyridine (0.51 g, 4.2 mmol) in DMF (3 mL) was added to an ice-cold solution of 1-hydroxy-7-methoxytetralin-1-yl-carboxylic acid (0.44 g; 2.0 mmol; see Example 1(ii) above) and HATU (0.80 g; 2.1 mmol) in DMF (3 mL), and the mixture was stirred at RT overnight. The resultant mixture was poured onto water (0.5 L) and extracted with EtOAc (3×). The organic solution was washed with brine, dried (Na$_2$SO$_4$), and evaporated. The crude product (1.06 g) was purified using prep. RPLC (CH$_3$CN:0.1M ammonium acetate (32.5:67.5)), yielding two diastereoisomers, a faster diastereoisomer (Compound 37A; yield 215 mg (50%)), and a slower diastereoisomer (Compound 37B; yield 205 mg (48%)).

Compound 37A $^1$H-NMR (400 MHz; CDCl$_3$) (complex due to rotamerism): δ7.74 (d, 2H, minor); 7.66 (d, 2H, major); 7.42 (d, 2H, minor); 7.39 (d, 2H, major); 7.07 (m, 1H); 6.87–6.81 (m, 1H); 6.80 (d, 2H, major); 6.75 (d, 2H, minor); 5.22 (dd, 1H, major); 5.02 (dd, 2H, minor); 4,71 (dd, 2H); 4.60 (m, 1H); 3.98 (m, 1H); 3.81 (s, 3H, major); 3.78 (s, 3H, minor); 3.05–2.05 (m, 4H; thereof 3.05, s, 3H, minor and 3.01, s, 3H, major); 2.92–2.82 (m, 1H); 2.67 (m, 1H); 2.40 (m, 1H, minor); 2.25–2.07 (m, 3H); 1.98 (m, 2H)

(vi) (S)- or (R)-1-Hydroxy-7-methoxytetralin-1-yl-Aze-N(Me)-Bzl-4-C(NM$_2$)NOH

A solution of (S)- or (R)-1-hydroxy-7-methoxytetralin-1-yl-Aze-N(Me)-Bzl-4-CN (0.18 g; 0.42 mmol; Compound 37A from step (v) above), hydroxylamine×HCl (88 mg; 1.3 mmol) and TEA (0.18 mL; 1.3 mmol) in ethanol (abs., 3 mL) was stirred at RT for 36 h, whereafter the crude product was purified using flash chromatography (methylene chloride:methanol (90:10)). The combined fractions of interest were concentrated. Yield 0.18 g (91%).

$^1$H-NMR (400 MHz; CDCl$_3$) (complex due to rotamerism): δ7.67 (d, 2H, minor); 7.60 (d, 2H, major); 7.28 (m, 2H, partly obscured by CHCl$_3$); 7.04 (dd, 1H); 6.85–6.72 (m, 2H); 5.65 (b, 2H, major); 5.33 (b, 2H, minor); 5.20 (dd, 1H, major); 5.06 (dd, 1H, minor); 4.75–4.45 (m, 3H); 3.95 (m, 1H); 3.78 (s, 3H, major); 3.75 (s, 3H, minor); 3.00 (s, 3H, minor); 2.94 (d, 3H, major); 2.9–2.75 (m, 1H); 2.65 (m, 1H); 2.40 (m, 2H, major); 2.10 (m, 3H); 1.95 (m, 2H)

LC-MS (m/z) 467 (M+1)$^+$ (vii) (S)- or (R)-1-Hydroxy-7-methoxytetralin-1-yl-Aze-N(Me)-Bzl-4-C(NH$_2$)NH×HOAc A mixture of (S)- or (R)-1-hydroxy-7-methoxytetralin-1-yl-Aze-N(Me)-Bzl-4-C(NH$_2$)NOH (60 mg; 0.13 mmol; from step (vi) above), HOAc (15 mg; 0.26 mmol) and Pd/C (10%; 27 mg) in ethanol was chromatographed for 2 days, whereafter the mixture was filtered through Celite. The resultant solution was concentrated, and the crude product was purified using preparative RPLC (CH$_3$CN:0.1M ammonium acetate; 10:90 to 20:80). The fractions of interest were partially concentrated and freeze dried overnight. Yield 18 mg (27%).

$^1$H-NMR (400 MHz; D$_2$O) (complex due to rotamerism): δ7.83–7.73 (m, 1H); 7.68 (d, 1H); 7.50 (t, 1H); 7.43 (d, 1H); 7.17 (d, 1H); 6.93 (m, 1H); 6.82 (d, 1H); 5.40 (dd, 1H); 4.85 (d, 1H); 4.70 (m, 1H); 4.58 (d, 1H); 4.4–4.0 (m, 2H); 3.70 (s, 3H); 3.10 (s, 3H); 2.9–2.6 (m, 3H); 2.25–2.05 (m, 4H 2.0–1.7 (m, 4H)

$^{13}$C-NMR (100 MHz; D$_2$O): (carbonyl and/or amidine carbons) (complex due to rotamerism) δ178.6; 177.6; 173.8; 173.3; 173.1; 167.5; 158.5; 158.4; 158.2

LC-MS (m/z) 451 (M+1)$^+$

Example 38

9-Hydroxyfluoren-9-yl-C(O)-Aze-Pab×HOAc (i) 9-Hydroxyfluoren-9-yl-C(O)-Aze-Pab(Z)

The sub-title compound was prepared according to the method described in Example 3(i) above from 9-Hydroxyfluoren-9-yl-carboxylic acid (230 mg; 1.0 mmol), TBTU (350 mg; 1.1 mmol), H-Aze-Pab(Z)×HCl (500 mg; 1.25 mmol; prepared according to the method described in International Patent Application WO 97/02284) and DIPEA (0.52 g; 4.0 mmol). The crude product was purified using preparative RPLC (CH$_3$CN: 0.1 M ammonium acetate; 50:50). The fractions of interest were partly concentrated and were extracted with EtOAc (3×). The organic layer was dried (Na$_2$SO$_4$) and concentrated yielding 266 mg (46%) of the sub-title compound.

$^1$H-NMR (400 MHz; CDCl$_3$): δ7.92 (d, 3H); 7.66 (dd, 2H); 7.5–7.2 (m, 11 H); 5.25 (s, 3H); 4.85 (dd, 1H); 4.52 (m, 2H); 2.83 (t, 2H); 2.33 (m, 1H); 2.12 (m, 1H)

LC-MS (m/z) 575 (M+1)$^+$ (ii) 9-Hydroxyfluoren-9-yl-C(O)-Aze-Pab×HOAc

Pd/C (5%; 100 mg) and HOAc (9 μL) were added to a mixture of 9-hydroxyfluoren-9-yl-C(O)-Aze-Pab(Z) (70 mg; 0.12 mmol; from step (i) above) in EtOH (10 mL). The mixture was hydrogenated at ambient temperature and pressure for 6 h. The mixture was filtered through Celite, concentrated and dissolved in water, whereafter the aqueous solution was freeze dried. Yield 53 mg (88%).

$^1$H-NMR (400 MHz; D$_2$O): δ7.9–7.65 (m, 4H); 7.60–7.35 (m, 8H); 4.51 (s, 1H); 4.05 (m, 2H); 3.25 (t, 1H); 2.49 (m, 0.5H, rotamer); 2.28 (m, 0.5H, rotamer); 1.98–1.84 (m, 7H; within this: –1.95, s, 3H)

53

$^{13}$C-NMR (100 MHz; $D_2O$): (carbonyl and/or amidine carbons) δ173.4; 173.0; 172.6; 167.0

FAB-MS (m/z) 441 (M+1)$^+$

Example 39

The title compounds of Examples 1 to 12, 19 to 28, 37 and 38 (which are all compounds of formula I) were tested in Test A above and were all found to exhibit an $IC_{50}TT$ value of less than 0.3 μM.

Example 40

The title compounds of Examples 13 to 18 and 29 to 36 (which are all compounds of formula Ia) were tested in Test A above and were all found to exhibit an $IC_{50}TT$ value of more than 1 μM.

Example 41

The title compounds of Examples 13 to 18 and 29 to 36 (which are all compounds of formula Ia) were tested in Test E above and were all found to exhibit oral and/or parenteral bioavailability in the rat as the corresponding active inhibitor of formula I.

Abbreviations
Ac=acyl
AcOH=acetic acid
Aze=azetidine-2-carboxylate
AzeOH=azetidine-2-carboxylic acid
DCC=dicyclohexylcarbodiimide
DIPEA=diisopropylethylamine
DMAP=N,N-dimethyl amino pyridine
DMF=dimethylformamide
DMSO=dimethylsulphoxide
EDC=1-(3-dimethylaminopropyl)-3-ethylcarbodiimide hydrochloride
Et=ethyl
$Et_2O$=diethyl ether
EtOAc=ethyl acetate
EtOH=ethanol
h=hours
HATU=O-(azabenzotriazol-1-yl)-N,N,N',N'-tetramethyluronium hexafluorophosphate
HBTU=[N,N,N',N'-tetramethyl-O-(benzotriazol-1-yl) uronium hexafluorophosphate]
HCl(g)=hydrogen chloride gas
HOAc=acetic acid
LC=liquid chromatography
Me=methyl
MeOH=methanol
Pab-H=para-amidinobenzylamino
H-Pab-H=para-amidinobenzylamine
QF=tetrabutylammonium fluoride ($Bu_4NF$)
RPLC=preparative reverse phase high performance liquid chromatography
RT=room temperature
TBTU=[N,N,N',N'-tetramethyl-O-(benzotriazol-1-yl) uronium tetrafluoroborate]
TEA=triethylamine
Teoc=2-(trimethylsilyl)ethoxycarbonyl
THF=tetrahydrofuran
TLC=thin layer chromatography
Val=L-valine
Z=benzyloxycarbonyl Prefixes n, S, i and t have their usual meanings: normal, iso, secondary and tertiary.

54

What is claimed is:
1. A compound of formula I,

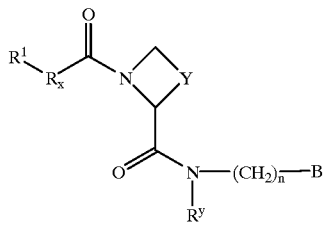

I wherein
$R^1$ represents $OR^{1d}$;
$R^{1d}$ represents H, $C(O)R^{11}$, $SiR^{12}R^{13}R^{14}$ or $C_{1-6}$ alkyl, which latter group is optionally substituted or terminated by one or more substituents selected from $OR^{15}$ or $(CH_2)_qR^{16}$;
$R^{12}$, $R^{13}$ and $R^{14}$ independently represent H, phenyl or $C_{1-6}$ alkyl;
$R^{16}$ represents $C_{1-4}$ alkyl, phenyl, OH, $C(O)OR^{17}$ or $C(O)N(H)R^{18}$;
$R^{18}$ represents H, $C_{1-4}$ alkyl or $CH_2C(O)OR^{19}$;
$R^{15}$ and $R^{17}$ independently represent H, $C_{1-6}$ alkyl or $C_{1-3}$ alkylphenyl;
$R^{11}$ and $R^{19}$ independently represent H or $C_{1-4}$ alkyl; and
q represents 0, 1 or 2;
$R_x$ represents a structural fragment of formula IIa, IIb or IIc,

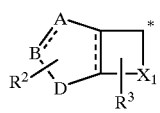

IIa

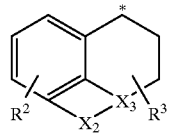

IIb

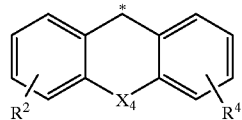

IIc wherein
the dotted lines independently represent optional double bonds;
A and B independently represent O or S, CH or $CH_2$ (as appropriate), or N or $N(R^{21})$ (as appropriate);
D represents $—CH_2—$, O, S, $N(R^{22})$, $—(CH_2)_2—$, $—CH=CH—$, $—CH_2N(R^{22})—$, $—N(R^{22})CH_2—$, $—CH=N—$, $—N=CH—$, $—CH_2O—$, $—OCH_2—$, $—CH_2S—$ or $—SCH_2—$;
$X_1$ represents $C_{2-4}$ alkylene; $C_{2-3}$ alkylene interrupted by Z; $—C(O)—Z—A^1$; $—Z—C(O)—A^1—$; $—CH_2—C(O)—A^1$; $—Z—C(O)—Z—A^2—$; $—CH_2—Z—C(O)—A^2—$; $—Z—CH_2—C(O)—A^2—$; $—Z—CH_2—S(O)_m—A^2—$; $—CH_2—Z—S(O)_m—A^2—$; $—C(O)—A^3$, $—Z—A^3—$; or $—A^3—Z—$;

$X_2$ represents $C_{2-3}$ alkylene, —C(O)—$A^4$— or —$A^4$—C(O)—

$X_3$ represents CH or N;

$X_4$ represents a single bond, O, S, C(O), N($R^{23}$), —CH($R^{23}$)—, —CH($R^{23}$)—CH($R^{24}$)— or —C($R^{23}$)=C($R^{24}$)—;

$A^1$ represents a single bond or $C_{1-2}$ alkylene;

$A^2$ represents a single bond or —$CH_2$—;

$A^3$ represents $C_{1-3}$ alkylene;

$A^4$ represents C(O) or $C_{1-2}$ alkylene;

Z represents, at each occurrence, O, S(O)$_m$ or N($R^{25}$);

m represents, at each occurrence, 0, 1 or 2;

$R^2$ and $R^4$ independently represent one or more optional substituents selected from $C_{1-4}$ alkyl (which latter group is optionally substituted by one or more halo substituent), $C_{1-4}$ alkoxy, methylenedioxy, halo, hydroxy, cyano, nitro, $SO_2NH_2$, C(O)O$R^{26}$ or N($R^{27}$)$R^{28}$;

$R^3$ represents an optional substituent selected from OH or $C_{1-4}$ alkoxy; $R^{21}$, $R^{22}$, $R^{23}$, $R^{24}$, $R^{25}$, $R^{26}$, $R^{27}$ and $R^{28}$ independently represent H or $C_{1-4}$ alkyl;

Y represents $CH_2$;

$R^y$ represents H or $C_{1-4}$ alkyl;

n represents 0, 1, 2, 3 or 4; and

B represents a structural fragment of formula IIIa or IIIc

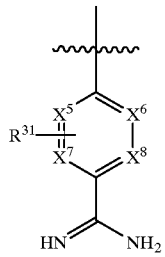

IIIa

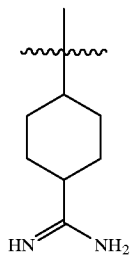

IIIc wherein $X^5$, $X^6$, $X^7$ and $X^8$ independently represent CH, N or N—O; and $R^{31}$ represents an optional substituent selected from halo and $C_{1-4}$ alkyl; or a pharmaceutically acceptable salt thereof;

provided that:
(a) in formula IIa, A and B do not both represent O or S;
(b) in formula IIa, B and D do not both represent O or S;
(c) when $X_1$ represents —C(O)—Z—$A^1$,—Z—$CH_2$S(O)$_m$—$A^2$—, —$CH_2$—Z—S(O)$_m$—$A^2$ or —Z—C(O)—Z—$A^2$, then $A^1$ or $A^2$ (as appropriate) do not represent a single bond; and
(d) when $X_4$ represents —CH($R^{23}$)—, $R^1$ does not represent OH.

2. A compound of formula I, as defined in claim 1, wherein $R^1$ represents OH.

3. A compound of formula I, as defined in claim 1, wherein $R_x$ represents a structural fragment of formula IIa.

4. A compound of formula I, as defined in claim 1, wherein, when $R_x$ represents a structural fragment of formula IIa, the dotted lines represent bonds, A and B both represent CH and D represents —CH=CH—.

5. A compound of formula I, as defined in claim 1, wherein, when $R_x$ represents a structural fragment of formula IIa, $X_1$ represents $C_2$— or $C_3$-alkylene, —O($CH_2$)— or —O($CH_2$)$_2$—.

6. A compound of formula I, as defined in claim 5 wherein $X_1$ represents $C_3$-alkylene or —O($CH_2$)$_2$—.

7. A compound of formula I, as defined in claim 1, wherein, when B represents a structural fragment of formula IIIa, $X^5$, $X^6$, $X^7$ and $X^8$ all represents CH.

8. A compound of formula I, as defined in claim 1, wherein, when $R_x$ represents a structural fragment of formula IIa, and $R^2$ represents at least one substituent, a point of substitution is at the carbon atom which is at position B.

9. A compound of formula I, as defined in claim 1, wherein, when $R_x$ represents a structural fragment of formula IIa, the dotted lines represent bonds, A and B both represent CH, D represents —CH=CH—, and $R^2$ represents at least one substituent, the ring is substituted either at the carbon atom in the —CH=CH— group (position D) which is adjacent to the ring junction, or at the carbon atom which is at position B, or at both of these sites.

10. A compound of formula I, as defined in claim 1, wherein the fragment

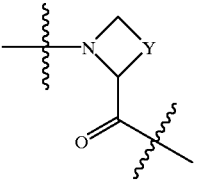

is in the S-configuration.

11. A compound which is:

(S)- or (R)-1-hydroxy-7-methoxytetralin-1-yl-C(O)-Pro-Pab;

(R)- or (S)-1-hydroxy-7-methoxytetralin-1-yl-C(O)-Pro-Pab;

(S)- or (R)-1-hydroxy-7-methoxytetralin-1-yl-C(O)-Aze-Pab×HOAc;

(R)- or (S)-1-hydroxy-7-methoxytetralin-1-yl-C(O)-Aze-Pab;

1-hydroxy-5-methoxytetralin-1-yl-C(O)-Aze-Pab×HOAc;

1-hydroxy-5,7-dimethyltetralin-1-yl-C(O)-Aze-Pab×HOAc;

1-hydroxy-7-aminotetralin-1-yl-C(O)-Aze-Pab×HOAc;

1-hydroxytetralin-1-yl-C(O)-Aze-Pab×HOAc;

7-methoxytetralin-1-yl-C(O)-Aze-Pab×HOAc;

(R)- and (S)-7-methoxy-1-methyltetralin-1-yl-C(O)-Aze-Pab;

4-hydroxy-6-methoxychroman-4-yl-C(O)-Aze-Pab×OAc;

(S)- and (R)-1-hydroxy-4-methoxyindan-1-yl-C(O)-Aze-Pab;

1-hydroxy-5-methoxytetralin-1-yl-C(O)-Aze-Pab(OH);

(S)- or (R)-1-hydroxy-7-methoxytetralin-1-yl-C(O)-Aze-Pab(OH);

4-hydroxy-6-methoxychroman-4-yl-C(O)-Aze-Pab(OH);

4-hydroxy-6-methoxychroman-4-yl-C(O)-Aze-Pab(OMe);

(S)- or (R)-1-hydroxy-7-methoxytetralin-1-yl-C(O)-Aze-Pab(C(O)OCH$_2$CCl$_3$);

(S)- or (R)-1-hydroxy-7-methoxytetralin-1-yl-C(O)-Aze-Pab(C(O)OCH$_2$CH$_3$);

7-methoxy-1-allyltetralin-1-yl-C(O)-Aze-Pab×HOAc;

(S)- or (R)-1-hydroxy-7-chlorotetralin-1-yl-C(O)-Pro-Pab;

1-n-propyl-7-methoxytetralin-1-yl-C(O)-Aze-Pab×HOAc;

6-chloro-4-hydroxychroman-4-yl-C(O)-Aze-Pab×HOAc;

4-hydroxychroman-4-yl-C(O)-Aze-Pab×HOAc;

6,8-dichloro-4-hydroxychroman-4-yl-C(O)-Aze-Pab×HOAc;

6fluoro-4-hydroxychroman-4-yl-C(O)-Aze-Pab×HOAc;

4-hydroxy-6-methylchroman-4-yl-C(O)-Aze-Pab×HOAc;

8-chloro-4-hydroxy-6-methoxychroman-4-yl-C(O)-Aze-Pab×HOAc;

6-chloro-4-hydroxy-8-methylchroman-4-yl-C(O)-Aze-Pab×HOAc;

(S)- or (R)-1-hydroxy-7-methoxytetralin-1-yl-C(O)-Aze-Pab(O-C(O)-i-Pr);

(S)- or (R)-1-hydroxy-7-methoxytetralin-1-yl-C(O)-Aze-Pab(O-C(O)-Et);

(S)- or (R)-1-hydroxy-7-methoxytetralin-1-yl-C(O)-Aze-Pab(O-C(O)-Ch);

(S)- or (R) 1-hydroxy-7-methoxytetralin-1-yl-C(O)-Aze-Pab(O-allyl);

(S)- or (R)-1-hydroxy-7-methoxytetralin-1-yl-C(O)-Aze-Pab(O-Bzl);

(S)- or (R)-1-hydroxy-7-methoxytetralin-1-yl-C(O)-Aze-Pab(CO-O-methallyl);

1-hydroxy-7-aminotetralin-1-yl-C(O)-Aze-Pab(OH);

(S)- or (R)-1-hydroxy-7-methoxytetralin-1-yl-C(O)-Aze-Pab(O-Val);

(S)- or (R)-1-hydroxy-7-methoxytetralin-1-yl-C(O)-Aze-(Me)Pab; or 9-hydroxyfluoren-9-yl-C(O)-Aze-Pab×HOAc.

12. A compound of formula Ia,

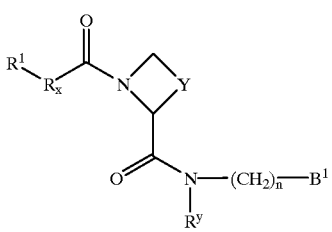

Ia wherein B$^1$ represents a structural fragment of formula IIId or IIIf,

IIIf

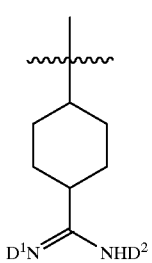

IIId

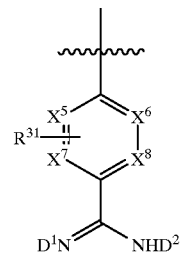

wherein D$^1$ and D$^2$ independently represent H, OH, OR$^a$, OC(O)R$^b$, OC(O)OR$^c$, C(O)OR$^d$, C(O)R$^e$; in which R$^a$ represents phenyl, benzyl, C$_{1-7}$ alkyl (which latter group is optionally interrupted by oxygen or is optionally substituted by halo) or —C(R$^f$)(R$^g$)—OC(O)R$^h$;

R$^b$ represents C$_{1-17}$ alkyl (which latter group is optionally substituted by C$_{1-6}$ alkoxy, C$_{1-6}$ acyloxy, amino or halo); C$_{1-6}$ alkoxy, C$_{3-7}$ cycloalkyl, phenyl, naphthyl or C$_{1-3}$ alkylphenyl (which latter five groups are optionally substituted by C$_{1-6}$ alkyl or halo); or —[C(R$^i$)(R$^j$)]$_m$OC(O)R$^k$;

R$^c$ represents C$_{1-17}$ alkyl, phenyl, 2-naphthyl (which latter three groups are optionally substituted by C$_{1-6}$alkyl, Si(R$^{aa}$)(R$^{ab}$)(R$^{ac}$) or halo), —[C(R$^m$)(R$^n$)]$_n$OC(O)R$^p$, or —CH$_2$—Ar$^1$;

R$^d$ represents 2-naphthyl, phenyl, C$_{1-3}$ alkylphenyl (which latter three groups are optionally substituted by C$_{1-6}$ alkyl, C$_{1-6}$ alkoxy, nitro, Si(R$^{ba}$)(R$^{bb}$)(R$^{bc}$) or halo), C$_{1-12}$ alkyl (which latter group is optionally substituted by C$_{1-6}$ alkoxy, C$_{1-6}$ acyloxy or halo), —[C(R$^q$)(R$^r$)]$_p$OC(O)R$^s$ or —CH$_2$—Ar$^2$;

R$^e$ represents phenyl, benzyl, C$_{1-6}$ alkyl (which latter group is optionally interrupted by oxygen) or —[C(R$^t$)(R$^u$)]$_r$OC(O)R$^v$;

R$^{aa}$, R$^{ab}$, R$^{ac}$, R$^{ba}$, R$^{bb}$ and R$^{bc}$ independently represent C$_{1-6}$ alkyl or phenyl; R$^f$, R$^g$, R$^i$, R$^j$, R$^m$, R$^n$, R$^q$, R$^r$, R$^t$ and R$^u$ independently represent H or C$_{1-6}$ alkyl;

R$^h$, R$^k$, R$^p$, R$^s$ and R$^v$ independently represent C$_{1-17}$ alkyl (which latter group is optionally substituted by C$_{1-6}$ alkoxy, C$_{1-6}$ acyloxy or halo); C$_{1-6}$ alkoxy, C$_{3-7}$ cycloalkyl, phenyl, naphthyl or C$_{1-3}$ alkylphenyl (which latter five groups are optionally substituted by C$_{1-6}$ alkyl or halo);

Ar$^1$ and Ar$^2$ independently represent the structural fragment

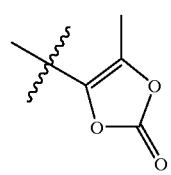

m and r independently represent 3 or 4;

n and p independently represent 1, 2 or 3; and

R$^1$, R$_x$, Y, R$^y$, n, X$^5$, X$^6$, X$^7$, X$^8$ and R$^{31}$ are as defined in claim 1;

or a pharmaceutically acceptable salt thereof;

provided that D$^1$ and D$^2$ do not both represent H.

13. A compound of formula Ia, as claimed in claim 12, wherein D$^1$ represents H and D$^2$ represents OH, OCH$_3$, OC(O)R$^b$ or C(O)OR$^d$, wherein R$^b$ and R$^d$ are as defined in claim 12.

14. A process for the preparation of compounds of formula I as defined in claim 1 which comprises:

(a) a coupling reaction comprising:

(i) the coupling of a compound of formula IV,

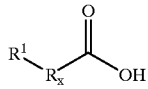

IV wherein $R^1$ and $R_x$ are as defined in claim 1 with a compound of formula V,

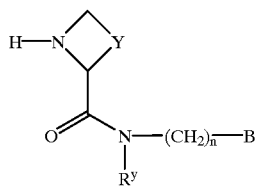

V wherein $R^y$, Y, n and B are as defined in claim 1; or (ii) the coupling of a compound of formula VI,

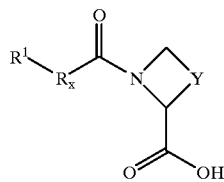

VI wherein $R^1$, $R_x$ and Y are as defined in claim 1 with a compound of formula VII,

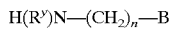

VII wherein $R^y$, n and B are as defined in claim 1;

(b) deprotection of a compound of formula Ia

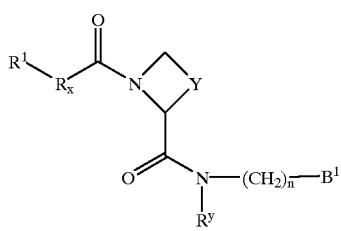

Ia wherein $B^1$ defines a structural fragment of formula IIId or IIIf

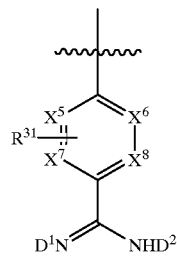

IIId

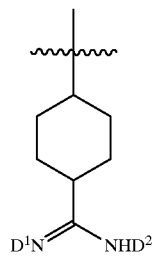

IIIf wherein $D^1$ and $D^2$ independently represent H, OH, $OR^a$, $OC(O)R^b$, $OC(O)OR^c$, $C(O)OR^d$, $C(O)R^e$; in which $R^a$ represents phenyl, benzyl, $C_{1-7}$ alkyl (which latter group is optionally interrupted by oxygen or is optionally substituted by halo) or $C(R^f)(R^g)$—$OC(O)R^h$;

$R^b$ represents $C_{1-17}$ alkyl (which latter group is optionally substituted by $C_{1-6}$ alkoxy, $C_{1-6}$ acyloxy, amino or halo); $C_{1-6}$ alkoxy, $C_{3-7}$ cycloalkyl, phenyl, naphthyl or $C_{1-3}$ alkylphenyl (which latter five groups are optionally substituted by $C_{1-6}$ alkyl or halo); or —$[C(R^i)(R^j)]_mOC(O)R^k$;

$R^c$ represents $C_{1-17}$ alkyl, phenyl, 2-naphthyl (which latter three groups are optionally substituted by $C_{1-6}$ alkyl, $Si(R^{aa})(R^{ab})(R^{ac})$ or halo), —$[C(R^m)(R^n)]_nOC(O)R^p$, or —$CH_2$—$Ar^1$;

$R^d$ represents 2-naphthyl, phenyl, $C_{1-3}$ alkylphenyl (which latter three groups are optionally substituted by $C_{1-6}$ alkyl, $C_{1-6}$ alkoxy, nitro, $Si(R^{ba})(R^{bb})(R^{bc})$ or halo), $C_{1-2}$ alkyl (which latter group is optionally substituted by $C_{1-6}$ alkoxy, $C_{1-6}$ acyloxy or halo), —$[C(R^q)R^r)]_pOC(O)R^s$ or —$CH_2$—$Ar^2$;

$R^e$ represents phenyl, benzyl, $C_{1-6}$ alkyl (which latter group is optionally interrupted by oxygen) or —$C(R^t)(R^u)_rOC(O)R^v$;

$R^{aa}$, $R^{ab}$, $R^{ac}$, $R^{ba}$, $R^{bb}$ and $R^{bc}$ independently represent $C_{1-6}$ alkyl or phenyl; $R^f$, $R^g$, $R^i$, $R^j$, $R^m$, $R^n$, $R^q$, $R^r$, $R^t$ and $R^u$ independently represent H or $C_{1-6}$ alkyl;

$R^h$, $R^k$, $R^p$, $R^s$ and $R^v$ independently represent $C_{1-17}$ alkyl (which latter group is optionally substituted by $C_{1-6}$ alkoxy, $C_{1-6}$ acyloxy or halo): $C_{1-6}$ alkoxy, $C_{3-7}$ cycloalkyl, phenyl, naphthyl or $C_{1-3}$ alkylphenyl (which latter five groups are optionally substituted by $C_{1-6}$ alkyl or halo);

$Ar^1$ and $Ar^2$ independently represent the structural fragment

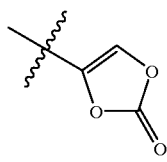

m and r independently represent 3 or 4;
n and p independently represent 1, 2 or 3; and
$R^1$, $R_x$, Y, $R^y$, n, $X^5$, $X^6$, $X^7$, $X^8$ and $R^{31}$ are as defined in claim 1;
or a pharmaceutically acceptable salt thereof;
provided that $D^1$ and $D^2$ do not both represent H.

15. A pharmaceutical formulation including a compound as defined in claim 1, or a pharmaceutically acceptable salt thereof, in admixture with a pharmaceutically acceptable adjuvant, diluent or carrier.

16. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition.

17. A method as claimed in claim 16, wherein the condition is thrombosis.

18. A method as claimed in claim 16, wherein the condition is hypercoagulability in blood and tissues.

* * * * *